(12) United States Patent
Blake et al.

(10) Patent No.: US 10,954,541 B2
(45) Date of Patent: Mar. 23, 2021

(54) CELL-FREE PRODUCTION OF RIBONUCLEIC ACID

(71) Applicant: GreenLight Biosciences, Inc., Medford, MA (US)

(72) Inventors: William Jeremy Blake, Winchester, MA (US); Drew S. Cunningham, Cambridge, MA (US); Daniel MacEachran, Medford, MA (US); Mehak Gupta, Medford, MA (US); James Robbins Abshire, Cambridge, MA (US)

(73) Assignee: GreenLight Biosciences, Inc., Medford, MA (US)

( * ) Notice: Subject to any disclaimer, the term of this patent is extended or adjusted under 35 U.S.C. 154(b) by 136 days.

(21) Appl. No.: 15/480,617

(22) Filed: Apr. 6, 2017

(65) Prior Publication Data

US 2017/0292138 A1 Oct. 12, 2017

Related U.S. Application Data

(60) Provisional application No. 62/452,550, filed on Jan. 31, 2017, provisional application No. 62/319,220, filed on Apr. 6, 2016.

(51) Int. Cl.
| | | |
|---|---|---|
| *C12P 19/34* | (2006.01) | |
| *C12N 9/22* | (2006.01) | |
| *C12N 1/06* | (2006.01) | |
| *C12N 9/12* | (2006.01) | |

(52) U.S. Cl.
CPC ............... *C12P 19/34* (2013.01); *C12N 1/06* (2013.01); *C12N 9/1229* (2013.01); *C12N 9/1247* (2013.01); *C12N 9/22* (2013.01); *C12Y 207/04001* (2013.01); *C12Y 207/04006* (2013.01); *C12Y 207/07006* (2013.01); *C12Y 301/13001* (2013.01)

(58) Field of Classification Search
None
See application file for complete search history.

(56) References Cited

U.S. PATENT DOCUMENTS

| | | |
|---|---|---|
| 3,223,592 A | 12/1965 | Sakaguchi et al. |
| 3,684,652 A | 8/1972 | Nakayama et al. |
| 3,950,357 A | 4/1976 | Kahan et al. |
| RE28,886 E | 6/1976 | Nakayama et al. |
| 4,006,060 A | 2/1977 | Kahan et al. |
| 4,194,047 A | 3/1980 | Christensen et al. |
| 4,248,966 A | 2/1981 | Demain et al. |
| 4,266,034 A | 5/1981 | Patel |
| 4,270,537 A | 6/1981 | Romaine |
| 4,292,436 A | 8/1981 | Liu et al. |
| 4,329,481 A | 5/1982 | Liu et al. |
| 4,374,772 A | 2/1983 | Hazen et al. |
| 4,438,201 A | 3/1984 | Kubo et al. |
| 4,458,066 A | 7/1984 | Caruthers et al. |
| 4,460,689 A | 7/1984 | Foor et al. |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 4,946,783 A | 8/1990 | Beckwith et al. |
| 4,950,603 A | 8/1990 | Ingolia et al. |
| 5,000,000 A | 3/1991 | Ingram et al. |
| 5,001,055 A | 3/1991 | Imahori et al. |
| 5,015,235 A | 5/1991 | Crossman |
| 5,064,413 A | 11/1991 | McKinnon et al. |
| 5,070,020 A | 12/1991 | Ingolia et al. |
| 5,141,496 A | 8/1992 | Dalto et al. |
| 5,190,521 A | 3/1993 | Hubbard et al. |
| 5,312,335 A | 5/1994 | McKinnon et al. |
| 5,319,122 A | 6/1994 | Friedman |
| 5,328,483 A | 7/1994 | Jacoby |
| 5,334,144 A | 8/1994 | Alchas et al. |
| 5,339,163 A | 8/1994 | Homma et al. |
| 5,417,662 A | 5/1995 | Hjertman et al. |
| 5,436,131 A | 7/1995 | Condra et al. |
| 5,466,220 A | 11/1995 | Brenneman |
| 5,383,851 A | 12/1995 | McKinnon et al. |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |

(Continued)

FOREIGN PATENT DOCUMENTS

| | | |
|---|---|---|
| CN | 1329506 C | 8/2007 |
| CN | 105219822 | 1/2016 |

(Continued)

OTHER PUBLICATIONS

Kohrer et al. Use of T7 RNA polymerase in an Optimized *Escherchia coli* Coupled in vitro Transcription-Translation System. Application in Regulatory Studies and Expression of Long Transcription Units. Feb. 1996. Eur. J. Biochem. vol. 236, No. 1, pp. 234-239. (Year: 1996).*
Invitation to Pay Additional Fees for PCT/US2012/054195 dated Jan. 30, 2013.
International Search Report and Written Opinion for PCT/US2012/054195 dated Apr. 12, 2013.
International Preliminary Report on Patentability for PCT/US2012/054195 dated Mar. 20, 2014.
Invitation to Pay Additional Fees for PCT/US2011/035639 dated Sep. 12, 2011.
International Search Report and Written Opinion for PCT/US2011/035639 dated Nov. 18, 2011.
International Preliminary Report on Patentability for PCT/US2011/035639 dated Nov. 22, 2012.

(Continued)

*Primary Examiner* — Channing S Mahatan
(74) *Attorney, Agent, or Firm* — Wolf, Greenfield & Sacks, P.C.

(57) ABSTRACT

Provided herein, in some aspects, are methods and compositions for cell-free production of ribonucleic acid.

32 Claims, 19 Drawing Sheets

Specification includes a Sequence Listing.

(56) References Cited

U.S. PATENT DOCUMENTS

| | | |
|---|---|---|
| 5,593,856 A | 1/1997 | Choi et al. |
| 5,599,302 A | 2/1997 | Lilley et al. |
| 5,649,912 A | 7/1997 | Peterson |
| 5,665,566 A | 9/1997 | Lavaille |
| 5,672,497 A | 9/1997 | Cox et al. |
| 5,704,911 A | 1/1998 | Parsons |
| 5,871,922 A | 2/1999 | Salmond et al. |
| 5,893,397 A | 4/1999 | Peterson et al. |
| 5,993,412 A | 11/1999 | Deily et al. |
| 6,159,693 A | 12/2000 | Shultz et al. |
| 6,168,931 B1 | 1/2001 | Swartz et al. |
| 6,387,667 B1 | 5/2002 | Maruyama et al. |
| 6,440,688 B1 | 8/2002 | Bruce et al. |
| 6,472,169 B1 | 10/2002 | Frost et al. |
| 6,531,299 B1 | 3/2003 | Khosla et al. |
| 6,613,552 B1 | 9/2003 | Frost et al. |
| 6,746,859 B1 | 6/2004 | LaVallie |
| 6,921,659 B2 | 7/2005 | Joly |
| 6,994,986 B2 | 2/2006 | Swartz et al. |
| 7,041,479 B2 | 5/2006 | Swartz et al. |
| 7,223,390 B2 | 5/2007 | Brown |
| 7,226,767 B2 | 6/2007 | Maruyama et al. |
| 7,312,049 B2 | 12/2007 | Calhoun et al. |
| 7,338,789 B2 | 3/2008 | Swartz et al. |
| 7,341,852 B2 | 3/2008 | Voloshin et al. |
| 7,351,563 B2 | 4/2008 | Swartz et al. |
| 7,579,005 B2 | 8/2009 | Keeler et al. |
| 8,859,247 B2 | 10/2014 | Koltermann et al. |
| 8,916,358 B2 | 12/2014 | Swartz |
| 8,956,833 B2 | 2/2015 | Swartz |
| 9,469,861 B2 | 10/2016 | Blake et al. |
| 9,611,487 B2 | 4/2017 | Blake et al. |
| 9,637,746 B2 | 5/2017 | Klein-Marcuschamer |
| 9,688,977 B2 | 6/2017 | Blake et al. |
| 10,036,001 B2 | 7/2018 | Swartz |
| 10,316,342 B2 | 6/2019 | MacEachran et al. |
| 10,421,953 B2 | 9/2019 | Blake et al. |
| 2002/0058303 A1 | 5/2002 | Swartz et al. |
| 2002/0127633 A1 | 9/2002 | Dilley et al. |
| 2002/0160459 A1 | 10/2002 | Berry et al. |
| 2003/0022178 A1 | 1/2003 | Schneewind et al. |
| 2003/0040086 A1 | 2/2003 | Dodge et al. |
| 2003/0113778 A1 | 6/2003 | Schulte et al. |
| 2004/0002103 A1 | 1/2004 | Short |
| 2004/0038250 A1 | 2/2004 | Nunez et al. |
| 2004/0091976 A1 | 5/2004 | Deng et al. |
| 2004/0209321 A1 | 10/2004 | Swartz et al. |
| 2005/0054044 A1 | 3/2005 | Swartz et al. |
| 2005/0239174 A1 | 10/2005 | Bao et al. |
| 2006/0234358 A1 | 10/2006 | Anderlei et al. |
| 2006/0281148 A1 | 12/2006 | Swartz et al. |
| 2007/0111283 A1 | 5/2007 | Cannon et al. |
| 2007/0154983 A1 | 7/2007 | Calhoun et al. |
| 2007/0161092 A1 | 7/2007 | Townsend et al. |
| 2007/0202198 A1 | 8/2007 | Purcell |
| 2008/0021205 A1 | 1/2008 | Blau et al. |
| 2008/0131925 A1 | 6/2008 | Berk et al. |
| 2009/0042244 A1 | 2/2009 | Voloshin et al. |
| 2009/0053779 A1 | 2/2009 | Lee et al. |
| 2009/0124012 A1 | 5/2009 | Nikolsky et al. |
| 2009/0155867 A1 | 6/2009 | Soucaille |
| 2009/0275096 A1 | 11/2009 | Burgard et al. |
| 2009/0275097 A1 | 11/2009 | Sun et al. |
| 2009/0312539 A1 | 12/2009 | Gnanaprakasam et al. |
| 2009/0325245 A1 | 12/2009 | Soucaille et al. |
| 2010/0120105 A1 | 5/2010 | Anthony et al. |
| 2010/0136640 A1 | 6/2010 | Lee et al. |
| 2010/0143997 A1 | 6/2010 | Buelter et al. |
| 2010/0291653 A1 | 11/2010 | Ness et al. |
| 2011/0008867 A1 | 1/2011 | Zarur et al. |
| 2011/0099670 A1 | 4/2011 | Koops et al. |
| 2011/0124069 A1 | 5/2011 | Mampel et al. |
| 2011/0262946 A1 | 10/2011 | Roy et al. |
| 2011/0269198 A1 | 11/2011 | Klein-Marcuschamer |
| 2011/0275116 A1 | 11/2011 | Swartz |
| 2011/0312052 A1 | 12/2011 | Koltermann et al. |
| 2012/0052547 A1 | 3/2012 | Swartz |
| 2012/0070870 A1 | 3/2012 | Way et al. |
| 2013/0065878 A1 | 3/2013 | Blake et al. |
| 2014/0193869 A1 | 7/2014 | Blake et al. |
| 2014/0271559 A1 | 9/2014 | Baum et al. |
| 2015/0037868 A1 | 2/2015 | Blake et al. |
| 2015/0064751 A1 | 3/2015 | Swartz |
| 2015/0191753 A1 | 7/2015 | Swartz |
| 2015/0337306 A1* | 11/2015 | Lieberman ............ A61K 31/713 514/44 A |
| 2016/0028101 A1 | 1/2016 | Zhang et al. |
| 2016/0115558 A1 | 4/2016 | Swartz |
| 2017/0044554 A1 | 2/2017 | Zhang et al. |
| 2017/0096692 A1 | 4/2017 | Blake et al. |
| 2017/0159058 A1 | 6/2017 | Blake et al. |
| 2017/0247724 A1 | 8/2017 | Klein-Marcuschamer |
| 2017/0253866 A1 | 9/2017 | Blake et al. |
| 2018/0030416 A1 | 2/2018 | Beltran Pavez et al. |
| 2018/0087045 A1* | 3/2018 | Blake ....................... C12Q 1/68 |
| 2018/0273985 A1 | 9/2018 | Blake |
| 2018/0320210 A1 | 11/2018 | MacEachran et al. |
| 2019/0144489 A1 | 5/2019 | Cunningham et al. |

FOREIGN PATENT DOCUMENTS

| | | |
|---|---|---|
| EP | 0 377 295 A1 | 7/1990 |
| EP | 0 444 775 A1 | 9/1991 |
| EP | 0 553 821 A1 | 8/1993 |
| EP | 1261696 A1 | 12/2002 |
| EP | 1264894 A1 | 12/2002 |
| EP | 1 279 736 A1 | 1/2003 |
| EP | 1 433 856 A1 | 6/2004 |
| EP | 1 502 956 A1 | 2/2005 |
| EP | 1 514 927 A1 | 3/2005 |
| EP | 1631675 A1 | 3/2006 |
| EP | 1 939 210 A1 | 7/2008 |
| EP | 1587947 B1 | 1/2010 |
| EP | 2 204 453 A1 | 7/2010 |
| EP | 2377928 A2 | 10/2011 |
| GB | 2 018 822 A | 10/1979 |
| JP | S61-260895 A | 11/1986 |
| JP | S63-7788 A | 1/1988 |
| JP | H01-228473 A | 9/1989 |
| JP | H07-298893 A | 11/1995 |
| JP | H08-502176 A | 3/1996 |
| JP | H08-196284 A | 8/1996 |
| JP | H10-500849 A | 1/1998 |
| JP | 2002-535008 A | 10/2002 |
| JP | 2007-534338 A | 11/2007 |
| JP | 2009-531050 A | 9/2009 |
| JP | 2013/021967 A | 2/2013 |
| JP | 2013-526277 A | 6/2013 |
| JP | 2013-537802 A | 10/2013 |
| JP | 5800218 B2 | 10/2015 |
| RU | 2435862 | 12/2011 |
| WO | WO 95/32294 A1 | 11/1995 |
| WO | WO 97/13537 A1 | 4/1997 |
| WO | WO 97/37705 A1 | 10/1997 |
| WO | WO 98/07690 A1 | 2/1998 |
| WO | WO 99/34850 A1 | 7/1999 |
| WO | WO 99/50389 | 10/1999 |
| WO | WO 00/03581 A1 | 1/2000 |
| WO | WO 00/39288 A1 | 7/2000 |
| WO | WO 00/44923 A1 | 8/2000 |
| WO | WO 00/055353 A1 | 9/2000 |
| WO | WO 2000/61768 A2 | 10/2000 |
| WO | WO 03/038117 A2 | 5/2003 |
| WO | WO 2003/054792 A2 | 7/2003 |
| WO | WO 2005/030949 A1 | 4/2005 |
| WO | WO 2005/030995 A1 | 4/2005 |
| WO | WO 2005/052117 A2 | 6/2005 |
| WO | WO 05/098048 A1 | 10/2005 |
| WO | WO 2006/001382 A1 | 1/2006 |
| WO | WO 2006/090385 A2 | 8/2006 |
| WO | WO 07/053655 A2 | 5/2007 |
| WO | WO 2007/110619 A1 | 10/2007 |
| WO | WO 07/137144 A2 | 11/2007 |
| WO | WO 08/002661 A2 | 1/2008 |

(56) References Cited

FOREIGN PATENT DOCUMENTS

| WO | WO 08/002663 A2 | 1/2008 |
|---|---|---|
| WO | WO 08/002673 A2 | 1/2008 |
| WO | WO 08/066583 A2 | 6/2008 |
| WO | WO 08/088884 A2 | 7/2008 |
| WO | WO 08/094546 A2 | 8/2008 |
| WO | WO 10/046713 A2 | 4/2010 |
| WO | WO 10/074760 A1 | 7/2010 |
| WO | WO 10/077806 A1 | 7/2010 |
| WO | WO 11/017560 A1 | 2/2011 |
| WO | WO 11/072287 A2 | 6/2011 |
| WO | WO 2011/140516 A2 | 11/2011 |
| WO | WO 2012/030980 A1 | 3/2012 |
| WO | WO 2012/135902 A1 | 10/2012 |
| WO | WO 2014/151190 A1 | 9/2014 |
| WO | WO 2014/197655 A1 | 12/2014 |
| WO | WO 2014/197702 A1 | 12/2014 |
| WO | WO 2015/021058 A2 | 2/2015 |
| WO | WO 2016/160936 A1 | 10/2016 |
| WO | WO 2017/176963 A1 | 10/2017 |
| WO | WO 2018/126287 A1 | 7/2018 |

OTHER PUBLICATIONS

Extended European Search Report for EP 17163812.5 dated Jul. 12, 2017.
International Search Report and Written Opinion for PCT/US2011/049997 dated Dec. 13, 2011.
International Preliminary Report on Patentability for PCT/US2011/049997 dated Mar. 14, 2013.
Extended European Search Report for EP 09836804.6 dated Jun. 4, 2012.
International Search Report and Written Opinion for PCT/US2009/067841 dated Mar. 22, 2010.
International Preliminary Report on Patentability for PCT/US2009/067841 dated Jun. 30, 2011.
Extended European Search Report for EP09835395.6 dated Mar. 16, 2016.
International Search Report and Written Opinion for PCT/US2009/006704 dated Mar. 3, 2010.
International Preliminary Report on Patentabilityfor PCT/US2009/006704 dated Jul. 7, 2011.
Invitation to Pay Additional Fees for PCT/US2013/077238 dated Mar. 18, 2014.
International Search Report and Written Opinion for PCT/US2013/077238 dated May 19, 2014.
International Preliminary Report on Patentability for PCT/US2013/077238 dated Jul. 2, 2015.
Invitation to Pay Additional Fees for PCT/US2014/049805, dated Nov. 14, 2014.
International Search Report for PCT/US2014/049805, dated Feb. 16, 2015.
International Preliminary Report on Patentability for PCT/US2014/049805, dated Feb. 18, 2016.
Extended European Search Report for EP 14807322.4, dated Jan. 2, 2017.
International Search Report and Written Opinion for PCT/US2014/041009, dated Sep. 10, 2014.
International Preliminary Report on Patentability for PCT/US2014/041009, dated Dec. 17, 2015.
Invitation to Pay Additional Fees for PCT/US2016/023173, dated Jul. 8, 2016.
International Search Report and Written Opinion for PCT/US2016/023173, dated Sep. 16, 2016.
International Preliminary Report on Patentability for PCT/US2016/023173, dated Sep. 28, 2017.
International Search Report and Written Opinion for PCT/US2016/024937, dated Sep. 9, 2016.
Invitation to Pay Additional Fees for PCT/US2017/026285, dated Jul. 6, 2017.
International Search Report and Written Opinion for PCT/US2017/026285, dated Aug. 28, 2017.
Genbank Accession No. AAC43119. Sep. 3, 1993. 4 pages. Last accessed Jul. 26, 2016.
Genbank Submission; NIH/NCBI, Accession No. AAB59985; Ling et al.; Nov. 24, 1994.
Genbank Submission; NIH/NCBI, Accession No. AAC73225; Blattner et al.; Sep. 1, 2011.
Genbank Submission; NIH/NCBI, Accession No. AAC73226; Blattner et al.; Sep. 1, 2011.
Genbank Submission; NIH/NCBI, Accession No. AAC73296; Blattner et al.; Sep. 1, 2011.
Genbank Submission; NIH/NCBI, Accession No. AAC73346; Blattner et al.; Sep. 1, 2011.
Genbank Submission; NIH/NCBI, Accession No. AAC73347; Blattner et al.; Sep. 1, 2011.
Genbank Submission; NIH/NCBI, Accession No. AAC73842; Blattner et al.; Sep. 1, 2011.
Genbank Submission; NIH/NCBI, Accession No. AAC73957; Blattner et al.; Sep. 1, 2011.
Genbank Submission; NIH/NCBI, Accession No. AAC74746; Blattner et al.; Sep. 1, 2011.
Genbank Submission; NIH/NCBI, Accession No. AAC74849; Blattner et al.; Sep. 1, 2011.
Genbank Submission; NIH/NCBI, Accession No. AAC74924; Blattner et al.; Sep. 1, 2011.
Genbank Submission; NIH/NCBI, Accession No. AAC75447; Blattner et al.; Sep. 1, 2011.
Genbank Submission; NIH/NCBI, Accession No. AAC75821; Blattner et al.; Sep. 1, 2011.
Genbank Submission; NIH/NCBI, Accession No. AAC75962; Blattner et al.; Sep. 1, 2011.
Genbank Submission; NIH/NCBI, Accession No. AAC75963; Blattner et al.; Sep. 1, 2011.
Genbank Submission; NIH/NCBI, Accession No. AAC76849; Blattner et al.; Sep. 1, 2011.
Genbank Submission; NIH/NCBI, Accession No. AAC76898; Blattner et al.; Sep. 1, 2011.
Genbank Submission; NIH/NCBI, Accession No. AAC76901; Blattner et al.; Sep. 1, 2011.
Genbank Submission; NIH/NCBI, Accession No. AAC76995; Blattner et al.; Sep. 1, 2011.
Genbank Submission; NIH/NCBI, Accession No. AAD38229; McGowan et al.; Jul. 14, 1999.
Genbank Submission; NIH/NCBI, Accession No. AAD38230; McGowan et al.; Jul. 14, 1999.
Genbank Submission; NIH/NCBI, Accession No. AAD38231; McGowan et al.; Jul. 14, 1999.
Genbank Submission; NIH/NCBI, Accession No. ABA79923; Copeland et al.; Nov. 21, 2011.
Genbank Submission; NIH/NCBI, Accession No. ACJ71669; Erb et al.; Dec. 10, 2008.
Genbank Submission; NIH/NCBI, Accession No. AEW99093; Ou et al.; Dec. 29, 2011.
Genbank Submission; NIH/NCBI, Accession No. AEW99097; Ou et al.; Dec. 29, 2011.
Genbank Submission; NIH/NCBI, Accession No. AEW99098; Ou et al.; Dec. 29, 2011.
Genbank Submission; NIH/NCBI, Accession No. BAA22406; Mori et al.; Sep. 20, 1997.
Genbank Submission; NIH/NCBI, Accession No. BAB67276; Kawarabayasi et al.; Aug. 17, 2011.
Genbank Submission; NIH/NCBI, Accession No. CAD18973; Nunez et al.; Apr. 15, 2005.
Genbank Submission; NIH/NCBI, Accession No. CAD18975; Nunez et al.; Apr. 15, 2005.
Genbank Submission; NIH/NCBI, Accession No. CAD18981; Nunez et al.; Apr. 15, 2005.
Genbank Submission; NIH/NCBI, Accession No. CAD18985; Nunez et al.; Apr. 15, 2005.
Genbank Submission; NIH/NCBI, Accession No. CAD18990; Nunez et al.; Apr. 15, 2005.

(56) References Cited

OTHER PUBLICATIONS

UniProtKB/Swiss-Prot; Accession No. P28269; Yonaha et al.; Jul. 11, 2012.
[No Author Listed] Biapenem. Drugs Fut. 1994;19(7):631-637.
[No Author Listed] Biolistic® Particle Delivery System Bibliography. Bio-Rad Technical Bulletin #1687. Bio-Rad Laboratories. 12 pages.
[No Author Listed] Crude Lysate. Wikipedia entry for Crude Lysate, http://en.wikipedia.org/wiki/Crude_lysate downloaded on Mar. 3, 2015. Page Last Modified on Nov. 3, 2013. 1 page.
Adams et al., Hindered dialkylamino nucleoside phosphite reagents in the synthesis of two DNA 51-mers. J Am Chem Soc. 1983;105(3):661-3.
Alber et al., Malonyl-coenzyme A reductase in the modified 3-hydroxypropionate cycle for autotrophic carbon fixation in archaeal *Metallosphaera and Sulfolobus* spp. J Bacteriol. Dec. 2006;188(24):8551-9. Epub Oct. 13, 2006.
Allain, Cell-free ethanol production: the future of fuel ethanol? J Chem Technol Biotechnol. 2007;82:117-20.
Alper et al., Tuning genetic control through promoter engineering. Proc Natl Acad Sci U S A. Sep. 6, 2005;102(36):12678-83. Epub Aug. 25, 2005.
Alves-Pereira et al., CDP-alcohol hydrolase, a very efficient activity of the 5'-nucleotidase/udp-sugar hydrolase encoded by the usha gene of yersinia intermedia and *Escherichia coli*. J Bacteriol. Sep. 15, 2008;190(18):6153-61. Published ahead of print Jul. 18, 2008, doi:10.1128/JB.00658-08.
Anthony et al., Optimization of the mevalonate-based isoprenoid biosynthetic pathway in *Escherichia coli* for production of the anti-malarial drug precursor amorpha-4,11-diene. Metab Eng. Jan. 2009;11(1):13-9. Epub Aug. 12, 2008.
Atsumi et al., Metabolic engineering of *Escherichia coli* for 1-butanol production. Metab Eng. Nov. 2008;10(6):305-11. Epub Sep. 14, 2007.
Atsumi et al., Non-fermentative pathways for synthesis of branched-chain higher alcohols as biofuels. Nature. Jan. 3, 2008;451(7174):86-9.
Baba et al., Construction of *Escherichia coli* K-12 in-frame, single-gene knockout mutants: the Keio collection. Mol Syst Biol. 2006;2:2006. 0008. Epub Feb. 21, 2006.
Bateson et al., Olivanic acid analogues. Part 6. Biomimetic synthesis of (±)-PS-5, (±)-6-Epi-PS-5, and (±)-benzyl MM22381. J Chem Soc Perkin Trans 1. 1990;1793-1801.
Baum et al., beta-Galactosidase containing a human immunodeficiency virus protease cleavage site is cleaved and inactivated by human immunodeficiency virus protease. Proc Natl Acad Sci U S A. Dec. 1990;87(24):10023-7.
Beaucage et al., Deoxynucleoside phosphoramidites—A new class of key intermediates for deoxypolynucleotide synthesis. Tetra Lett. 1981;22(20):1859-62.
Belousov et al., Sequence-specific targeting and covalent modification of human genomic DNA. Nucleic Acids Res. Sep. 1, 1997;25(17):3440-4.
Benton et al., Screening lambdagt recombinant clones by hybridization to single plaques in situ. Science. Apr. 8, 1977;196(4286):180-2.
Berge et al., Pharmaceutical salts. J Pharmaceut Sci. Jan. 1977;66(1):1-19.
Blattner et al., Analysis of the *Escherichia coli* genome. IV. DNA sequence of the region from 89.2 to 92.8 minutes. Nucleic Acids Res. Nov. 25, 1993;21(23):5408-17.
Blommers et al., Effects of the introduction of L-nucleotides into DNA. Solution structure of the heterochiral duplex d(G-C-G-(L)T-G-C-G).d(C-G-C-A-C-G-C) studied by NMR spectroscopy. Biochemistry. Jun. 28, 1994;33(25):7886-96.
Bodner et al., Definition of the common and divergent steps in carbapenem β-lactam antibiotic biosynthesis. Chembiochem. Sep. 19, 2011;12(14):2159-65. doi: 10.1002/cbic.201100366. Epub Aug. 24, 2011.

Bodner et al., Non-heme iron oxygenases generate natural structural diversity in carbapenem antibiotics. J Am Chem Soc. Jan. 13, 2010;132(1):12-3.
Boiteux et al., Design of glycolysis. Philos Trans R Soc Lond B Biol Sci. Jun. 26, 1981;293(1063):5-22.
Bongaerts et al., Metabolic engineering for microbial production of aromatic amino acids and derived compounds. Metab Eng. Oct. 2001;3(4):289-300.
Boyer et al., Cell-free synthesis and maturation of [FeFe] hydrogenases. Biotechnol Bioeng. Jan. 1, 2008;99(1):59-67.
Bradley, Star role for bacteria in controlling flu pandemic? Nat Rev Drug Discov. Dec. 2005;4(12):945-6.
Brady et al., Transfer of Pantoea citrea, Pantoea punctata and Pantoea terrea to the genus *Tatumella emend.* as *Tatumella citrea* comb. nov., *Tatumella punctata* comb. nov. and *Tatumella terrea* comb. nov. and description of *Tatumella morbirosei* sp. nov. Int J Syst Evol Microbiol. Mar. 2010;60(Pt 3):484-94. doi: 10.1099/ijs. 0.012070-0. Epub Aug. 4, 2009.
Brown et al., Chemical synthesis and cloning of a tyrosine tRNA gene. Methods Enzymol. 1979;68:109-51.
Buist et al., Different subcellular locations of secretome components of Gram-positive bacteria. Microbiology. Oct. 2006;152(Pt 10):2867-74.
Bujara et al., Exploiting cell-free systems: Implementation and debugging of a system of biotransformations. Biotechnol Bioeng. Jun. 15, 2010;106(3):376-89. doi: 10.1002/bit.22666.
Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.
Calhoun et al., An economical method for cell-free protein synthesis using glucose and nucleoside monophosphates. Biotechnol Prog. Jul.-Aug. 2005;21(4):1146-53.
Calhoun et al., Energizing cell-free protein synthesis with glucose metabolism. Biotechnol Bioeng. Jun. 5, 2005;90(5):606-13.
Calhoun et al., Energy systems for ATP regeneration in cell-free protein synthesis reactions. Methods in Molecular Biology. In vitro transcription and translation protocols. 2007;375(2):3-17.
Calhoun et al., Total amino acid stabilization during cell-free protein synthesis reactions. J Biotechnol. May 17, 2006;123(2):193-203. Epub Jan. 26, 2006.
Campbell et al., The CTP:phosphocholine cytidylyltransferase encoded by the licC gene of *Streptococcus pneumoniae*: cloning, expression, purification, and characterization. Biochim Biophys Acta. Dec. 30, 2001;1534(2-3):85-95.
Chandran et al., Phosphoenolpyruvate availability and the biosynthesis of shikimic acid. Biotechnol Prog. May-Jun. 2003;19(3):808-14.
Chang et al., YPA: an integrated repository of promoter features in *Saccharomyces cerevisiae*. Nucleic Acids Res. Jan. 2011;39(Database issue):D647-52. Epub Nov. 2, 2010.
Chen et al., A modified osmotic shock for periplasmic release of a recombinant creatinase from *Escherichia coli*. Biochem Eng J. 2004;19:211-5.
Chen et al., Crystal structures of penicillin-binding protein 6 from *Escherichia coli*. J Am Chem Soc. Oct. 14, 2009;131(40):14345-54.
Chen et al., High-level accumulation of a recombinant antibody fragment in the periplasm of *Escherichia coli* requires a triple-mutant (degP prc spr) host strain. Biotechnol Bioeng. Mar. 5, 2004;85(5):463-74.
Cheng et al., Purification and characterization of the *Escherichia coli* exoribonuclease RNase R. Comparison with RNase II. J Biol Chem. Jun. 14, 2002;277(24):21624-9. Epub Apr. 10, 2002.
Chisti et al., Disruption of microbial cells for intracellular products. Enzyme Micro Technol 1986;8(4):194-204. doi 10.1016/0141-0229(86)90087-6.
Chiu et al., Site-directed, Ligase-Independent Mutagenesis (SLIM): a single-tube methodology approaching 100% efficiency in 4 h. Nucleic Acids Res. Dec. 7, 2004;32(21):e174.
Chong et al., Single-column purification of free recombinant proteins using a self-cleavable affinity tag derived from a protein splicing element. Gene. Jun. 19, 1997;192(2):271-81.

(56) References Cited

OTHER PUBLICATIONS

Choubey et al., Molecular characterization and localization of Plasmodium falciparum choline kinase. Biochim Biophys Acta. Jul. 2006;1760(7):1027-38.
Collins-Racie et al., Production of recombinant bovine enterokinase catalytic subunit in *Escherichia coli* using the novel secretory fusion partner DsbA. Biotechnology (N Y). Sep. 1995;13(9):982-7.
Coulthurst et al., Regulation and biosynthesis of carbapenem antibiotics in bacteria. Nat Rev Microbiol. Apr. 2005;3(4):295-306. Erratum included.
Dahiyat et al., De novo protein design: fully automated sequence selection. Science. Oct. 3, 1997;278(5335):82-7.
Dahl et al., Isolation and characterization of Chinese hamster ovary cells defective in the intracellular metabolism of low density lipoprotein-derived cholesterol. J Biol Chem. Mar. 5, 1992;267(7):4889-96.
Danese et al., Targeting and assembly of periplasmic and outer-membrane proteins in *Escherichia coli*. Annu Rev Genet. 1998;32:59-94.
Dani et al., Isolation and characterization of a thylakoid membrane module showing partial light and dark reactions. Biochim Biophys Acta. May 15, 2005;1669(1):43-52.
Daniell et al., Transformation of the cyanobacterium Anacystis nidulans 6301 with the *Escherichia coli* plasmid pBR322. Proc Natl Acad Sci U S A. Apr. 1986;83(8):2546-50.
Datsenko et al., One-step inactivation of chromosomal genes in *Escherichia coli* K-12 using PCR products. Proc Natl Acad Sci U S A. Jun. 6, 2000;97(12):6640-5.
Daube et al., Cell-free co-synthesis of protein nanoassemblies: tubes, rings, and doughnuts. Nano Lett. Mar. 2007;7(3):638-41. Epub Feb. 2, 2007.
De Boer et al., Protein targeting towards the thylakoid lumen of chloroplasts: proper localization of fusion proteins is only observed in vivo. EMBO J. Oct. 1991;10(10):2765-72.
De Mey et al., Construction and model-based analysis of a promoter library for *E. coli*: an indispensable tool for metabolic engineering. BMC Biotechnol. Jun. 18, 2007;7:34.
De Vries et al., Cloning, expression, and sequence analysis of the Bacillus methanolicus C1 methanol dehydrogenase gene. J Bacteriol. Aug. 1992;174(16):5346-53.
Dietrich et al., A novel semi-biosynthetic route for artemisinin production using engineered substrate-promiscuous P450(BM3). ACS Chem Biol. Apr. 17, 2009;4(4):261-7.
Ding et al., Functional analysis of the essential bifunctional tobacco enzyme 3-dehydroquinate dehydratase/shikimate dehydrogenase in transgenic tobacco plants. J Exp Bot. 2007;58(8):2053-67. Epub Apr. 26, 2007.
Dingwall et al., The nucleoplasmin nuclear location sequence is larger and more complex than that of SV-40 large T antigen. J Cell Biol. Sep. 1988;107(3):841-9.
Draper et al., Ti plasmid homologous sequences present in tissues from agrobacterium plasmid-transformed petunia protoplasts. Plant Cell Physiol. 1982;23(3):451-8.
Egan et al., Transketolase kinetics. The slow reconstitution of the holoenzyme is due to rate-limiting dimerization of the subunits. J Biol Chem. May 25, 1981;256(10):4877-83.
Ehrmann et al., TnTIN and TnTAP: mini-transposons for site-specific proteolysis in vivo. Proc Natl Acad Sci U S A. Nov. 25, 1997;94(24):13111-5.
Elander, Industrial production of beta-lactam antibiotics. Appl Microbiol Biotechnol. Jun. 2003;61(5-6):385-92. Epub Apr. 3, 2003.
Ellermeier et al., Construction of targeted single copy lac fusions using lambda Red and FLP-mediated site-specific recombination in bacteria. Gene. May 15, 2002;290(1-2):153-61.
Endoh et al., Cell-free protein synthesis at high temperatures using the lysate of a hyperthermophile. J Biotechnol. Nov. 1, 2006;126(2):186-95. Epub May 30, 2006.
Erb et al., Carboxylation mechanism and stereochemistry of crotonyl-CoA carboxylase/reductase, a carboxylating enoyl-thioester reductase. Proc Natl Acad Sci U S A. Jun. 2, 2009;106(22):8871-6. Epub May 20, 2009.
Erb et al., Synthesis of C5-dicarboxylic acids from C2-units involving crotonyl-CoA carboxylase/reductase: The ethylmalonyl-CoA pathway. Proc Nat Acad Sci. Jun. 4, 2007;104(25):10631-6.
Eser et al.,Target-directed proteolysis in vivo. Methods Enzymol. 2007;421:68-83.
Evans et al., The asymmetric synthesis of β-lactam antibiotics—IV. A formal synthesis of thienamycin. Tetra Lett. 1986;27(41):4961-4.
Fischer et al., Metabolic flux profiling of *Escherichia coli* mutants in central carbon metabolism using GC-MS. Eur J Biochem. Mar. 2003;270(5):880-91.
Flores et al., Pathway engineering for the production of aromatic compounds in *Escherichia coli*. Nat Biotechnol. May 1996;14(5):620-3.
Flores et al., Analysis of carbon metabolism in *Escherichia coli* strains with an inactive phosphotransferase system by (13)C labeling and NMR spectroscopy. Metab Eng. Apr. 2002;4(2):124-37.
Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.
Fox et al., Methane monooxygenase from Methylosinus trichosporium OB3b. Purification and properties of a three-component system with high specific activity from a type II methanotroph. J Biol Chem. Jun. 15, 1989;264(17):10023-33.
Fradejas et al., The control of shikimic acid synthesis by tyrosine and phenylalamine. Biochem Biophys Res Commun. Jul. 26, 1961;5:320-3.
Freeman et al., Four enzymes define the incorporation of coenzyme A in thienamycin biosynthesis. Proc Natl Acad Sci U S A. Aug. 12, 20082;105(32):11128-33. Epub Aug. 4, 2008. Supplemental material included.
Freeman et al., A comparison of methods for plasmid delivery into plant protoplasts. Plant Cell Physiol. 1984;25(8):1353-65.
Frenkel et al., 7,12-dimethylbenz[a]anthracene induces oxidative DNA modification in vivo. Free Radic Biol Med. Sep. 1995;19(3):373-80.
Friesen et al., Purification and Kinetic Characterization of CTP-:Phosphocholine Cytidylyltransferase from *Saccharomyces cerevisiae*. Protein Expression and Purification. Feb. 2001;21(1):141-8.
Fujio et al., Construction of a plasmid carrying both CTP synthetase and a fused gene formed from cholinephosphate cytidylyltransferase and choline kinase genes and its application to industrial CDP-choline production: enzymatic production of CDP-choline from orotic acid (Part II). Biosci Biotechnol Biochem. Jun. 1997;61(6):960-4.
Fujio et al., Production of ATP from Adenine by Brevibacterium ammoniagenes, J Ferment Technol. 1983;61(3):261-267.
Gaspar et al., High yields of 2,3-butanediol and mannitol in Lactococcus lactis through engineering of $NAD^+$ cofactor recycling. Appl Environ Microbiol. Oct. 2011;77(19):6826-35. Epub Aug. 12, 2011. Supplemental material included.
Ger et al., A single Ser-180 mutation desensitizes feedback inhibition of the phenylalanine-sensitive3-deoxy-D-arabino-heptulosonate 7-phosphate (DAHP) synthetase in *Escherichia coli*. J Biochem. Nov. 1994;116(5):986-90.
Gibellini et al., Biochemical characterization of the initial steps of the Kennedy pathway in Trypanosoma brucei: the ethanolamine and choline kinases. Biochem J. 2008;415:135-44. Supplemental material included.
Goerke et al., Cell-free metabolic engineering promotes high-level production of bioactive Gaussia princeps luciferase.Metab Eng. May-Jul. 2008;10(3-4):187-200. doi: 10.1016/j.ymben.2008.04.001. Epub May 2, 2008.
Goerke et al., Development of cell-free protein synthesis platforms for disulfide bonded proteins. Biotechnol Bioeng. Feb. 1, 2008;99(2):351-67. Epub Jul. 11, 2007.
Goody, A simple and rapid method for the synthesis of nucleoside 5'-monophosphates enriched with 17O or 18O on the phosphate group. Anal Biochem. Jan. 15, 1982;119(2):322-4.

(56) References Cited

OTHER PUBLICATIONS

Gordon-Kamm et al., Transformation of Maize Cells and Regeneration of Fertile Transgenic Plants. Plant Cell. Jul. 1990;2(7):603-618.
Gosset et al., A direct comparison of approaches for increasing carbon flow to aromatic biosynthesis in *Escherichia coli*. J Ind Microbiol. Jul. 1996;17(1):47-52.
Grabowski, Enantiopure drug synthesis: from methyldopa to imipenem to efavirenz. Chirality. 2005;17 Suppl:S249-59.
Grieco et al., β-Lactam antibiotics: a formal stereocontrolled total synthesis of (.+-.)-thienamycin. J Am Chem Soc. 1984;106(21):6414-7.
Grunstein et al., Colony hybridization: a method for the isolation of cloned DNAs that contain a specific gene. Proc Natl Acad Sci U S A. Oct. 1975;72(10):3961-5.
Hamed et al., Carboxymethylproline synthase catalysed syntheses of functionalized N-heterocycles. Chem Commun (Camb). Mar. 7, 2010;46(9):1413-5. Epub Jan. 12, 2010.
Hamed et al., Crotonase catalysis enables flexible production of functionalized prolines and carbapenams. J Am Chem Soc. Jan. 11, 2012;134(1):471-9. doi: 10.1021/ja208318d. Epub Dec. 14, 2011.
Hamed et al., Evidence that thienamycin biosynthesis proceeds via C-5 epimerization: I catalyzes the formation of (2S,5S)-trans-carboxymethylproline. Chembiochem. Jan. 26, 2009;10(2):246-50.
Hamed et al., The enzymes of β-lactam biosynthesis. Nat Prod Rep. Jan. 2013;30(1):21-107. doi: 10.1039/c2np20065a.
Han et al., Paraffin oil as a "methane vector" for rapid and high cell density cultivation of Methylosinus trichosporium OB3b. Appl Microbiol Biotechnol. Jun. 2009;83(4):669-77. doi: 10.1007/s00253-009-1866-2. Epub Feb. 12, 2009.
Hawley et al., Compilation and analysis of *Escherichia coli* promoter DNA sequences. Nucleic Acids Res. Apr. 25, 1983;11(8):2237-55.
Herrmann, The shikimate pathway as an entry to aromatic secondary metabolism. Plant Physiol. Jan. 1995;107(1):7-12.
Hethke et al., Cell-free transcription at 95 degrees: thermostability of transcriptional components and DNA topology requirements of Pyrococcus transcription. Genetics. Aug. 1999;152(4):1325-33.
Hikita et al., Effects of total hydrophobicity and length of the hydrophobic domain of a signal peptide on in vitro translocation efficiency. J Biol Chem. 1992;267:4882-8.
Hikita et al., The requirement of a positive charge at the amino terminus can be compensated for by a longer central hydrophobic stretch in the functioning of signal peptides. J Biol Chem. 1992;267:12375-9.
Hodgson et al., π-Allyltricarbonyliron lactone complexes in synthesis: application to the synthesis of the β-lactam antibiotic (+)-thienamycin. J Chem Soc Chem Comm. 1984;8:494-6.
Horak et al., Two distinct proteolytic systems responsible for glucose-induced degradation of fructose-1,6-bisphosphatase and the Gal2p transporter in the yeast *Saccharomyces cerevisiae* share the same protein components of the glucose signaling pathway. J Biol Chem. Mar. 8, 2002;277(10):8248-54. Epub Dec. 28, 2001.
Hryniewicz et al., Sulfate and thiosulfate transport in *Escherichia coli* K-12: identification of a gene encoding a novel protein involved in thiosulfate binding. J Bacteriol. Jun. 1990;172(6):3358-66.
Inouye, The discovery of mRNA interferases: implication in bacterial physiology and application to biotechnology. J Cell Physiol. Dec. 2006;209(3):670-6.
Ishii et al., DBTBS: a database of Bacillus subtilis promoters and transcription factors. Nucleic Acids Res. Jan. 1, 2001;29(1):278-80.
Jacobi et al., Formal Total Syntheses of the β-Lactam Antibiotics Thienamycin and PS-5. J Org Chem. 1996;61(7):2413-27.
Jang et al., Sugar sensing in higher plants. Plant Cell. Nov. 1994;6(11):1665-79.
Jenny et al., A critical review of the methods for cleavage of fusion proteins with thrombin and factor Xa. Protein Expr Purif. Sep. 2003;31(1):1-11.
Jermutus et al., Recent advances in producing and selecting functional proteins by using cell-free translation. Curr Opin Biotechnol. Oct. 1998;9(5):534-48.
Jewett et al., An integrated cell-free metabolic platform for protein production and synthetic biology. Mol Syst Biol. 2008;4:220. Epub Oct. 14, 2008.
Jewett et al., Mimicking the *Escherichia coli* cytoplasmic environment activates long-lived and efficient cell-free protein synthesis. Biotechnol Bioeng. Apr. 5, 2004;86(1):19-26.
Jonnalagadda et al., Flux regulation in glycogen-induced oscillatory glycolysis in cell-free extracts of *Saccharomyces carlsbergensis*. Biosystems. 1982;15(1):49-58.
Kahan et al., Thienamycin, a new beta-lactam antibiotic. I. Discovery, taxonomy, isolation and physical properties. J Antibiot (Tokyo). Jan. 1979;32(1):1-12.
Kahan et al., Thienamycin: development of imipenen-cilastatin. J Antimicrob Chemother. Dec. 1983;12 Suppl D:1-35.
Kalderon et al., A short amino acid sequence able to specify nuclear location. Cell. Dec. 1984;39(3 Pt 2):499-509.
Kametani et al., Studies on the syntheses of heterocyclic compounds. 800. A formal total synthesis of (.+-.)-thienamycin and a (.+-.)-decysteaminylthienamycin derivative. J Am Chem Soc. 1980;102(6):2060-5.
Kang et al., Enhanced biodegradation of toxic organophosphate compounds using recombinant *Escherichia coli* with sec pathway-driven periplasmic secretion of organophosphorus hydrolase. Biotechnol Prog. Mar.-Apr. 2006;22(2):406-10.
Kapust et al., Tobacco etch virus protease: mechanism of autolysis and rational design of stable mutants with wild-type catalytic proficiency. Protein Eng. Dec. 2001;14(12):993-1000.
Kawarasaki et al., Prolonged cell-free protein synthesis in a batch system using wheat germ extract.Biosci Biotechnol Biochem. Oct. 1994;58(10):1911-3.
Kern et al., Engineering primary metabolic pathways of industrial micro-organisms. J Biotechnol. Mar. 30, 2007;129(1):6-29. Epub Dec. 2, 2006.
Kikuchi et al., Mutational analysis of the feedback sites of phenylalanine-sensitive 3-deoxy-D-arabino-heptulosonate-7-phosphate synthase of *Escherichia coli*. Appl Environ Microbiol. Feb. 1997;63(2):761-2.
Kim et al., Expression, purification, and characterization of choline kinase, product of the cki gene from *Saccharomyces cerevisiae*. J Bio Chem. 1998;273(12):6844-6852.
Kim et al., Metabolic flux analysis for calcium dependent antibiotic (CDA) production in *Streptomyces coelicolor*. Metab Eng. Oct. 2004;6(4):313-25.
Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.
Kim et al., Regeneration of adenosine triphosphate from glycolytic intermediates for cell-free protein synthesis.Biotechnol Bioeng. Aug. 20, 2001;74(4):309-16.
Kimmel, Identification and characterization of specific clones: strategy for confirming the validity of presumptive clones. Methods Enzymol. 1987;152:507-11.
Kindle, High-frequency nuclear transformation of Chlamydomonas reinhardtii. Proc Natl Acad Sci U S A. Feb. 1990;87(3):1228-32.
Klemme, Photoproduction of hydrogen by purple bacteria: A critical evaluation of the rate limiting enzymatic steps. J Bioscience 1993;48 482-87.
Klimov et al., New phelonic inhibitors of electron transfer in photosystem II. Biologichesksie Membrany. 1992;9(6):565-575.
Knapp et al., Cell-free production of active *E. coli* thioredoxin reductase and glutathione reductase. FEBS Lett. Feb. 13, 2004;559(1-3):66-70.
Knop et al., Hydroaromatic equilibration during biosynthesis of shikimic acid. J Am Chem Soc. Oct. 24, 2001;123(42):10173-82.
Ko et al., Targeting of proteins to the thylakoid lumen by the bipartite transit peptide of the 33 kd oxygen-evolving protein. EMBO J. Nov. 1989;8(11):3187-94.
Krämer et al., Metabolic engineering for microbial production of shikimic acid. Metab Eng. Oct. 2003;5(4):277-83.

(56) References Cited

OTHER PUBLICATIONS

Krell et al., Crystallization and preliminary X-ray crystallographic analysis of shikimate kinase from Erwinia chrysanthemi. Acta Crystallogr D Biol Crystallogr. Sep. 1, 1997;53(Pt 5):612-4.
Krutsakorn et al., In vitro production of n-butanol from glucose. Metab Eng. Nov. 2013;20:84-91. doi: 10.1016/j.ymben.2013.09.006. Epub Sep. 19, 2013.
Kumagai et al., Current status of oral carbapenem development. Curr Med Chem—Anti-Infective Agents. Jan. 2002;1(1):1-14.
Kunkel, Rapid and efficient site-specific mutagenesis without phenotypic selection. Proc Natl Acad Sci U S A. Jan. 1985;82(2):488-92.
Lee et al., Fermentative production of thymidine by a metabolically engineered Escherichia coli strain. Appl Environ Microbiol. Apr. 2009;75(8):2423-32. Epub Feb. 27, 2009.
Lee et al., Systems metabolic engineering of Escherichia coli for L-threonine production. Mol Syst Biol. 2007;3:149. Epub Dec. 4, 2007.
Lee, High cell-density culture of Escherichia coli. Trends Biotechnol. Mar. 1996;14(3):98-105.
Li et al., Improved cell-free RNA and protein synthesis system. PLoS One. Sep. 2, 2014;9(9):e106232. doi: 10.1371/journal.pone.0106232. eCollection 2014.
Li et al., Rational strain improvement for enhanced clavulanic acid production by genetic engineering of the glycolytic pathway in Streptomyces clavuligerus. Metab Eng. May 2006;8(3):240-52. Epub Mar. 10, 2006.
Liu et al., Combined biosynthetic pathway for de novo production of UDP-galactose: catalysis with multiple enzymes immobilized on agarose beads. Chembiochem. Apr. 2, 2002;3(4):348-55.
Liu et al., Streamlining Escherichia coli S30 extract preparation for economical cell-free protein synthesis. Biotechnol Prog. Mar.-Apr. 2005;21(2):460-5.
Ludwig et al., Mutations affecting export and activity of cytolysin A from Escherichia coli. J Bacteriol. Aug. 2010;192(15):4001-11. Epub May 28, 2010.
Luli et al., Comparison of growth, acetate production, and acetate inhibition of Escherichia coli strains in batch and fed-batch fermentations. Appl Environ Microbiol. Apr. 1990;56(4):1004-11.
Mackle et al., Role of signal peptides in targeting of proteins in cyanobacteria. J Bacteriol. Apr. 1994;176(7):1857-64.
Mandel et al., Modular synthesis of pantetheine and phosphopantetheine. Org Lett. Dec. 23, 2004;6(26):4801-3.
Martin et al., Engineering a mevalonate pathway in Escherichia coli for production of terpenoids. Nat Biotechnol. Jul. 2003;21(7):796-802. Epub Jun. 1, 2003.
Mayes, Metabolism of Glycogen. In: Harper's Biochemistry—a LANGE medical book. 1990. Twenty-second edition. Murray et al., Eds. Chapter 20: 171-178.
Mergulhão et al., Analysis of factors affecting the periplasmic production of recombinant proteins in Escherichia coli. J Microbiol Biotechnol. Aug. 2007;17(8):1236-41.
Mergulhão et al., Recombinant protein secretion in Escherichia coli. Biotechnol Adv. May 2005;23(3):177-202. Epub Jan. 8, 2005.
Meyerhof, New investigations in the kinetics of cell free alcoholic fermentation. Antonie Van Leeuwenhoek. Jan.-Apr. 1947;12(1-4):140-4.
Meynial-Salles et al., New tool for metabolic pathway engineering in Escherichia coli: one-step method to modulate expression of chromosomal genes. Appl Environ Microbiol. Apr. 2005;71(4):2140-4.
Michel-Reydellet et al., Amino acid stabilization for cell-free protein synthesis by modification of the Escherichia coli genome. Metab Eng. Jul. 2004;6(3):197-203.
Muchmore et al., Crystal structure of glutamine phosphoribosylpyrophosphate amidotransferase from Escherichia coli. Protein Sci. Jan. 1998;7(1):39-51.
Muktiono et al., Isolation and purification assay of ex vivo photosystem II D1 protein toward integrated biointeraction analysis. Anal Bioanal Chem. Feb. 2008;390(4):1195-202. Epub Jan. 3, 2008.

Murphy, Use of bacteriophage lambda recombination functions to promote gene replacement in Escherichia coli. J Bacteriol. Apr. 1998;180(8):2063-71.
Myers et al., Determination of imipenem and cilastatin in serum by high-pressure liquid chromatography. Antimicrob Agents Chemother. Jul. 1984;26(1):78-81.
Narang et al., Improved phosphotriester method for the synthesis of gene fragments. Methods Enzymol. 1979;68:90-8.
Neidhardt et al., Culture medium for enterobacteria. J Bacteriol. Sep. 1974;119(3):736-47.
Nilsen, Selective precipitation of large RNAs. Cold Spring Harb Protoc. Dec. 1, 2012;2012(12). pii: pdb.prot072322. doi: 10.1101/pdb.prot072322.
Ninh et al., Assembly and multiple gene expression of thermophilic enzymes in Escherichia coli for in vitro metabolic engineering. Biotechnol Bioeng. Jul. 26, 2014. doi: 10.1002/bit.25338.
Niu et al., Benzene-free synthesis of adipic acid. Biotechnol Prog. Mar.-Apr. 2002;18(2):201-11.
Noireaux et al., Principles of cell-free genetic circuit assembly. Proc Natl Acad Sci U S A. Oct. 28, 2003;100(22):12672-7. Epub Oct. 14, 2003.
Nunez et al., The Biosynthetic Gene Cluster for the β-Lactam Carbapenem Thienamycin in Streptomyces cattleya. Chem Biol. Apr. 2003;10(4):301-11.
Ono et al., Photosynthetic electron transport and phosphorylation reactions in thylakoid membranes from the blue-green alga Anacystis nidulans. Biochim Biophys Acta. Jun. 8, 1978;502(3):477-85.
Pace et al., Photosynthetic regeneration of ATP using bacterial chromatophores. Biotechnol Bioeng. Oct. 1976;18(10):1413-23.
Park et al., Metal-catalyzed oxidation of phenylalanine-sensitive 3-deoxy-D-arabino heptulosonate-7-phosphate synthase from Escherichia coli: inactivation and destabilization by oxidation of active-site cysteines. J Bacteriol. Mar. 1999;181(5):1636-42.
Patnaik et al., Engineering of Escherichia coli central metabolism for aromatic metabolite production with near theoretical yield. Appl Environ Microbiol. Nov. 1994;60(11):3903-8.
Paul et al., Photophosphorylation in bacterial chromatophores entrapped in alginate gel: Improvement of the physical and biochemical properties of gel beads with barium as gel-inducing agent. Enzyme Microb Technol. 1980;2(4):281-87.
Peralta-Yahya et al., Microbial engineering for the production of advanced biofuels. Nature. Aug. 16, 2012;488(7411):320-8. doi: 10.1038/nature11478.
Pines et al., Expression and secretion of proteins in E. coli. Mol Biotechnol. Aug. 1999;12(1):25-34.
Pitera et al., Balancing a heterologous mevalonate pathway for improved isoprenoid production in Escherichia coli. Metab Eng. Mar. 2007;9(2):193-207. Epub Nov. 23, 2006.
Pravdic et al., Isoflurane protects cardiomyocytes and mitochondria by immediate and cytosol-independent action at reperfusion. Br J Pharmacol. May 2010;160(2):220-32. doi: 10.1111/j.1476-5381.2010.00698.x.
Qi et al., A one-step PCR-based method for rapid and efficient site-directed fragment deletion, insertion, and substitution mutagenesis. J Virolog Meth. Apr. 2008;149(1):85-90.
Ray et al., Mutational analysis of the catalytic and feedback sites of the tryptophan-sensitive 3-deoxy-D-arabino-heptulosonate-7-phosphate synthase of Escherichia coli. J Bacteriol. Dec. 1988;170(12):5500-6.
Reider et al., Total synthesis of thienamycin: a new approach from aspartic acid. Tetra Lett. 1982;23(22):2293-6.
Restiawaty et al., Feasibility of thermophilic adenosine triphosphate-regeneration system using Thermus thermophilus polyphosphate kinase. Process Biochemistry, Sep. 2011;46(9):1747-52.
Reyes et al., Genomic library screens for genes involved in n-butanol tolerance in Escherichia coli. PLoS One. Mar. 8, 2011;6(3):e17678.
Rodríguez et al., Identification of transcriptional activators for thienamycin and cephamycin C biosynthetic genes within the thienamycin gene cluster from Streptomyces cattleya. Mol Microbiol. Aug. 2008;69(3):633-45.
Rodríguez et al., Transcriptional organization of ThnI-regulated thienamycin biosynthetic genes in Streptomyces cattleya. J Antibiot (Tokyo). Mar. 2010;63(3):135-8. Epub Jan. 22, 2010.

(56) References Cited

OTHER PUBLICATIONS

Romanowski et al., Crystal structure of the *Escherichia coli* shikimate kinase I (AroK) that confers sensitivity to mecillinam. Proteins. Jun. 1, 2002;47(4):558-62.
Sagui et al., Enzymatic synthesis of ω-carboxy-β-hydroxy-(1)-α-amino acids. Tetrahedron. May 26, 2008;64(22):5079-84.
Salis et al., Automated design of synthetic ribosome binding sites to control protein expression. Nat Biotechnol. Oct. 2009;27(10):946-50. Epub Oct. 4, 2009. Supplemental material included.
Salzmann et al., A stereocontrolled synthesis of (+)-thienamycin. J Am Chem Soc. 1980;102(19);6161-3.
Salzmann et al., A stereocontrolled, enantiomerically specific total synthesis of thienamycin. Philos Trans R Soc Lond B Biol Sci. May 16, 1980;289(1036):191-5.
Sarath et al., Use of GFP as a reporter for the analysis of sequence-specific proteases. Curr Protoc Protein Sci. Feb. 2001;Chapter 21 Unit 9 Suppl. 26: 21.9.1-.10.
Sato et al., Poly[(R)-3-hydroxybutyrate] formation in *Escherichia coli* from glucose through an enoyl-CoA hydratase-mediated pathway. J Biosci Bioeng, Jan. 2007;103(1):38-44.
Sauer et al., The soluble and membrane-bound transhydrogenases UdhA and PntAB have divergent functions in NADPH metabolism of *Escherichia coli*. J Biol Chem. Feb. 20, 2004;279(8):6613-9. Epub Dec. 3, 2003.
Schierle et al., The DsbA signal sequence directs efficient, cotranslational export of passenger proteins to the *Escherichia coli* periplasm via the signal recognition particle pathway. J Bacteriol. Oct. 2003;185(19):5706-13.
Schlehuber et al., Prediction and identification of a permissive epitope insertion site in the vesicular stomatitis virus glycoprotein. J Virol. May 2004;78(10):5079-87.
Schnell, Protein targeting to the thylakoid membrane. Annu Rev Plant Physiol Plant Mol Biol. Jun. 1998;49:97-126.
Schultheisz et al., Pathway engineered enzymatic de novo purine nucleotide synthesis. ACS Chem Biol. Aug. 15, 2008;3(8):499-511. doi: 10.1021/cb800066p.
Scopes, Glycolysis in cell-free systems. New beer in an old bottle: Eduard Buchner and the growth of biochemical knowledge. Ed A. Cornish-Bowden. 1997;151-8.
Scopes, Studies with a reconstituted muscle glycolytic system. The anaerobic glycolytic response to simulated tetanic contraction. Biochem J. Jan. 1974;138(1):119-23.
Sheen, Metabolic repression of transcription in higher plants. Plant Cell. Oct. 1990;2(10):1027-38.
Shi et al., Molecular properties, functions, and potential applications of NAD kinases. Acta Biochim Biophys Sin (Shanghai). May 2009;41(5):352-61.
Shiba et al., Inorganic polyphosphate and polyphosphate kinase: their novel biological functions and applications. Biochemistry (Mosc). Mar. 2000;65(3):315-23.
Shine et al., Determinant of cistron specificity in bacterial ribosomes. Nature. Mar. 6, 1975;254(5495):34-8.
Simmons et al., Translational level is a critical factor for the secretion of heterologous proteins in *Escherichia coli*. Nat Biotechnol. May 1996;14(5):629-34.
Sleeman et al., Carboxymethylproline synthase (CarB), an unusual carbon-carbon bond-forming enzyme of the crotonase superfamily involved in carbapenem biosynthesis. J Biol Chem. Feb. 20, 2004;279(8):6730-6. Epub Nov. 18, 2003.
Soares et al., Periplasmic expression of human growth hormone via plasmid vectors containing the lambdaPL promoter: use of HPLC for product quantification. Protein Eng. Dec. 2003;16(12):1131-8.
Sorci et al., Nicotinamide mononucleotide synthetase is the key enzyme for an alternative route of NAD biosynthesis in Francisella tularensis.Proc Natl Acad Sci U S A. Mar. 3, 2009;106(9):30838. Epub Feb. 9, 2009. Supplemental material included.
Spickler et al., Action of RNase II and polynucleotide phosphorylase against RNAs containing stem-loops of defined structure. J Bacteriol. May 2000;182(9):2422-7.
Spirin, High-throughput cell-free systems for synthesis of functionally active proteins.Trends Biotechnol. Oct. 2004;22(10):538-45. With Supplementary data.
Srinivasan et al., The Enzymatic Synthesis of Shikimic Acid From D-Erythrose-4-Phosphate and Phosphoenolpyruvate1,2,3. J. Am. Chem. Soc. 1955;77(18):4943-4944.
Sroga et al., Periplasmic expression as a basis for whole cell kinetic screening of unnatural enzyme reactivities. Methods Enzymol. 2004;388:145-56.
Stadtman et al., Metal-catalyzed oxidation of proteins. Physiological consequences. J Biol Chem. Feb. 5, 1991;266(4):2005-8.
Stapon et al., Carbapenem biosynthesis: confirmation of stereochemical assignments and the role of CarC in the ring stereoinversion process from L-proline. J Am Chem Soc. Jul. 16, 2003;125(28):8486-93.
Stapon et al., Synthesis of (3S,5R)-carbapenam-3-carboxylic acid and its role in carbapenem biosynthesis and the stereoinversion problem. J Am Chem Soc. Dec. 24, 2003;125(51):15746-7.
Stazic et al., Antisense RNA protects mRNA from RNase E degradation by RNA-RNA duplex formation during phage infection. Nucleic Acids Res. Jun. 2011;39(11):4890-9. doi: 10.1093/nar/gkr037. Epub Feb. 15, 2011.
Stephanopoulos et al., Exploiting biological complexity for strain improvement through systems biology. Nat Biotechnol. Oct. 2004;22(10):1261-7.
Suzuki et al., Single protein production (SPP) system in *Escherichia coli*. Nat Protoc. 2007;2(7):1802-10.
Suzuki et al., Single protein production in living cells facilitated by an mRNA interferase. Mol Cell. Apr. 15, 2005;18(2):253-61.
Swartz et al., Advances in *Escherichia coli* production of therapeutic proteins. Curr Opin Biotechnol. Apr. 2001;12(2):195-201.
Swartz, Developing cell-free biology for industrial applications. J Ind Microbiol Biotechnol. Jul. 2006;33(7):476-85. Epub May 9, 2006. Review.
Swartz, Transforming biochemical engineering with cell-free biology. AIChE J. 2012;58(1):5-13.
Swartz, Universal cell-free protein synthesis. Nat Biotechnol. Aug. 2009;27(8):731-2. doi: 10.1038/nbt0809-731.
Sybesma et al., Increased production of folate by metabolic engineering of Lactococcus lactis. Appl Environ Microbiol. Jun. 2003;69(6):3069-76.
Thöny-Meyer et al., Translocation to the periplasm and signal sequence cleavage of preapocytochrome c depend on sec and lep, but not on the ccm gene products. Eur J Biochem. Jun. 15, 1997;246(3):794-9.
Tjalsma et al., Proteomics of protein secretion by Bacillus subtilis: separating the "secrets" of the secretome. Microbiol Mol Biol Rev. Jun. 2004;68(2):207-33.
Tracewell et al., Directed enzyme evolution: climbing fitness peaks one amino acid at a time. Curr Opin Chem Biol. Feb. 2009;13(1):3-9. Epub Feb. 25, 2009.
Tyo et al., Analysis of polyhydroxybutyrate flux limitations by systematic genetic and metabolic perturbations. Metab Eng. May 2010;12(3):187-95. Epub Oct. 30, 2009.
Van Bloois et al., Export of functional *Streptomyces coelicolor* alditol oxidase to the periplasm or cell surface of *Escherichia coli* and its application in whole-cell biocatalysis. Appl Microbiol Biotechnol. Jun. 2009;83(4):679-87. Epub Feb. 18, 2009.
Van Hees et al., Determination of low molecular weight organic acids in soil solution by HPLC. Talanta. Jan. 5, 1999;48(1):173-9.
Vander Heiden et al., Understanding the Warburg effect: the metabolic requirements of cell proliferation. Science. May 22, 2009;324(5930):1029-33. doi: 10.1126/science.1160809.
Voloshin et al., Efficient and scalable method for scaling up cell free protein synthesis in batch mode. Biotechnol Bioeng. Aug. 20, 2005;91(4):516-21.
Wahl et al., Molecular hybridization of immobilized nucleic acids: theoretical concepts and practical considerations. Methods Enzymol. 1987;152:399-407.
Wang et al., Programming cells by multiplex genome engineering and accelerated evolution. Nature. Aug. 13, 2009;460(7257):894-8. Epub Jul. 26, 2009.

(56) References Cited

OTHER PUBLICATIONS

Ward et al., Genomic insights into methanotrophy: the complete genome sequence of Methylococcus capsulatus (Bath). PLOS Biology. 2004;2(10):1616-28.
Weaver et al., Cloning of an aroF allele encoding a tyrosine-insensitive 3-deoxy-D-arabino-heptulosonate 7-phosphate synthase. J Bacteriol. Nov. 1990;172(11):6581-4.
Welch et al., Studies on cell-free metabolism: Ethanol production by a yeast glycolytic system reconstituted from purified enzymes. J Biotechnol. 1985;2:257-73.
Wiechert et al., A universal framework for 13C metabolic flux analysis. Metab Eng. Jul. 2001;3(3):265-83.
Wiechert, 13C metabolic flux analysis. Metab Eng. Jul. 2001;3(3):195-206.
Wilen et al., Tetrahedron report No. 38: Strategies in optical resolutions. Tetrahedron. 1977;33:2725-2736.
Williamson et al., Biosynthesis of the beta-lactam antibiotic, thienamycin, by *Streptomyces cattleya*. J Biol Chem. Apr. 25, 1985;260(8):4637-47.
Wilson et al., The shikimic acid pathway and polyketide biosynthesis. J Indust Microbiol Biotechnol. 1998;20:299-303.
Withers et al., Identification of isopentenol biosynthetic genes from Bacillus subtilis by a screening method based on isoprenoid precursor toxicity. Appl Environ Microbiol. Oct. 2007;73(19):6277-83. Epub Aug. 10, 2007.
Wong et al., Preparation of a mixture of nucleoside triphosphates from yeast RNA: use in enzymic synthesis requiring nucleoside triphosphate regeneration and conversion to nucleoside diphosphate sugars. J. Am. Chem. Soc. 1983;105(1):115-7.
Woodrow et al., A sequential expression system for high-throughput functional genomic analysis. Proteomics. Nov. 2007;7(21):3870-9.
Woodrow et al., Rapid expression of functional genomic libraries. J Proteome Res. Dec. 2006;5(12):3288-300.
Wuu et al., High yield cell-free production of integral membrane proteins without refolding or detergents. Biochim Biophys Acta. May 2008;1778(5):1237-50. doi: 10.1016/j.bbamem.2008.01.023. Epub Feb. 11, 2008.
Wylie et al., A single point mutation in ctp synthetase of chlamydia trachomatis confers resistance to cyclopentenyl cytosine. J Biol Chem. 1996;271:15393-400.
Yamaguchi et al., MqsR, a crucial regulator for quorum sensing and biofilm formation, is a GCU-specific mRNA interferase in *Escherichia coli*. J Biol Chem. Oct. 16, 2009;284(42):28746-53. Epub Aug. 18, 2009.
Yamaguchi et al., mRNA interferases, sequence-specific endoribonucleases from the toxin-antitoxin systems. Prog Mol Biol Transl Sci. 2009;85:467-500.
Yang et al., Export of methyl parathion hydrolase to the periplasm by the twin-arginine translocation pathway in *Escherichia coli*. J Agric Food Chem. Oct. 14, 2009;57(19):8901-5.
Yang et al., Rapid expression of vaccine proteins for B-cell lymphoma in a cell-free system. Biotechnol Bioeng. Mar. 5, 2005;89(5):503-11.
Ye et al., Synthetic metabolic engineering—a novel, simple technology for designing a chimeric metabolic pathway. Microb Cell Fact. Sep. 6, 2012;11:120. doi: 10.1186/1475-2859-11-120.
Yeo et al., Plasmodium falciparum CTP:phosphocholine cytidylyltransferase expressed in *Escherichia coli*: purification, characterization and lipid regulation. Biochem J. 1997;324:903-10.
Yu et al., Production of high-quality particulate methane monooxygenase in high yields from Methylococcus capsulatus (bath) with a hollow-fiber membrane bioreactor. J Bacteriol. Oct. 2003;185(20):5915-24.
Zago et al., Cloning and characterization of polyphosphate kinase and exopolyphosphatase genes from Pseudomonas aeruginosa 8830. Appl Environ Microbiol. May 1999;65(5):2065-71.
Zamboni et al., 13C-based metabolic flux analysis. Nat Protoc. 2009;4(6):878-92. Epub May 21, 2009.
Zawada et al., Effects of growth rate on cell extract performance in cell-free protein synthesis. Biotechnol Bioeng. Jul. 5, 2006;94(4):618-24.
Zawada et al., Maintaining rapid growth in moderate-density *Escherichia coli* fermentations. Biotechnol Bioeng. Feb. 20, 2005;89(4):407-15.
Zhang et al., Characterization of ChpBK, an mRNA interferase from *Escherichia coli*. J Biol Chem. Jul. 15, 2005;280(28):26080-8. Epub May 18, 2005.
Zhang et al., Characterization of YafO, an *Escherichia coli* toxin. J Biol Chem. Sep. 18, 2009;284(38):25522-31. Epub Jul. 17, 2009.
Zhang et al., Efficient regeneration of transgenic plants from rice protoplasts and correctly regulated expression of the foreign gene in the plants. Theor Appl Genet. 1988;76(6):835-40.
Zhang et al., Insights into the mRNA cleavage mechanism by MazF, an mRNA interferase. J Biol Chem. Feb. 4, 2005;280(5):3143-50. Epub Nov. 10, 2004.
Zhao et al., A novel high-throughput screening method for microbial transglutaminases with high specificity toward Gln141 of human growth hormone. J Biomol Screen. Feb. 2010;15(2):206-12. doi: 10.1177/1087057109356206. Epub Jan. 19, 2010.
Zhu et al., A high-energy-density sugar biobattery based on a synthetic enzymatic pathway. Nat Commun. 2014;5:3026. doi: 10.1038/ncomms4026.
International Preliminary Report on Patentability for PCT/US2016/024937, dated Oct. 12, 2017.
International Preliminary Report on Patentability for PCT/US2017/026285, dated Oct. 18, 2018.
Arnold et al., Proteolytic degradation of ribonuclease A in the pretransition region of thermally and urea-induced unfolding. Eur J Biochem. Jan. 2001;268(1):93-7.
Kuroda et al., Polyphosphate kinase as a nucleoside diphosphate kinase in *Escherichia coli* and Pseudomonas aeruginosa. Proc Natl Acad Sci U S A. Jan. 21, 1997;94(2):439-442.
Partial Supplementary European Search Report for EP 16774076.0, dated Jan. 21, 2019.
Extended European Search Report for EP 16774076.0, dated Apr. 24, 2019.
International Search Report and Written Opinion for PCT/US2018/055353, dated Jan. 7, 2019.
Atsumi et al., Acetolactate synthase from Bacillus subtilis serves as a 2-ketoisovalerate decarboxylase for isobutanol biosynthesis in *Escherichia coli*. Appl. Environ. Microbial. 2009;75:6306-11.
Bastian et al. Engineered ketol-acid reductoisomerase and alcohol dehydrogenase enable anaerobic 2-methylpropan-1-ol production at theoretical yield in *Escherichia coli*. Metab. Eng. 2011;13:345-52.
Dancz et al., Inducible control of virulence gene expression in Listeria monocytogenes: temporal requirement of listeriolysin O during intracellular infection. J Bacteriol. Nov. 2002;184(21):5935-45.
De La Plaza et al., Biochemical and molecular characterization of alpha-ketoisovalerate decarboxylase, an enzyme involved in the formation of aldehydes from amino acids by Lactococcus lactis. FEMS Microbial. Lett. 2004;238:367-374.
Hardy et al., Hepatitis C virus RNA synthesis in a cell-free system isolated from replicon-containing hepatoma cells. J Virol. Feb. 2003;77(3):2029-37.
Motomura et al., A new subfamily of polyphosphate kinase 2 (class III PPK2) catalyzes both nucleoside monophosphate phosphorylation and nucleoside diphosphate phosphorylation. Appl Environ Microbiol. Apr. 2014;80(8):2602-8. doi: 10.1128/AEM.03971-13. Epub Feb. 14, 2014.
Ninh et al., Development of a continuous bioconversion system using a thermophilic whole-cell biocatalyst. Appl Environ Microbiol. Mar. 2013;79(6):1996-2001. doi: 10.1128/AEM.03752-12. Epub Jan. 18, 2013.

\* cited by examiner

Us 10,954,541 B2

SEQUENCE LISTING

<160> NUMBER OF SEQ ID NOS: 28

<210> SEQ ID NO 1
<211> LENGTH: 813
<212> TYPE: PRT
<213> ORGANISM: Escherichia coli

<400> SEQUENCE: 1

Met Ser Gln Asp Pro Phe Gln Glu Arg Glu Ala Glu Lys Tyr Ala Asn
1               5                   10                  15

Pro Ile Pro Ser Arg Glu Phe Ile Leu Glu His Leu Thr Lys Arg Glu
            20                  25                  30

Lys Pro Ala Ser Arg Asp Glu Leu Ala Val Glu Leu His Ile Glu Gly
        35                  40                  45

Glu Glu Gln Leu Glu Gly Leu Arg Arg Arg Leu Arg Ala Met Glu Arg
    50                  55                  60

Asp Gly Gln Leu Val Phe Thr Arg Arg Gln Cys Tyr Ala Leu Pro Glu
65                  70                  75                  80

Arg Leu Asp Leu Val Lys Gly Thr Val Ile Gly His Arg Asp Gly Tyr
                85                  90                  95

Gly Phe Leu Arg Val Glu Gly Arg Lys Asp Asp Leu Tyr Leu Ser Ser
            100                 105                 110

Glu Gln Met Lys Thr Cys Ile His Gly Asp Gln Val Leu Ala Gln Pro
        115                 120                 125

Leu Gly Ala Asp Arg Lys Gly Arg Arg Glu Ala Arg Ile Val Arg Val
130                 135                 140

Leu Val Pro Lys Thr Ser Gln Ile Val Gly Arg Tyr Phe Thr Glu Ala
145                 150                 155                 160

Gly Val Gly Phe Val Val Pro Asp Asp Ser Arg Leu Ser Phe Asp Ile
                165                 170                 175

Leu Ile Pro Pro Asp Gln Ile Met Gly Ala Arg Met Gly Phe Val Val
                180                 185                 190

Val Val Glu Leu Thr Gln Arg Pro Thr Arg Arg Thr Lys Ala Val Gly
            195                 200                 205

Lys Ile Val Glu Val Leu Gly Asp Asn Met Gly Thr Gly Met Ala Val
210                 215                 220

Asp Ile Ala Leu Arg Thr His Glu Ile Pro Tyr Ile Trp Pro Gln Ala
225                 230                 235                 240

Val Glu Gln Gln Val Ala Gly Leu Lys Glu Val Pro Glu Glu Ala
                245                 250                 255

Lys Ala Gly Arg Val Asp Leu Arg Asp Leu Pro Leu Val Thr Ile Asp
                260                 265                 270

Gly Glu Asp Ala Arg Asp Phe Asp Asp Ala Val Tyr Cys Glu Lys Lys
            275                 280                 285

Arg Gly Gly Gly Trp Arg Leu Trp Val Ala Ile Ala Asp Val Ser Tyr
290                 295                 300

Tyr Val Arg Pro Ser Thr Pro Leu Asp Arg Glu Ala Arg Asn Arg Gly
305                 310                 315                 320

Thr Ser Val Tyr Phe Pro Ser Gln Val Ile Pro Met Leu Pro Glu Val
                325                 330                 335

Leu Ser Asn Gly Leu Cys Ser Leu Asn Pro Gln Val Asp Arg Leu Cys
                340                 345                 350

Met Val Cys Glu Met Thr Val Ser Ser Lys Gly Arg Leu Thr Gly Tyr
            355                 360                 365

Lys Phe Tyr Glu Ala Val Met Ser Ser His Ala Arg Leu Thr Tyr Thr
370                 375                 380

Lys Val Trp His Ile Leu Gln Gly Asp Gln Asp Leu Arg Glu Gln Tyr
385                 390                 395                 400

Ala Pro Leu Val Lys His Leu Glu Glu Leu His Asn Leu Tyr Lys Val
                405                 410                 415

Leu Asp Lys Ala Arg Glu Glu Arg Gly Gly Ile Ser Phe Glu Ser Glu
                420                 425                 430

Glu Ala Lys Phe Ile Phe Asn Ala Glu Arg Arg Ile Glu Arg Ile Glu
            435                 440                 445

Gln Thr Gln Arg Asn Asp Ala His Lys Leu Ile Glu Glu Cys Met Ile
450                 455                 460

Leu Ala Asn Ile Ser Ala Ala Arg Phe Val Glu Lys Ala Lys Glu Pro
465                 470                 475                 480

Ala Leu Phe Arg Ile His Asp Lys Pro Ser Thr Glu Ala Ile Thr Ser
                485                 490                 495

Phe Arg Ser Val Leu Ala Glu Leu Gly Leu Glu Leu Pro Gly Gly Asn
                500                 505                 510

Lys Pro Glu Pro Arg Asp Tyr Ala Glu Leu Leu Glu Ser Val Ala Asp
            515                 520                 525

Arg Pro Asp Ala Glu Met Leu Gln Thr Met Leu Leu Arg Ser Met Lys
530                 535                 540

```
Gln Ala Ile Tyr Asp Pro Glu Asn Arg Gly His Phe Gly Leu Ala Leu
545                 550                 555                 560
Gln Ser Tyr Ala His Phe Thr Ser Pro Ile Arg Arg Tyr Pro Asp Leu
                565                 570                 575
Thr Leu His Arg Ala Ile Lys Tyr Leu Leu Ala Lys Glu Gln Gly His
            580                 585                 590
Gln Gly Asn Thr Thr Glu Thr Gly Gly Tyr His Tyr Ser Met Glu Glu
        595                 600                 605
Met Leu Gln Leu Gly Gln His Cys Ser Met Ala Glu Arg Arg Ala Asp
610                 615                 620
Glu Ala Thr Arg Asp Val Ala Asp Trp Leu Lys Cys Asp Phe Met Leu
625                 630                 635                 640
Asp Gln Val Gly Asn Val Phe Lys Gly Val Ile Ser Ser Val Thr Gly
                645                 650                 655
Phe Gly Phe Phe Val Arg Leu Asp Asp Leu Phe Ile Asp Gly Leu Val
            660                 665                 670
His Val Ser Ser Leu Asp Asn Asp Tyr Tyr Arg Phe Asp Gln Val Gly
        675                 680                 685
Gln Arg Leu Met Gly Glu Ser Ser Gly Gln Thr Tyr Arg Leu Gly Asp
    690                 695                 700
Arg Val Glu Val Arg Val Glu Ala Val Asn Met Asp Glu Arg Lys Ile
705                 710                 715                 720
Asp Phe Ser Leu Ile Ser Ser Glu Arg Ala Pro Arg Asn Val Gly Lys
                725                 730                 735
Thr Ala Arg Glu Lys Ala Lys Lys Gly Asp Ala Gly Lys Lys Gly Gly
            740                 745                 750
Lys Arg Arg Gln Val Gly Lys Val Asn Phe Glu Pro Asp Ser Ala
    755                 760                 765
Phe Arg Gly Glu Lys Lys Thr Lys Pro Lys Ala Ala Lys Lys Asp Ala
770                 775                 780
Arg Lys Ala Lys Lys Pro Ser Ala Lys Thr Gln Lys Ile Ala Ala Ala
785                 790                 795                 800
Thr Lys Ala Lys Arg Ala Ala Lys Lys Lys Val Ala Glu
            805                 810

<210> SEQ ID NO 2
<211> LENGTH: 732
<212> TYPE: PRT
<213> ORGANISM: Thermosynechococcus elongatus

<400> SEQUENCE: 2

Met Pro Ser Ala Lys Ser Pro Arg Arg Lys Ala Pro Glu Pro Ile Asp
1               5                   10                  15
Leu Asp Asn Pro Gln Tyr Tyr Phe Asn Arg Ser Leu Ser Trp Leu Glu
                20                  25                  30
Phe Asn Lys Arg Val Leu His Glu Ala Tyr Asp Pro Arg Thr Pro Leu
            35                  40                  45
Leu Glu Arg Leu Lys Phe Met Ala Ile Phe Ser Ser Asn Leu Asp Glu
        50                  55                  60
Phe Phe Met Val Arg Val Ala Gly Leu Lys Gln Gln Val Glu Ser Gly
65                  70                  75                  80
Ile Leu Gln Val Gly Ala Asp Gly Met Pro Pro Ala Glu Gln Leu Gln
                85                  90                  95
Ala Val Arg Gln Tyr Leu Leu Pro Ile Val Thr Glu Gln His Arg Tyr
            100                 105                 110
```

```
Phe Asp Gln Glu Leu Arg Ala Leu Leu Ala Lys Ser Ile Phe Leu
            115                 120                 125

Thr Arg Phe Asn Glu Leu Thr Pro Glu Gln Gln Ala Tyr Leu Asn Asp
130                 135                 140

Tyr Phe Gln Ala Gln Val Phe Pro Val Leu Thr Pro Leu Ala Val Asp
145                 150                 155                 160

Pro Ala His Pro Phe Pro Tyr Ile Ser Ser Leu Ser Leu Asn Leu Ala
                165                 170                 175

Val Leu Ile Arg Asp Pro Glu Ser Gly Gln Glu Arg Leu Ala Arg Val
            180                 185                 190

Lys Val Pro Asn Gln Phe Pro Arg Phe Val Ala Leu Pro Gln His Leu
            195                 200                 205

His Ser Pro Gln Gly Val His Trp Leu Gly Val Pro Leu Glu Glu Ile
210                 215                 220

Ile Ala His Asn Leu Ser Ala Leu Phe Pro Gly Met Glu Ile Glu Ala
225                 230                 235                 240

Tyr Phe Ala Phe Arg Ile Thr Arg Ser Ala Asp Leu Glu Leu Glu Thr
                245                 250                 255

Asp Lys Ala Asp Asp Leu Leu Ile Ala Ile Glu Gln Glu Ile Arg Lys
            260                 265                 270

Arg Arg Phe Gly Ser Val Val Arg Leu Glu Val Gln Arg Gly Ile Pro
            275                 280                 285

Pro Leu Leu Arg Gln Thr Leu Met Glu Glu Met Asp Leu Glu Glu Ile
            290                 295                 300

Asp Val Tyr Glu Leu Glu Gly Leu Leu Cys Leu Asn Asp Leu Phe Ala
305                 310                 315                 320

Phe Met Gly Leu Pro Leu Pro Gln Phe Lys Asp Pro Glu Trp Gln Pro
                325                 330                 335

Gln Val Pro Pro Ser Phe Gln Arg Val Glu Glu Arg Glu Ser Met Phe
            340                 345                 350

Asp Thr Ser Ser Glu Ile Thr Thr Leu Gly Thr Asp Tyr Trp Glu Ala
            355                 360                 365

Val Ala Asn Glu Leu Phe Ser Leu Ile Arg Glu Gly Asp Ile Ile Val
            370                 375                 380

His His Pro Tyr His Ser Phe Ala Ala Thr Val Gln Arg Phe Ile Thr
385                 390                 395                 400

Leu Ala Ala His Asp Pro Gln Val Leu Ala Ile Lys Ile Thr Leu Tyr
                405                 410                 415

Arg Thr Ser Gly Asp Ser Pro Ile Val Ser Ala Leu Ile Lys Ala Ala
            420                 425                 430

Glu Asn Gly Lys Gln Val Ala Val Leu Val Glu Leu Lys Ala Arg Phe
            435                 440                 445

Asp Glu Glu Asn Asn Ile Leu Trp Ala Arg Lys Leu Glu Lys Val Gly
450                 455                 460

Val His Val Val Tyr Gly Val Pro Gly Leu Lys Thr His Thr Lys Thr
465                 470                 475                 480

Val Leu Val Val Arg Gln Glu Ala Gly Gln Ile Arg Arg Tyr Val His
                485                 490                 495

Ile Gly Thr Gly Asn Tyr Asn Pro Lys Thr Ala Ser Leu Tyr Glu Asp
            500                 505                 510

Leu Gly Leu Phe Ser Cys Arg Glu Glu Leu Gly Ala Asp Leu Ser Glu
            515                 520                 525
```

-continued

```
Leu Phe Asn Val Leu Thr Gly Tyr Ala Arg Gln Arg Asp Tyr Arg Lys
530                 535                 540

Leu Leu Val Ala Pro Val Thr Met Arg Asp Arg Thr Leu Gln Leu Ile
545                 550                 555                 560

Tyr Arg Glu Ile Glu His Ala Arg Asn Gly Gln Pro Ala Arg Ile Ile
                565                 570                 575

Ala Lys Met Asn Ala Ile Thr Asp Thr Gln Val Ile Arg Ala Leu Tyr
            580                 585                 590

Glu Ala Ser Gln Ala Gly Val Asp Ile Asp Leu Ile Ile Arg Gly Met
        595                 600                 605

Cys Cys Leu Arg Pro Gly Val Pro Gly Val Ser Asp Arg Ile Arg Val
610                 615                 620

Ile Ser Ile Ile Gly Arg Phe Leu Glu His Ser Arg Ile Phe Tyr Phe
625                 630                 635                 640

Gly Asn Asn Gly Asp Pro Glu Tyr Tyr Ile Gly Ser Ala Asp Trp Arg
                645                 650                 655

Ser Arg Asn Leu Asp Arg Arg Val Glu Ala Ile Thr Pro Ile Glu Asp
            660                 665                 670

Pro Ala Ile Gln Leu Glu Leu Lys Glu Arg Leu Glu Ile Met Leu Ala
        675                 680                 685

Asp Asn Arg Gln Ala Trp Glu Leu Gln Pro Asp Gly Thr Tyr Arg Gln
690                 695                 700

Arg Gln Pro Ala Pro Gly Glu Ala Glu Arg Gly Thr His Ser Val Leu
705                 710                 715                 720

Met Ala Arg Thr Leu Lys Asp Val Gln Gly Ser His
                725                 730

<210> SEQ ID NO 3
<211> LENGTH: 225
<212> TYPE: PRT
<213> ORGANISM: Pyrococcus furiosus

<400> SEQUENCE: 3

Met Arg Ile Val Phe Asp Ile Gly Gly Ser Val Leu Val Pro Glu Asn
1               5                   10                  15

Pro Asp Ile Asp Phe Ile Lys Glu Ile Ala Tyr Gln Leu Thr Lys Val
                20                  25                  30

Ser Glu Asp His Glu Val Ala Val Val Gly Gly Gly Lys Leu Ala
            35                  40                  45

Arg Lys Tyr Ile Glu Val Ala Glu Lys Phe Asn Ser Ser Glu Thr Phe
50                  55                  60

Lys Asp Phe Ile Gly Ile Gln Ile Thr Arg Ala Asn Ala Met Leu Leu
65                  70                  75                  80

Ile Ala Ala Leu Arg Glu Lys Ala Tyr Pro Val Val Glu Asp Phe
                85                  90                  95

Trp Glu Ala Trp Lys Ala Val Gln Leu Lys Lys Ile Pro Val Met Gly
                100                 105                 110

Gly Thr His Pro Gly His Thr Thr Asp Ala Val Ala Ala Leu Leu Ala
            115                 120                 125

Glu Phe Leu Lys Ala Asp Leu Leu Val Val Ile Thr Asn Val Asp Gly
        130                 135                 140

Val Tyr Thr Ala Asp Pro Lys Lys Asp Pro Thr Ala Lys Lys Ile Lys
145                 150                 155                 160

Lys Met Lys Pro Glu Glu Leu Leu Glu Ile Val Gly Lys Gly Ile Glu
                165                 170                 175
```

Lys Ala Gly Ser Ser Val Ile Asp Pro Leu Ala Ala Lys Ile Ile
            180                 185                 190

Ala Arg Ser Gly Ile Lys Thr Ile Val Ile Gly Lys Glu Asp Ala Lys
            195                 200                 205

Asp Leu Phe Arg Val Ile Lys Gly Asp His Asn Gly Thr Thr Ile Glu
            210                 215                 220

Pro
225

<210> SEQ ID NO 4
<211> LENGTH: 208
<212> TYPE: PRT
<213> ORGANISM: Thermus thermophilus

<400> SEQUENCE: 4

Met Arg Gly Ile Val Thr Ile Asp Gly Pro Ser Ala Ser Gly Lys Ser
1               5                   10                  15

Ser Val Ala Arg Arg Val Ala Ala Leu Gly Val Pro Tyr Leu Ser
            20                  25                  30

Ser Gly Leu Leu Tyr Arg Ala Ala Ala Phe Leu Ala Leu Arg Ala Gly
            35                  40                  45

Val Asp Pro Gly Asp Glu Glu Gly Leu Leu Ala Leu Leu Glu Gly Leu
        50                  55                  60

Gly Val Arg Leu Leu Ala Gln Ala Glu Gly Asn Arg Val Leu Ala Asp
65                  70                  75                  80

Gly Glu Asp Leu Thr Ser Phe Leu His Thr Pro Glu Val Asp Arg Val
            85                  90                  95

Val Ser Ala Val Ala Arg Leu Pro Gly Val Arg Ala Trp Val Asn Arg
            100                 105                 110

Arg Leu Lys Glu Val Pro Pro Phe Val Ala Glu Gly Arg Asp Met
            115                 120                 125

Gly Thr Ala Val Phe Pro Glu Ala Ala His Lys Phe Tyr Leu Thr Ala
        130                 135                 140

Ser Pro Glu Val Arg Ala Trp Arg Arg Ala Arg Glu Arg Pro Gln Ala
145                 150                 155                 160

Tyr Glu Glu Val Leu Arg Asp Leu Leu Arg Arg Asp Glu Arg Asp Lys
            165                 170                 175

Ala Gln Ser Ala Pro Ala Pro Asp Ala Leu Val Leu Asp Thr Gly Gly
            180                 185                 190

Met Thr Leu Asp Glu Val Val Ala Trp Val Leu Ala His Ile Arg Arg
        195                 200                 205

<210> SEQ ID NO 5
<211> LENGTH: 207
<212> TYPE: PRT
<213> ORGANISM: Thermatoga maritima

<400> SEQUENCE: 5

Met Lys Gly Gln Leu Phe Val Ile Cys Gly Pro Ser Gly Ala Gly Lys
1               5                   10                  15

Thr Ser Ile Ile Lys Glu Val Leu Lys Arg Leu Asp Asn Val Val Phe
            20                  25                  30

Ser Val Ser Cys Thr Thr Arg Pro Lys Arg Pro His Glu Glu Asp Gly
            35                  40                  45

Lys Asp Tyr Phe Phe Ile Thr Glu Glu Glu Phe Leu Arg Val Glu
        50                  55                  60

```
Arg Gly Glu Phe Leu Glu Trp Ala Arg Val His Gly His Leu Tyr Gly
 65                  70                  75                  80

Thr Leu Arg Ser Phe Val Glu Ser His Ile Asn Glu Gly Lys Asp Val
                 85                  90                  95

Val Leu Asp Ile Asp Val Gln Gly Ala Leu Ser Val Lys Lys Lys Tyr
            100                 105                 110

Ser Asn Thr Val Phe Ile Tyr Val Ala Pro Pro Ser Tyr Ala Asp Leu
            115                 120                 125

Arg Glu Arg Ile Leu Lys Arg Gly Thr Glu Lys Glu Ala Asp Val Leu
130                 135                 140

Val Arg Leu Glu Asn Ala Lys Trp Glu Leu Met Phe Met Asp Glu Phe
145                 150                 155                 160

Asp Tyr Ile Val Val Asn Glu Asn Leu Glu Asp Ala Val Glu Met Val
                165                 170                 175

Val Ser Ile Val Arg Ser Glu Arg Ala Lys Val Thr Arg Asn Gln Asp
            180                 185                 190

Lys Ile Glu Arg Phe Lys Met Glu Val Lys Gly Trp Lys Lys Leu
            195                 200                 205

<210> SEQ ID NO 6
<211> LENGTH: 186
<212> TYPE: PRT
<213> ORGANISM: Thermus thermophilus

<400> SEQUENCE: 6

Met Asp Val Gly Gln Ala Val Ile Phe Leu Gly Pro Pro Gly Ala Gly
  1               5                  10                  15

Lys Gly Thr Gln Ala Ser Arg Leu Ala Gln Glu Leu Gly Phe Lys Lys
                 20                  25                  30

Leu Ser Thr Gly Asp Ile Leu Arg Asp His Val Ala Arg Gly Thr Pro
             35                  40                  45

Leu Gly Glu Arg Val Arg Pro Ile Met Glu Arg Gly Asp Leu Val Pro
 50                  55                  60

Asp Asp Leu Ile Leu Glu Leu Ile Arg Glu Glu Leu Ala Glu Arg Val
 65                  70                  75                  80

Ile Phe Asp Gly Phe Pro Arg Thr Leu Ala Gln Ala Glu Ala Leu Asp
                 85                  90                  95

Arg Leu Leu Ser Glu Thr Gly Thr Arg Leu Leu Gly Val Val Leu Val
            100                 105                 110

Glu Val Pro Glu Glu Glu Leu Val Arg Arg Ile Leu Arg Arg Ala Glu
            115                 120                 125

Leu Glu Gly Arg Ser Asp Asp Asn Glu Glu Thr Val Arg Arg Arg Leu
130                 135                 140

Glu Val Tyr Arg Glu Lys Thr Glu Pro Leu Val Gly Tyr Tyr Glu Ala
145                 150                 155                 160

Arg Gly Val Leu Lys Arg Val Asp Gly Leu Gly Thr Pro Asp Glu Val
                165                 170                 175

Tyr Ala Arg Ile Arg Ala Ala Leu Gly Ile
            180                 185

<210> SEQ ID NO 7
<211> LENGTH: 142
<212> TYPE: PRT
<213> ORGANISM: Aquifex aeolicus

<400> SEQUENCE: 7
```

```
Met Ala Val Glu Arg Thr Leu Ile Ile Val Lys Pro Asp Ala Met Glu
1               5                   10                  15

Lys Gly Ala Leu Gly Lys Ile Leu Asp Arg Phe Ile Gln Glu Gly Phe
            20                  25                  30

Gln Ile Lys Ala Leu Lys Met Phe Arg Phe Thr Pro Glu Lys Ala Gly
        35                  40                  45

Glu Phe Tyr Tyr Val His Arg Glu Arg Pro Phe Phe Gln Glu Leu Val
50                  55                  60

Glu Phe Met Ser Ser Gly Pro Val Val Ala Val Leu Glu Gly Glu
65                  70                  75                  80

Asp Ala Ile Lys Arg Val Arg Glu Ile Ile Gly Pro Thr Asp Ser Glu
                85                  90                  95

Glu Ala Arg Lys Val Ala Pro Asn Ser Ile Arg Ala Gln Phe Gly Thr
            100                 105                 110

Asp Lys Gly Lys Asn Ala Ile His Ala Ser Asp Ser Pro Glu Ser Ala
        115                 120                 125

Gln Tyr Glu Ile Cys Phe Ile Phe Ser Gly Leu Glu Ile Val
130                 135                 140
```

<210> SEQ ID NO 8
<211> LENGTH: 280
<212> TYPE: PRT
<213> ORGANISM: Meiothermus ruber

<400> SEQUENCE: 8

```
Met Gly Phe Cys Ser Ile Glu Phe Leu Met Gly Ala Gln Met Lys Lys
1               5                   10                  15

Tyr Arg Val Gln Pro Asp Gly Arg Phe Glu Leu Lys Arg Phe Asp Pro
            20                  25                  30

Asp Asp Thr Ser Ala Phe Glu Gly Gly Lys Gln Ala Ala Leu Glu Ala
        35                  40                  45

Leu Ala Val Leu Asn Arg Arg Leu Glu Lys Leu Gln Glu Leu Leu Tyr
50                  55                  60

Ala Glu Gly Gln His Lys Val Leu Val Val Leu Gln Ala Met Asp Ala
65                  70                  75                  80

Gly Gly Lys Asp Gly Thr Ile Arg Val Phe Asp Gly Val Asn Pro
                85                  90                  95

Ser Gly Val Arg Val Ala Ser Phe Gly Val Pro Thr Glu Gln Glu Leu
            100                 105                 110

Ala Arg Asp Tyr Leu Trp Arg Val His Gln Gln Val Pro Arg Lys Gly
        115                 120                 125

Glu Leu Val Ile Phe Asn Arg Ser His Tyr Glu Asp Val Leu Val Val
130                 135                 140

Arg Val Lys Asn Leu Val Pro Gln Gln Val Trp Gln Lys Arg Tyr Arg
145                 150                 155                 160

His Ile Arg Glu Phe Glu Arg Met Leu Ala Asp Glu Gly Thr Thr Ile
                165                 170                 175

Leu Lys Phe Phe Leu His Ile Ser Lys Asp Glu Gln Arg Gln Arg Leu
            180                 185                 190

Gln Glu Arg Leu Asp Asn Pro Glu Lys Arg Trp Lys Phe Arg Met Gly
        195                 200                 205

Asp Leu Glu Asp Arg Arg Leu Trp Asp Arg Tyr Gln Glu Ala Tyr Glu
210                 215                 220

Ala Ala Ile Arg Glu Thr Ser Thr Glu Tyr Ala Pro Trp Tyr Val Ile
```

```
                    225                 230                 235                 240

Pro Ala Asn Lys Asn Trp Tyr Arg Asn Trp Leu Val Ser His Ile Leu
                        245                 250                 255

Val Glu Thr Leu Glu Gly Leu Ala Met Gln Tyr Pro Gln Pro Glu Thr
                        260                 265                 270

Ala Ser Glu Lys Ile Val Ile Glu
                        275                 280

<210> SEQ ID NO 9
<211> LENGTH: 268
<212> TYPE: PRT
<213> ORGANISM: Meiothermus silvanus

<400> SEQUENCE: 9

Met Ala Lys Thr Ile Gly Ala Thr Leu Asn Leu Gln Asp Ile Asp Pro
        1               5                   10                  15

Arg Ser Thr Pro Gly Phe Asn Gly Asp Lys Glu Lys Ala Leu Ala Leu
                        20                  25                  30

Leu Glu Lys Leu Thr Ala Arg Leu Asp Glu Leu Gln Glu Gln Leu Tyr
                        35                  40                  45

Ala Glu His Gln His Arg Val Leu Val Ile Leu Gln Gly Met Asp Thr
                        50                  55                  60

Ser Gly Lys Asp Gly Thr Ile Arg His Val Phe Lys Asn Val Asp Pro
        65                  70                  75                  80

Leu Gly Val Arg Val Val Ala Phe Lys Ala Pro Thr Pro Glu Leu
                        85                  90                  95

Glu Arg Asp Tyr Leu Trp Arg Val His Gln His Val Pro Ala Asn Gly
                        100                 105                 110

Glu Leu Val Ile Phe Asn Arg Ser His Tyr Glu Asp Val Leu Val Ala
                        115                 120                 125

Arg Val His Asn Leu Val Pro Pro Ala Ile Trp Ser Arg Arg Tyr Asp
                        130                 135                 140

His Ile Asn Ala Phe Glu Lys Met Leu Val Asp Glu Gly Thr Thr Val
        145                 150                 155                 160

Leu Lys Phe Phe Leu His Ile Ser Lys Glu Gln Lys Lys Arg Leu
                        165                 170                 175

Leu Glu Arg Leu Val Glu Ala Asp Lys His Trp Lys Phe Asp Pro Gln
                        180                 185                 190

Asp Leu Val Glu Arg Gly Tyr Trp Glu Asp Tyr Met Glu Ala Tyr Gln
                        195                 200                 205

Asp Val Leu Asp Lys Thr His Thr Gln Tyr Ala Pro Trp His Val Ile
                        210                 215                 220

Pro Ala Asp Arg Lys Trp Tyr Arg Asn Leu Gln Val Ser Arg Leu Leu
        225                 230                 235                 240

Val Glu Ala Leu Glu Gly Leu Arg Met Lys Tyr Pro Arg Pro Lys Leu
                        245                 250                 255

Asn Ile Pro Arg Leu Lys Ser Glu Leu Glu Lys Met
                        260                 265

<210> SEQ ID NO 10
<211> LENGTH: 266
<212> TYPE: PRT
<213> ORGANISM: Deinococcus geothermalis

<400> SEQUENCE: 10

Met Gln Leu Asp Arg Tyr Arg Val Pro Pro Gly Gln Arg Val Arg Leu
```

```
1               5                   10                  15
Ser Asn Trp Pro Thr Asp Asp Gly Gly Leu Ser Lys Ala Glu Gly
            20                  25                  30

Glu Ala Leu Leu Pro Asp Leu Gln Gln Arg Leu Ala Asn Leu Gln Glu
            35                  40                  45

Arg Leu Tyr Ala Glu Ser Gln Gln Ala Leu Leu Ile Val Leu Gln Ala
        50                  55                  60

Arg Asp Ala Gly Gly Lys Asp Gly Thr Val Lys His Val Ile Gly Ala
65                  70                  75                  80

Phe Asn Pro Ser Gly Val Gln Val Ser Asn Phe Lys Val Pro Thr Glu
                85                  90                  95

Glu Glu Arg Ala His Asp Phe Leu Trp Arg Ile His Arg Gln Thr Pro
            100                 105                 110

Arg Leu Gly Met Ile Gly Val Phe Asn Arg Ser Gln Tyr Glu Asp Val
            115                 120                 125

Leu Val Thr Arg Val His His Leu Ile Asp Asp Gln Thr Ala Gln Arg
        130                 135                 140

Arg Leu Lys His Ile Cys Ala Phe Glu Ser Leu Leu Thr Asp Ser Gly
145                 150                 155                 160

Thr Arg Ile Val Lys Phe Tyr Leu His Ile Ser Pro Glu Glu Gln Lys
                165                 170                 175

Lys Arg Leu Glu Ala Arg Leu Ala Asp Pro Ser Lys His Trp Lys Phe
            180                 185                 190

Asn Pro Gly Asp Leu Gln Glu Arg Ala His Trp Asp Ala Tyr Thr Ala
            195                 200                 205

Val Tyr Glu Asp Val Leu Thr Thr Ser Thr Pro Ala Ala Pro Trp Tyr
        210                 215                 220

Val Val Pro Ala Asp Arg Lys Trp Phe Arg Asn Leu Leu Val Ser Gln
225                 230                 235                 240

Ile Leu Val Gln Thr Leu Glu Glu Met Asn Pro Gln Phe Pro Ala Pro
                245                 250                 255

Ala Phe Asn Ala Ala Asp Leu Arg Ile Val
            260                 265

<210> SEQ ID NO 11
<211> LENGTH: 300
<212> TYPE: PRT
<213> ORGANISM: Thermosynechococcus elongatus

<400> SEQUENCE: 11

Met Ile Pro Gln Asp Phe Leu Asp Glu Ile Asn Pro Asp Arg Tyr Ile
1               5                   10                  15

Val Pro Ala Gly Gly Asn Phe His Trp Lys Asp Tyr Asp Pro Gly Asp
            20                  25                  30

Thr Ala Gly Leu Lys Ser Lys Val Glu Ala Gln Glu Leu Leu Ala Ala
            35                  40                  45

Gly Ile Lys Lys Leu Ala Ala Tyr Gln Asp Val Leu Tyr Ala Gln Asn
        50                  55                  60

Ile Tyr Gly Leu Leu Ile Ile Phe Gln Ala Met Asp Ala Ala Gly Lys
65                  70                  75                  80

Asp Ser Thr Ile Lys His Val Met Ser Gly Leu Asn Pro Gln Ala Cys
                85                  90                  95

Arg Val Tyr Ser Phe Lys Ala Pro Ser Ala Glu Glu Leu Asp His Asp
            100                 105                 110
```

```
Phe Leu Trp Arg Ala Asn Arg Ala Leu Pro Glu Arg Gly Cys Ile Gly
            115                 120                 125

Ile Phe Asn Arg Ser Tyr Tyr Glu Glu Val Leu Val Val Arg Val His
        130                 135                 140

Pro Asp Leu Leu Asn Arg Gln Gln Leu Pro Pro Glu Thr Lys Thr Lys
145                 150                 155                 160

His Ile Trp Lys Glu Arg Phe Glu Asp Ile Asn His Tyr Glu Arg Tyr
                165                 170                 175

Leu Thr Arg Asn Gly Ile Leu Ile Leu Lys Phe Phe Leu His Ile Ser
            180                 185                 190

Lys Ala Glu Gln Lys Lys Arg Phe Leu Glu Arg Ile Ser Arg Pro Glu
        195                 200                 205

Lys Asn Trp Lys Phe Ser Ile Glu Asp Val Arg Asp Arg Ala His Trp
210                 215                 220

Asp Asp Tyr Gln Gln Ala Tyr Ala Asp Val Phe Arg His Thr Ser Thr
225                 230                 235                 240

Lys Trp Ala Pro Trp His Ile Ile Pro Ala Asn His Lys Trp Phe Ala
                245                 250                 255

Arg Leu Met Val Ala His Phe Ile Tyr Gln Lys Leu Ala Ser Leu Asn
            260                 265                 270

Leu His Tyr Pro Met Leu Ser Glu Ala His Arg Glu Gln Leu Leu Glu
        275                 280                 285

Ala Lys Ala Leu Leu Glu Asn Glu Pro Asp Glu Asp
290                 295                 300

<210> SEQ ID NO 12
<211> LENGTH: 281
<212> TYPE: PRT
<213> ORGANISM: Anaerolinea thermophila

<400> SEQUENCE: 12

Met Gly Glu Ala Met Glu Arg Tyr Phe Ile Lys Pro Gly Glu Lys Val
1               5                   10                  15

Arg Leu Lys Asp Trp Ser Pro Asp Pro Lys Asp Phe Glu Gly Asp
            20                  25                  30

Lys Glu Ser Thr Arg Ala Ala Val Ala Glu Leu Asn Arg Lys Leu Glu
        35                  40                  45

Val Leu Gln Glu Arg Leu Tyr Ala Glu Arg Lys His Lys Val Leu Val
    50                  55                  60

Ile Leu Gln Gly Met Asp Thr Ser Gly Lys Asp Gly Val Ile Arg Ser
65                  70                  75                  80

Val Phe Glu Gly Val Asn Pro Gln Gly Val Lys Val Ala Asn Phe Lys
                85                  90                  95

Val Pro Thr Gln Glu Glu Leu Asp His Asp Tyr Leu Trp Arg Val His
            100                 105                 110

Lys Val Val Pro Gly Lys Gly Glu Ile Val Ile Phe Asn Arg Ser His
        115                 120                 125

Tyr Glu Asp Val Leu Val Val Arg Val His Asn Leu Val Pro Pro Glu
    130                 135                 140

Val Trp Lys Lys Arg Tyr Glu Gln Ile Asn Gln Phe Glu Arg Leu Leu
145                 150                 155                 160

His Glu Thr Gly Thr Thr Ile Leu Lys Phe Phe Leu Phe Ile Ser Arg
                165                 170                 175

Glu Glu Gln Lys Gln Arg Leu Leu Glu Arg Leu Ala Asp Pro Ala Lys
            180                 185                 190
```

```
His Trp Lys Phe Asn Pro Gly Asp Leu Lys Glu Arg Ala Leu Trp Glu
            195                 200                 205

Glu Tyr Glu Lys Ala Tyr Glu Asp Val Leu Ser Arg Thr Ser Thr Glu
            210                 215                 220

Tyr Ala Pro Trp Ile Leu Val Pro Ala Asp Lys Lys Trp Tyr Arg Asp
225                 230                 235                 240

Trp Val Ile Ser Arg Val Leu Val Glu Thr Leu Glu Gly Leu Glu Ile
            245                 250                 255

Gln Leu Pro Pro Leu Ala Asp Ala Glu Thr Tyr Arg Arg Gln Leu
            260                 265                 270

Leu Glu Glu Asp Ala Pro Glu Ser Arg
            275                 280

<210> SEQ ID NO 13
<211> LENGTH: 270
<212> TYPE: PRT
<213> ORGANISM: Caldilinea aerophila

<400> SEQUENCE: 13

Met Asp Val Asp Arg Tyr Arg Val Pro Pro Gly Ser Thr Ile His Leu
1               5                   10                  15

Ser Gln Trp Pro Pro Asp Asp Arg Ser Leu Tyr Glu Gly Asp Lys Lys
            20                  25                  30

Gln Gly Lys Gln Asp Leu Ser Ala Leu Asn Arg Arg Leu Glu Thr Leu
        35                  40                  45

Gln Glu Leu Leu Tyr Ala Glu Gly Lys His Lys Val Leu Ile Ile Leu
50                  55                  60

Gln Gly Met Asp Thr Ser Gly Lys Asp Gly Val Ile Arg His Val Phe
65                  70                  75                  80

Asn Gly Val Asn Pro Gln Gly Val Lys Val Ala Ser Phe Lys Val Pro
            85                  90                  95

Thr Ala Val Glu Leu Ala His Asp Phe Leu Trp Arg Ile His Arg Gln
            100                 105                 110

Thr Pro Gly Ser Gly Glu Ile Val Ile Phe Asn Arg Ser His Tyr Glu
            115                 120                 125

Asp Val Leu Val Val Arg Val His Gly Leu Val Pro Pro Glu Val Trp
            130                 135                 140

Ala Arg Arg Tyr Glu His Ile Asn Ala Phe Glu Lys Leu Leu Val Asp
145                 150                 155                 160

Glu Gly Thr Thr Ile Leu Lys Phe Phe Leu His Ile Ser Lys Glu Glu
            165                 170                 175

Gln Arg Gln Arg Leu Leu Glu Arg Leu Glu Met Pro Glu Lys Arg Trp
            180                 185                 190

Lys Phe Ser Val Gly Asp Leu Ala Glu Arg Lys Arg Trp Asp Glu Tyr
            195                 200                 205

Met Ala Ala Tyr Glu Ala Val Leu Ser Lys Thr Ser Thr Glu Tyr Ala
            210                 215                 220

Pro Trp Tyr Ile Val Pro Ser Asp Arg Lys Trp Tyr Arg Asn Leu Val
225                 230                 235                 240

Ile Ser His Val Ile Ile Asn Ala Leu Glu Gly Leu Asn Met Arg Tyr
            245                 250                 255

Pro Gln Pro Glu Asp Ile Ala Phe Asp Thr Ile Val Ile Glu
            260                 265                 270
```

```
<210> SEQ ID NO 14
<211> LENGTH: 294
<212> TYPE: PRT
<213> ORGANISM: Chlorobaculum tepidum

<400> SEQUENCE: 14
```

Met Lys Leu Asp Leu Asp Ala Phe Arg Ile Gln Pro Gly Lys Lys Pro
1               5                   10                  15

Asn Leu Ala Lys Arg Pro Thr Arg Ile Asp Pro Val Tyr Arg Ser Lys
            20                  25                  30

Gly Glu Tyr His Glu Leu Leu Ala Asn His Val Ala Glu Leu Ser Lys
        35                  40                  45

Leu Gln Asn Val Leu Tyr Ala Asp Asn Arg Tyr Ala Ile Leu Leu Ile
    50                  55                  60

Phe Gln Ala Met Asp Ala Ala Gly Lys Asp Ser Ala Ile Lys His Val
65                  70                  75                  80

Met Ser Gly Val Asn Pro Gln Gly Cys Gln Val Tyr Ser Phe Lys His
                85                  90                  95

Pro Ser Ala Thr Glu Leu Glu His Asp Phe Leu Trp Arg Thr Asn Cys
            100                 105                 110

Val Leu Pro Glu Arg Gly Arg Ile Gly Ile Phe Asn Arg Ser Tyr Tyr
        115                 120                 125

Glu Glu Val Leu Val Val Arg Val His Pro Glu Ile Leu Glu Met Gln
    130                 135                 140

Asn Ile Pro His Asn Leu Ala His Asn Gly Lys Val Trp Asp His Arg
145                 150                 155                 160

Tyr Arg Ser Ile Val Ser His Glu Gln His Leu His Cys Asn Gly Thr
                165                 170                 175

Arg Ile Val Lys Phe Tyr Leu His Leu Ser Lys Glu Glu Gln Arg Lys
            180                 185                 190

Arg Phe Leu Glu Arg Ile Asp Asp Pro Asn Lys Asn Trp Lys Phe Ser
        195                 200                 205

Thr Ala Asp Leu Glu Glu Arg Lys Phe Trp Asp Gln Tyr Met Glu Ala
    210                 215                 220

Tyr Glu Ser Cys Leu Gln Glu Thr Ser Thr Lys Asp Ser Pro Trp Phe
225                 230                 235                 240

Ala Val Pro Ala Asp Asp Lys Lys Asn Ala Arg Leu Ile Val Ser Arg
                245                 250                 255

Ile Val Leu Asp Thr Leu Glu Ser Leu Asn Leu Lys Tyr Pro Glu Pro
            260                 265                 270

Ser Pro Glu Arg Arg Lys Glu Leu Leu Asp Ile Arg Lys Arg Leu Glu
        275                 280                 285

Asn Pro Glu Asn Gly Lys
        290

```
<210> SEQ ID NO 15
<211> LENGTH: 269
<212> TYPE: PRT
<213> ORGANISM: Oceanithermus profundus

<400> SEQUENCE: 15
```

Met Asp Val Ser Arg Tyr Arg Val Pro Pro Gly Ser Gly Phe Asp Pro
1               5                   10                  15

Glu Ala Trp Pro Thr Arg Glu Asp Asp Phe Ala Gly Gly Lys Lys
            20                  25                  30

Glu Ala Lys Lys Glu Leu Ala Arg Leu Ala Val Arg Leu Gly Glu Leu

```
            35                  40                  45
Gln Ala Arg Leu Tyr Ala Glu Gly Arg Gln Ala Leu Leu Ile Val Leu
     50                  55                  60
Gln Gly Met Asp Thr Ala Gly Lys Asp Gly Thr Ile Arg His Val Phe
65                  70                  75                  80
Arg Ala Val Asn Pro Gln Gly Val Arg Val Thr Ser Phe Lys Lys Pro
                 85                  90                  95
Thr Ala Leu Glu Leu Ala His Asp Tyr Leu Trp Arg Val His Arg His
            100                 105                 110
Ala Pro Ala Arg Gly Glu Ile Gly Ile Phe Asn Arg Ser His Tyr Glu
            115                 120                 125
Asp Val Leu Val Arg Val His Glu Leu Val Pro Pro Glu Val Trp
        130                 135                 140
Gly Arg Arg Tyr Asp His Ile Asn Ala Phe Glu Arg Leu Leu Ala Asp
145                 150                 155                 160
Glu Gly Thr Arg Ile Val Lys Phe Phe Leu His Ile Ser Lys Asp Glu
                165                 170                 175
Gln Lys Arg Arg Leu Glu Ala Arg Leu Glu Asn Pro Arg Lys His Trp
            180                 185                 190
Lys Phe Asn Pro Ala Asp Leu Ser Glu Arg Ala Arg Trp Gly Asp Tyr
            195                 200                 205
Ala Ala Ala Tyr Ala Glu Ala Leu Ser Arg Thr Ser Ser Asp Arg Ala
        210                 215                 220
Pro Trp Tyr Ala Val Pro Ala Asp Arg Lys Trp Gln Arg Asn Arg Ile
225                 230                 235                 240
Val Ala Gln Val Leu Val Asp Ala Leu Glu Ala Met Asp Pro Arg Phe
                245                 250                 255
Pro Arg Val Asp Phe Asp Pro Ala Ser Val Arg Val Glu
            260                 265

<210> SEQ ID NO 16
<211> LENGTH: 290
<212> TYPE: PRT
<213> ORGANISM: Roseiflexus castenholzii

<400> SEQUENCE: 16

Met Tyr Ala Gln Arg Val Val Pro Gly Met Arg Val Arg Leu His Asp
1               5                   10                  15
Ile Asp Pro Asp Ala Asn Gly Gly Leu Asn Lys Asp Glu Gly Arg Ala
                20                  25                  30
Arg Phe Ala Glu Leu Asn Ala Glu Leu Asp Val Met Gln Glu Glu Leu
            35                  40                  45
Tyr Ala Ala Gly Ile His Ala Leu Leu Leu Ile Leu Gln Gly Met Asp
        50                  55                  60
Thr Ala Gly Lys Asp Gly Ala Ile Arg Asn Val Met Leu Asn Leu Asn
65                  70                  75                  80
Pro Gln Gly Cys Arg Val Glu Ser Phe Lys Val Pro Thr Glu Glu Glu
                85                  90                  95
Leu Ala His Asp Phe Leu Trp Arg Val His Arg Val Val Pro Arg Lys
            100                 105                 110
Gly Met Val Gly Val Phe Asn Arg Ser His Tyr Glu Asp Val Leu Val
            115                 120                 125
Val Arg Val His Ser Leu Val Pro Glu Ser Val Trp Arg Ala Arg Tyr
        130                 135                 140
```

```
Asp Gln Ile Asn Ala Phe Glu Arg Leu Leu Ala Asp Thr Gly Thr Ile
145                 150                 155                 160

Ile Val Lys Cys Phe Leu His Ile Ser Lys Glu Gln Glu Gln Arg
                165                 170                 175

Leu Leu Ala Arg Glu Arg Asp Val Ser Lys Ala Trp Lys Leu Ser Ala
            180                 185                 190

Gly Asp Trp Arg Glu Arg Ala Phe Trp Asp Asp Tyr Met Ala Ala Tyr
        195                 200                 205

Glu Glu Ala Leu Thr Arg Cys Ser Thr Asp Tyr Ala Pro Trp Tyr Ile
    210                 215                 220

Ile Pro Ala Asn Arg Lys Trp Tyr Arg Asp Leu Ala Ile Ser Glu Ala
225                 230                 235                 240

Leu Val Glu Thr Leu Arg Pro Tyr Arg Asp Asp Trp Arg Arg Ala Leu
                245                 250                 255

Asp Ala Met Ser Arg Ala Arg Arg Ala Glu Leu Glu Ala Phe Arg Ala
            260                 265                 270

Glu Gln His Ala Met Glu Gly Arg Pro Gln Gly Ala Gly Gly Val Ser
        275                 280                 285

Arg Arg
    290

<210> SEQ ID NO 17
<211> LENGTH: 282
<212> TYPE: PRT
<213> ORGANISM: Roseiflexus sp.

<400> SEQUENCE: 17

Met His Tyr Ala His Thr Val Ile Pro Gly Thr Gln Val Arg Leu Arg
1               5                   10                  15

Asp Ile Asp Pro Asp Ala Ser Gly Gly Leu Thr Lys Asp Glu Gly Arg
            20                  25                  30

Glu Arg Phe Ala Ser Phe Asn Ala Thr Leu Asp Ala Met Gln Glu Glu
        35                  40                  45

Leu Tyr Ala Ala Gly Val His Ala Leu Leu Ile Leu Gln Gly Met
    50                  55                  60

Asp Thr Ala Gly Lys Asp Gly Ala Ile Arg Asn Val Met His Asn Leu
65                  70                  75                  80

Asn Pro Gln Gly Cys Arg Val Glu Ser Phe Lys Val Pro Thr Glu Glu
                85                  90                  95

Glu Leu Ala His Asp Phe Leu Trp Arg Val His Lys Val Val Pro Arg
            100                 105                 110

Lys Gly Met Val Gly Val Phe Asn Arg Ser His Tyr Glu Asp Val Leu
        115                 120                 125

Val Val Arg Val His Ser Leu Val Pro Glu His Val Trp Arg Ala Arg
    130                 135                 140

Tyr Asp Gln Ile Asn Ala Phe Glu Arg Leu Leu Thr Asp Thr Gly Thr
145                 150                 155                 160

Ile Ile Val Lys Cys Phe Leu His Ile Ser Lys Asp Glu Gln Glu Lys
                165                 170                 175

Arg Leu Leu Ala Arg Glu Gln Asp Val Thr Lys Ala Trp Lys Leu Ser
            180                 185                 190

Ala Gly Asp Trp Arg Glu Arg Glu Arg Trp Asp Glu Tyr Met Ala Ala
        195                 200                 205

Tyr Glu Glu Ala Leu Thr Arg Cys Ser Thr Glu Tyr Ala Pro Trp Tyr
    210                 215                 220
```

Ile Ile Pro Ala Asn Arg Lys Trp Tyr Arg Asp Leu Ala Ile Ser Glu
225                 230                 235                 240

Val Leu Val Glu Thr Leu Arg Pro Tyr Arg Asp Asp Trp Gln Arg Ala
                245                 250                 255

Leu Asp Ala Met Ser Gln Ala Arg Leu Ala Glu Leu Lys Ala Phe Arg
            260                 265                 270

His Gln Gln Thr Ala Gly Ala Thr Arg Leu
        275                 280

<210> SEQ ID NO 18
<211> LENGTH: 274
<212> TYPE: PRT
<213> ORGANISM: Truepera radiovictrix

<400> SEQUENCE: 18

Met Ser Gln Gly Ser Ala Lys Gly Leu Gly Lys Leu Asp Lys Lys Val
1               5                   10                  15

Tyr Ala Arg Glu Leu Ala Leu Leu Gln Leu Glu Leu Val Lys Leu Gln
            20                  25                  30

Gly Trp Ile Lys Ala Gln Gly Leu Lys Val Val Leu Phe Glu Gly
        35                  40                  45

Arg Asp Ala Ala Gly Lys Gly Ser Thr Ile Thr Arg Ile Thr Gln Pro
50                  55                  60

Leu Asn Pro Arg Val Cys Arg Val Val Ala Leu Gly Ala Pro Thr Glu
65                  70                  75                  80

Arg Glu Arg Thr Gln Trp Tyr Phe Gln Arg Tyr Val His His Leu Pro
                85                  90                  95

Ala Ala Gly Glu Met Val Leu Phe Asp Arg Ser Trp Tyr Asn Arg Ala
            100                 105                 110

Gly Val Glu Arg Val Met Gly Phe Cys Thr Glu Ala Glu Tyr Arg Glu
        115                 120                 125

Phe Leu His Ala Cys Pro Thr Phe Glu Arg Leu Leu Asp Ala Gly
130                 135                 140

Ile Ile Leu Ile Lys Tyr Trp Phe Ser Val Ser Ala Ala Glu Gln Glu
145                 150                 155                 160

Arg Arg Met Arg Arg Asn Glu Asn Pro Ala Lys Arg Trp Lys Leu
                165                 170                 175

Ser Pro Met Asp Leu Glu Ala Arg Ala Arg Trp Val Ala Tyr Ser Lys
            180                 185                 190

Ala Lys Asp Ala Met Phe Tyr His Thr Asp Thr Lys Ala Ser Pro Trp
        195                 200                 205

Tyr Val Val Asn Ala Glu Asp Lys Arg Arg Ala His Leu Ser Cys Ile
210                 215                 220

Ala His Leu Leu Ser Leu Ile Pro Tyr Glu Asp Leu Thr Pro Pro
225                 230                 235                 240

Leu Glu Met Pro Pro Arg Asp Leu Ala Gly Ala Asp Glu Gly Tyr Glu
                245                 250                 255

Arg Pro Asp Lys Ala His Gln Thr Trp Val Pro Asp Tyr Val Pro Pro
            260                 265                 270

Thr Arg

<210> SEQ ID NO 19
<211> LENGTH: 26
<212> TYPE: PRT
<213> ORGANISM: Artificial Sequence

```
<220> FEATURE:
<223> OTHER INFORMATION: Synthetic Polypeptide

<400> SEQUENCE: 19

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 20
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 20

Met Lys Gln Ser Thr Ile Ala Leu Ala Leu Leu Pro Leu Leu Phe Thr
1               5                   10                  15

Pro Val Thr Lys Ala
            20

<210> SEQ ID NO 21
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 21

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 22
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 22

Met Asn Lys Lys Val Leu Thr Leu Ser Ala Val Met Ala Ser Met Leu
1               5                   10                  15

Phe Gly Ala Ala Ala His Ala
            20

<210> SEQ ID NO 23
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 23

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 24
<211> LENGTH: 19
<212> TYPE: PRT
```

```
<213> ORGANISM: Artificial Sequence
<220> FEATURE:
<223> OTHER INFORMATION: Synthetic Polypeptide

<400> SEQUENCE: 24

Met Lys Lys Ile Trp Leu Ala Leu Ala Gly Leu Val Leu Ala Phe Ser
1               5                   10                  15

Ala Ser Ala

<210> SEQ ID NO 25
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 25

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 26
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 26

Met Lys Gln Ala Leu Arg Val Ala Phe Gly Phe Leu Ile Leu Trp Ala
1               5                   10                  15

Ser Val Leu His Ala
            20

<210> SEQ ID NO 27
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 27

Met Arg Val Leu Leu Phe Leu Leu Leu Ser Leu Phe Met Leu Pro Ala
1               5                   10                  15

Phe Ser

<210> SEQ ID NO 28
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 28

Met Ala Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala
        35
```

CELL-FREE PRODUCTION OF RIBONUCLEIC ACID

RELATED APPLICATIONS

This application claims the benefit under 35 U.S.C. § 119(e) of U.S. provisional application No. 62/319,220 filed Apr. 6, 2016 and U.S. provisional application No. 62/452,550 filed Jan. 31, 2017, each of which is incorporated by reference herein in its entirety.

BACKGROUND OF THE INVENTION

Ribonucleic acid (RNA) is ubiquitous to life. RNA acts as the key messenger of information in cells, carrying the instructions from DNA for the regulation and synthesis of proteins. RNA is of interest in biotechnology as synthetically modulating mRNA levels in cells (positively through the introduction of mRNA or negatively through the introduction of siRNA or dsRNA) has applications in fields such as agricultural crop protection, anti-cancer therapeutics, and vaccines. RNA interference (RNAi), for example, refers to a cellular mechanism that uses the DNA sequence of a gene to turn the gene "off"—a process referred to as "silencing." In a wide variety of organisms, including animals, plants, and fungi, RNAi is triggered by double-stranded RNA (dsRNA). Functional single-stranded (e.g. mRNA) and double-stranded RNA molecules have been produced in living cells and in vitro using purified, recombinant enzymes and purified nucleotide triphosphates (see, e.g., European Patent No. 1631675 and U.S. Patent Application Publication No. 2014/0271559 A1, each of which is incorporated herein by reference). Nonetheless, the production of RNA at scales enabling widespread commercial application is currently cost-prohibitive.

SUMMARY OF THE INVENTION

Provided herein are methods, compositions, cells, constructs, and systems for the production (biosynthesis) of RNA. Generally, polymeric RNA from a biomass material is enzymatically depolymerized into its constituent monomers, these monomers are then phosphorylated to their cognate triphosphorylated variants (via a series of kinases) which are subsequently polymerized into a polymeric RNA using a corresponding nuclei acid (e.g., DNA) template.

In some embodiments, the methods, compositions, cells, constructs, and systems of the present disclosure are used for the production of RNA under cell-free conditions, for example, using at least one cell lysate, a combination of purified proteins, or a combination of cell lysate(s) and purified protein(s). The present disclosure is based, in some embodiments, on the conversion of RNA from biomass (e.g., endogenous cellular RNA) to desired synthetic RNA (e.g., synthetic single-stranded or double-stranded RNA) using a cell lysate. First, RNA from biomass (e.g., endogenous RNA), such as messenger RNA (mRNA), transfer RNA (tRNA), and/or ribosomal RNA (rRNA) (e.g., present in a cell lysate) is depolymerized into its monomeric form, 5'-nucleoside monophosphates (NMPs) by one or more nucleases (FIG. 1, reaction 1). Next, these nucleases, as well as native nucleases and phosphatases, are inactivated or partially inactivated (e.g., via heat inactivation), and the NMPs are phosphorylated to ribonucleotide triphosphates (NTPs) by a series of thermostable kinase activities (FIG. 1, reaction 2). Finally, the NTPs are polymerized by a RNA polymerase (e.g., thermostable RNA polymerase) to form a desired RNA, using a nucleic acid (e.g., DNA) template (FIG. 1, reaction 3). The desired synthetic RNA optionally may be purified from the cell lysate.

Thus, some aspects of the present disclosure provide cell-free methods of producing (biosynthesizing) ribonucleic acid (RNA), the methods comprising: (a) incubating at least one cell lysate mixture that comprises (i) RNA and (ii) at least one enzymatic activity selected from the group consisting of enzymatic activities that depolymerize RNA, thermostable kinase activities, and thermostable RNA polymerase activities, under conditions that result in depolymerization of RNA to produce a cell lysate mixture that comprises nucleoside monophosphates; (b) heating the cell lysate mixture produced in step (a) to a temperature (e.g., 50-80° C.) that inactivates or partially inactivates endogenous nucleases and phosphatases without completely inactivating the thermostable kinase activities and thermostable RNA polymerase activities, to produce a cell lysate mixture that comprises heat-inactivated nucleases and phosphatases; and (c) incubating the cell lysate mixture produced in step (b) in the presence of an energy source (e.g., an ATP regeneration system) and a deoxyribonucleic acid (DNA) template (e.g., containing a promoter operably linked to a nucleotide sequence encoding a RNA of interest), under conditions that result in production of nucleoside triphosphates and polymerization of the nucleoside triphosphates to produce a cell lysate mixture that comprises the RNA of interest.

The cell lysate mixture may comprise a single cell lysate obtained from cells that comprise RNA and express at least one enzyme (including at least one fusion enzyme) that acts as a ribonuclease, acts as a kinase, and/or acts as a RNA polymerase. Alternatively, the cell lysate mixture may comprise at least two (e.g., at least 3, 4, 5, or 6) cell lysates, wherein at least one cell lysate is obtained from cells that comprise RNA, and at least one cell lysate (e.g., at least 2, 3, 4, or 5) is obtained from cells that express at least one enzyme that acts as a nuclease, acts as a kinase, and/or acts as a RNA polymerase.

An enzyme or fusion enzyme is considered to "act as a nuclease" if the enzyme of fusion enzyme exhibits nuclease activity (cleaves or depolymerizes a nucleic acid; e.g., RNase R). An enzyme or fusion enzyme is considered to "act as a kinase" if the enzyme of fusion enzyme exhibits kinase activity (catalyzes the transfer of a phosphate group from one molecule to another molecule: e.g. polyphosphate kinase). An enzyme or fusion enzyme is considered to "act as a polymerase" if the enzyme of fusion enzyme exhibits polymerase activity (assembles nucleotides to produce nucleic acids; e.g., RNA polymerase).

In some embodiments, the RNA of step (a) is messenger RNA (mRNA), transfer RNA (tRNA), or ribosomal RNA (rRNA).

In some embodiments, the cell lysate mixture comprises at least one ribonuclease, at least one thermostable kinase, and/or at least one RNA polymerase (e.g., a thermostable RNA polymerase). The use of fusion enzymes is also encompassed by the present disclosure. For example the cell lysate mixture may comprise a fusion of a ribonuclease and a kinase, or a fusion of multiple kinases. Other fusion enzymes are encompassed by the present disclosure.

Other aspects of the present disclosure provide engineered cells, cell lysates, and cell lysate mixtures comprising at least one nucleoside monophosphate kinase (e.g., thermostable nucleoside monophosphate kinase), at least one nucleoside diphosphate kinase (e.g., thermostable nucleoside diphosphate kinase), and at least one polyphosphate kinase (e.g., thermostable polyphosphate kinase). The cells, in some embodiments, may also comprise at least one ribonuclease and/or at least one RNA polymerase (e.g., thermostable RNA polymerase).

In some embodiments, methods of producing (biosynthesizing) RNA comprise (a) lysing cultured cells (e.g., engineered cells) that comprise RNA (e.g., mRNA, tRNA, and/or rRNA), RNase R, thermostable kinases (e.g., PfPyrH. TthAdk, TthCmk, PfGmk, AaNdk, TePpk, and/or PPK2 (e.g., see Table 6), and a thermostable T7 RNA polymerase, thereby producing a cell lysate, (b) incubating the cell lysate produced in step (a) under conditions that result in depolymerization of RNA to 5'-NMPs, thereby producing a cell lysate that comprises 5'-NMPs, (c) heating the cell lysate produced in step (b) to 60-80° C. to inactivate endogenous nucleases and phosphatases without completely inactivating the thermostable kinases and thermostable RNA polymerase, thereby producing a cell lysate that comprises heat-inactivated nucleases and phosphatases, and (d) incubating the cell lysate produced in step (c) in the presence of an energy source (e.g., an ATP regeneration system comprising polyphosphate) and an engineered nucleic acid (e.g., DNA) template (e.g., containing a promoter operably linked to a nucleotide sequence encoding a RNA of interest), under conditions that result in production of nucleoside triphosphates and polymerization of the nucleoside triphosphates to produce the RNA of interest.

In some embodiments, the RNA, RNase R, thermostable kinases, and thermostable T7 RNA polymerase are contained in a single strain of cultured cells (e.g., engineered cells). In other embodiments, cultured cells (e.g., engineered cells) containing a subset of the above activities/components are lysed, and the lysates combined to generate a cell lysate mixture that comprises all the enzymatic activities described in step (a) above. In some embodiments, enzymatic activities, in the form of purified enzymes, are added to the lysates described in step (a) above. In some embodiments, lysates and/or purified proteins are combined before the heat-inactivation step described in step (c) above. In other embodiments, lysates and/or purified proteins are combined after the heat inactivation step described in step (c) above.

The RNA of interest may be any form of RNA, including single-stranded RNA and double-stranded RNA. For example, the RNA of interest may be messenger RNA (mRNA), antisense RNA, micro RNA, small interfering RNA (siRNA), or a short hairpin RNA (shRNA). Other RNA interference (RNAi) molecules are encompassed herein.

The details of several embodiments of the invention are set forth in the accompanying Figures and the Detailed Description. Other features, objects, and advantages of the invention will be apparent from the description and from the claims.

BRIEF DESCRIPTION OF THE DRAWINGS

(FIG. 5A) Release of acid-soluble nucleotides (mononucleotides and short oligonucleotides) with nuclease treatment was most rapid with Benzonase, RNase A, RNase R, and Nuclease P1. (FIG. 5B) LC-MS analysis of reaction products demonstrated NMP release from RNA with RNase R and Nuclease P1 treatment.

(FIG. 7A) SDS-PAGE analysis of protein expression in duplicate cultures. Empty vector cultures contained an empty protein expression vector (pETDuet-1). RNase R cultures contained *E. coli* rnr cloned into pETDuet-1. Samples from induced cultures (+) exhibited strong expression of RNase R (MW 92.9 kDa with C-terminal hexahistidine tag) indicated by arrow at right. (FIG. 7B) Growth kinetics (encompassing pre- and post-induction growth) of Empty Vector (dark gray) and RNase R-expressing strains (light gray) demonstrated that RNase R overexpression was not deleterious to cell growth. Dashed lines represent exponential curve fits. (FIG. 7C) Overexpressed RNase R was active in lysates of batch-grown biomass, releasing acid-soluble nucleotides. In the empty vector strain (solid dark gray line), adding exogenous RNase R increased the rate of nucleotide release (dashed dark gray line). In contrast, strains expressing RNase R exhibited rapid nucleotide release upon lysis (solid light gray line). Adding exogenous RNase R did not increase rates of nucleotide release or final nucleotide yields (dashed light gray line). Experiments were performed at a final concentration of 50% lysate.

(FIG. 9A) hAMP was relatively stable in lysates, with 90% remaining after a 1 hour incubation at 37° C. (FIG. 9B) hCMP was degraded in lysates, with 70% remaining after approximately 30 minutes. Addition of 10 mM sodium orthovanadate (dotted line) (an inhibitor of several phosphatases and kinases) significantly improved stability. (FIG. 9C) hUMP was degraded in lysates, with 70% remaining after approximately 20 minutes. Sodium phosphate (150 mM) (dashed line) and sodium orthovanadate (dotted line) significantly improved stability. (FIG. 9D) hGMP was degraded in lysates, with 70% remaining after approximately 10 minutes. Sodium orthovanadate significantly improved stability, with 70% hGMP remaining after 30 minutes.

(FIG. 11A) Heat inactivation stabilized NMPs in lysates. Lysates were treated with exogenous RNase R (Lysate+RNase R) (t=0 min–5 min) at 37° C. to release NMPs, then heat inactivated (t=5 min to 25 min) at 70° C. The temperature was then lowered to 37° C. and the reaction was incubated for an additional 60 min. NMPs were largely stable in lysates after heat inactivation. (FIG. 11B) Heat inactivation stabilized reactants and products of transcription reactions in lysates. Lysates were pre-incubated for 15 minutes at the indicated temperature, then the temperature was lowered to 37° C. and transcription reactants were added. Heat inactivation at 70° C. and 80° C., but not 60° C. stabilized substrates and products sufficiently to produce a detectable transcription product similar to the positive control (no lysate).

in FIG. 3B).

DETAILED DESCRIPTION OF CERTAIN EMBODIMENTS OF THE INVENTION

Figure 1:
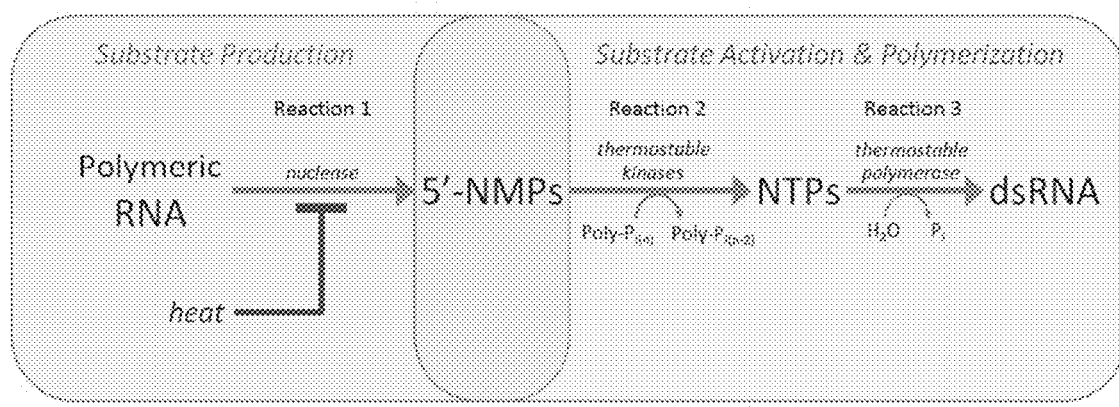
FIG. 1 shows a schematic of cell-free RNA production as described herein. Cells containing RNA from biomass (e.g., endogenous RNA), a nuclease, a thermostable kinase, and/or a thermostable RNA polymerase are lysed (or combined and lysed), and the resulting cell lysate(s) is/are incubated under conditions that result in depolymerization of the RNA. The cell lysate is then heated to inactivate the nuclease and any endogenous phosphatases (without inactivating the thermostable kinase and thermostable RNA polymerase). The cell lysate is then incubated in the presence of an engineered DNA template that encodes a RNA of interest, under conditions that result in production of nucleoside triphosphates and polymerization of the nucleoside triphosphates, thereby producing a RNA of interest (e.g., ssRNA or dsRNA). Alternatively, individual, purified pathway enzymes (e.g., RNA polymerase, such as thermostable RNA polymerase) may be added to the cell lysate following the heat inactivation step. Thus, in some instances, the engineered cells used to produce the cell lysate do not express one or more of the enzymatic activities described above, e.g., a nuclease, a thermostable kinase and/or a thermostable RNA polymerase.

Provided herein, in some aspects, are methods, compositions, cells, constructs, and systems for the cell-free production (biosynthesis) of nucleic acid (e.g., RNA or DNA). In some embodiments, a single type of organism (e.g., a population of bacterial cells) is engineered to express at least one nuclease, at least one thermostable kinases and at least one thermostable polymerase (e.g., RNA or DNA polymerase). The engineered cells are grown (cultured) under conditions that result in enzyme expression. In some embodiments, the engineered cells may be grown to a desired cell density, and then expression of certain enzymes may be induced (activated). Thus, transcription of certain enzymes may be under the control of an inducible promoter. The cells (e.g., engineered and/or non-engineered cells) are then lysed (e.g., mechanically, chemically, or enzymatically disrupted) to produce a cell lysate that comprises the enzymatic activities required for cell-free production of RNA (e.g., ssRNA or dsRNA). In some embodiments, cells containing polymeric RNA (e.g., mRNA, tRNA, and/or rRNA) are mixed with the engineered cells containing pathway enzymes prior to the cell lysis step. In other embodiments, cell lysate(s) obtained from cells containing polymeric RNA is combined (mixed) with cell lysate(s) obtained from engineered cells containing pathway enzymes. In yet other embodiments, one or more purified pathway enzymes are combined (mixed) with cell lysate(s) obtained from engineered cells. "Pathway enzymes" are enzymes required to biosynthesize the RNA of interest (e.g., starting from polymeric RNA).

To synthesize RNA, the cell lysate (or cell lysate mixture) is incubated under conditions that result in nuclease-mediated (e.g., RNase-mediated) depolymerization of the host-derived (endogenous) RNA to a desired yield of 5'-nucleoside monophosphates (NMPs, or nucleoside monophosphates). The cell lysate (or cell lysate mixture) is then heated, in some embodiments, to inactivate the majority of host-derived enzymes, including phosphatases and nucleases (e.g., RNases), as well as any exogenous nuclease(s) previously added to the cell lysate to facilitate depolymerization of the host-derived RNA. Following the heat inactivation step, the cell lysate is incubated under conditions that result in phosphorylation of the NMPs to NTPs (nucleoside triphosphates) by thermostable kinases (e.g., thermostable nucleoside monophosphate kinases and nucleoside diphosphate kinases) using, for example, thermostable polyphosphate kinase and the addition of polyphosphate as the energy source. The resulting NTPs are subsequently polymerized to RNA by a RNA polymerase (e.g., thermostable RNA polymerase) using an engineered template (e.g., DNA template) present in the lysates (e.g., either expressed by the engineered cells and included as a cellular component of the cell lysate, or later added to the cell lysate).

Cell-Free Production

"Cell-free production" is the use of biological processes for the synthesis of a biomolecule or chemical compound without using living cells. The cells are lysed and unpurified (crude) portions or partially-purified portions, both containing enzymes, are used for the production of a desired product. Purified enzymes may be added to cell lysates, in some embodiments. As an example, cells are cultured, harvested, and lysed by high-pressure homogenization or other cell lysis method (e.g., chemical cell lysis). The cell-free reaction may be conducted in a batch or fed-batch mode. In some instances, the enzymatic pathways fill the working volume of the reactor and may be more dilute than the intracellular environment. Yet substantially all of the cellular catalysts are provided, including catalysts that are membrane associated. The inner membrane is fragmented during cell lysis, and the fragments of these membranes may form membrane vesicles. See, e.g., Swartz, *AIChE Journal*, 2012, 58(1), 5-13, incorporated herein by reference.

Cell-free methods, compositions, and systems of the present disclosure utilize cell lysates (e.g., crude or partially purified cell lysates), discussed in greater detail herein. Cell lysates prepared, for example, by mechanical means (e.g., shearing or crushing), are distinct from chemically-permeabilized cells. As discussed above, in some embodiments, during cell lysis (e.g., mechanical cell lysis), the inner cell membrane is fragmented such that inverted membrane vesicles are formed in the cell lysates. Such inverted membrane vesicles are not produced through chemical cell permeabilization methods. Cells that are lysed (e.g., at least 75%, 80%, 85%, 90%, or 95%) are no longer intact. Thus, permeabilized cells, which are intact cells containing perforations (small holes) are not considered lysed cells.

While the methods provided herein are generally cell-free and use cell lysates, in some embodiments, it may be advantageous, at least for some steps of the methods, to use permeabilized cells. Thus, the present disclosure does not exclude the use of permeabilized cells in at least one step of the RNA production methods.

It should be understood that while many of the embodiments described herein refer to "lysing cultured cells" that comprise particular enzymes, the phrase is intended to encompass lysing a clonal population of cells obtained from a single culture (e.g., containing all the enzymes needed to synthesize RNA) as well as lysing more than one clonal population of cells, each obtained from different cell cultures (e.g., each containing one or more enzymes needed to synthesize RNA and/or the polymeric RNA substrate). For example, in some embodiments, a population of cells (e.g., engineered cells) expressing one thermostable kinase may be cultured together and used to produce one cell lysate, and another population of cells (e.g., engineered cells) expressing a different thermostable kinase may be cultured together and used to produce another cell lysate. These two cell lysates, each comprising a different thermostable kinase, may then be combined for use in a RNA biosynthesis method of the present disclosure.

Depolymerization of Ribonucleic Acid to Nucleoside Monophosphates

The present disclosure is based on the conversion of RNA from biomass (e.g., endogenous cellular RNA) to desired synthetic RNA using a cell lysate through a cell-free process involving a series of enzymatic reactions. First, RNA (e.g., endogenous RNA) present in a cell lysate, derived from host cells, is converted to its constituent monomers by nucleases. RNA from biomass (e.g., endogenous RNA) typically includes ribosomal RNA (rRNA), messenger RNA (mRNA), transfer RNA (tRNA), other RNAs, or a combination thereof. Depolymerization or degradation of RNA results in a pool of 5'-nucleoside monophosphates (5'-NMPs), also referred to simply as "monomers." These monomers, which are converted to nucleoside diphosphates, which are converted to nucleoside triphosphates, are used as starting material for the downstream polymerization/synthesis of a RNA of interest. In some embodiments, the RNA of interest is ssRNA (e.g., mRNA). In some embodiments, the RNA of interest is dsRNA.

The amount of RNA (e.g., endogenous RNA) required to synthesize a RNA of interest may vary, depending on, for example, the desired length and yield of the RNA of interest as well as the nucleotide composition of the RNA relative to the nucleotide composition of the RNA (e.g., endogenous RNA) of the cell (e.g., *E. coli* cell). Typically, for a bacterial cell, for example, RNA (e.g., endogenous RNA) content ranges from 5-50% of the total cell mass. The mass of the starting material can be calculated, for example, using the following equation: (kilogram (kg) of RNA/kilogram of dry cell weight)×100%.

Endogenous RNA may be depolymerized or degraded into its constituent monomers by chemical or enzymatic means. Chemical hydrolysis of RNA, however, typically produces 2'- and 3'-NMPs, which cannot be polymerized into RNA. Thus, the methods, compositions, and systems as provided herein primarily use enzymes for the depolymerization of endogenous RNA. An "enzyme that depolymerizes RNA" catalyzes the hydrolysis of the phosphodiester bonds between two nucleotides in a RNA. Thus, "an enzyme that depolymerizes RNA" converts RNA (polymeric RNA) into its monomeric form-nucleoside monophosphates (NMPs). Depending on the enzyme, enzymatic depolymerization of RNA may yield 3'-NMPs, 5'-NMPs or a combination of 3'-NMPs and 5'-NMPs. Because it is not possible to polymerize 3'-NTPs (converted from 3'-NDPs, which are converted from 3'-NMPs), enzymes (e.g., RNase R) that yield 5'-NMPs (which are then converted to 5'-NDPs, and then 5'-NTPs) are preferred. In some embodiments, enzymes that yield 3'-NMPs are removed from the genomic DNA of the engineered cell to increase efficiency of RNA production. In some embodiments, the enzyme used for RNA depolymerization is RNase R. In some embodiments, the concentration of RNase R used is 0.1-1.0 mg/mL (e.g., 0.1, 0.2, 0.3, 0.4, 0.5, 0.6, 0.7, 0.8, 0.9, or 1.0 mg/mL). In some embodiments, the concentration of RNase R used is 0.4-0.6 mg/mL. In some embodiments, the concentration of RNase R used is 0.5 mg/mL. In some embodiments, the concentration of RNase R used is greater than 1.0 mg/mL.

Examples of enzymes that depolymerize RNA include, without limitation, nucleases, including ribonucleases (RNases, e.g., RNase R) and phosphodiesterases. Nucleases catalyze the degradation of nucleic acid into smaller components (e.g., monomers, also referred to as nucleoside monophosphates, or oligonucleotides). Phosphodiesterases catalyze degradation of phosphodiester bonds. These enzymes that depolymerize RNA may be encoded by full length genes or by gene fusions (e.g., DNA that includes at least two different genes (or fragments of genes) encoding at two different enzymatic activities).

RNase functions in cells to regulate RNA maturation and turn over. Each RNase has a specific substrate preferences-dsRNA or ssRNA. Thus, in some embodiments, a combination of different RNases, or a combination of different nucleases, generally, may be used to depolymerize biomass-derived polymeric RNA (e.g., endogenous RNA). For example, 1-2, 1-3, 1-4, 1-5, 1-6, 1-7, 1-8, 1-9, or 1-10 different nucleases may be used in combination to depolymerize RNA. In some embodiments, at least 1, at least 2, at least 3, at least 4, at least 5, at least 6, at least 7, at least 8, at least 9, or at least 10 different nucleases may be used in combination to depolymerize RNA. Non-limiting examples of nucleases for use as provided herein are included in Table 1. In some embodiments, the nuclease used is RNase R.

TABLE 1

Enzymes that Depolymerize Ribonucleic Acid

| Nuclease | Host Organism(s) | EC # | UniProt | Reference |
|---|---|---|---|---|
| Nuclease P1 (P1 Nuclease) | *Penicillium citrum* | 3.1.30.1 | P24289 | 1, 2, 3 |
| RNase II | *Escherichia coli* | 3.1.13.1 | P30850 | 4, 5 |
| RNase III | *Escherichia coli* | 3.1.26.3 | P0A7Y0 | 6, 7, 8 |
| RNase R | *Pseudomonas putida* or *Escherichia coli* | 3.1.13.— | R9V9M9 P21499 | 9 |
| RNase JI | *Bacillus subtilis* | 3.1.4.1 | Q45493 | 10, 11 |
| NucA | *Serratia marcescens* | 3.1.30.2 | P13717 | 12, 13, 14 |
| RNase T | *Escherichia coli* | 3.1.27.3 | P30014 | 15, 16, 17 |
| RNase E | *Escherichia coli* | 3.1.26.12 | P21513 | 18, 19 |

Enzymes that depolymerize RNA (e.g., RNases) may be endogenous to a host cell (host-derived), or they may be encoded by engineered nucleic acids exogenously introduced into a host cell (e.g., on an episomal vector or integrated into the genome of the host cell).

In some embodiments, engineered nucleic acids encoding enzymes that depolymerize RNA are operably linked to an inducible promoter. Thus, in some embodiments, expression of an engineered nucleic acid encoding an enzyme that depolymerizes RNA is temporally or spatially regulated. For example, nucleic acids may be engineered to encode enzymes (e.g., RNases) that are relocated to or are sequestered in the periplasm of a host cell so that activity of the enzyme does not interfere with cell growth or other metabolic processes. Upon cell lysis, the relocated enzyme is released from the periplasm, brought into contact with the endogenous RNA, and depolymerizes the RNA into monomeric form. See, e.g., International Publication No. WO 2011/140516, published Nov. 10, 2011, incorporated herein by reference.

"Conditions that result in depolymerization of RNA" are known in the art or may be determined by one of ordinary skill in the art, taking into consideration, for example, optimal conditions for nuclease (e.g., RNase) activity, including pH, temperature, length of time, and salt concentration of the cell lysate as well as any exogenous cofactors. Examples including those described previously (see. e.g., Wong, C. H. et al. *J. Am. Chem. Soc.,* 105: 115-117, 1983), EP1587947B1, Cheng Z F. Deutscher M P. *J Biol Chem.* 277:21624-21629, 2002).

In some embodiments, metal ions (e.g., $Mg^{2+}$) are depleted from the depolymerization reaction. In some embodiments, the concentration of metal ion (e.g., $Mg^{2+}$) is 8 mM or less (e.g., less than 8 mM, less than 7 mM, less than 6 mM, less than 5 mM, less than 4 mM, less than 3 mM, less than 2 mM, less than 1 mM, less than 0.5 mM). In some embodiments, the concentration of metal ion (e.g., $Mg^{2+}$) is 0.1 mM-8 mM, 0.1 mM-7 mM, or 0.1 mM-5 mM.

The pH of a cell lysate during a RNA depolymerization reaction may have a value of 3.0 to 8.0. In some embodiments, the pH value of a cell lysate is 3.0-8.0, 4.0-8.0, 5.0-8.0, 6.0-8.0, 7.0-8.0, 3.0-7.0, 4.0-7.0, 5.0-7.0, 6.0-7.0, 3.0-6.0, 4.0-6.0, 5.0-6.0, 3.0-5.0, 3.0-4.0, or 4.0-5.0. In some embodiments, the pH value of a cell lysate is 3.0, 3.5, 4.0, 4.5, 5.0, 5.5, 6.0, 6.5, 7.0, 7.5, or 8.0. In some embodiments, the pH value of a cell lysate is 7.0, 7.1, 7.2, 7.3, 7.4, or 7.5. The pH of a cell lysate may be adjusted, as needed.

The temperature of a cell lysate during a RNA depolymerization reaction may be 15° C. to 70° C. In some embodiments, the temperature of a cell lysate during a RNA depolymerization reaction is 15-60° C., 15-50° C., 15-40° C. 15-30° C., 25-70° C., 25-60° C., 25-50° C., 25-40° C., 30-70° C., 30-60° C., or 30-50° C. In some embodiments, the temperature of a cell lysate during a RNA depolymerization reaction is 37° C. In some embodiments, the temperature of a cell lysate during a RNA depolymerization reaction is 15° C., 25° C., 32° C., 37° C., 40° C., 42° C., 45° C., 50° C., 55° C., 56° C., 57° C., 58° C., 59° C., 60° C., 61° C., 62° C., 63° C. 64° C., 65° C. 66° C., 67° C., 68° C., 69° C., or 70° C.

A cell lysate during a RNA depolymerization reaction may be incubated for 5 minutes (min) to 72 hours (hrs). In some embodiments, a cell lysate during a RNA depolymerization reaction is incubated for 5-10 min, 5-15 min, 5-20 min, 5-30 min, or 5 min-48 hrs. For example, a cell lysate during a RNA depolymerization reaction may be incubated for 5 min, 10 min, 15 min, 20 min. 25 min, 30 min, 45 min, 1 hr, 2 hrs. 3 hrs, 4 hrs, 5 hrs, 6 hrs, 7 hrs, 8 hrs, 9 hrs, 10 hrs, 11 hrs, 12 hrs, 18 hrs, 24 hrs, 30 hrs, 36 hrs. 42 hours, or 48 hours. In some embodiments, a cell lysate during a RNA depolymerization reaction is incubated for 24 hours at a temperature of 37° C. In some embodiments, a cell lysate during a RNA depolymerization reaction is incubated for 5-10 min at a temperature of 37° C. In some embodiments, a cell lysate during a RNA depolymerization reaction has a pH of 7.0 and is incubated for 15 minutes at a temperature of 37° C. In some embodiments, a cell lysate during a RNA depolymerization reaction may be incubated under conditions that result in greater than 65% conversion of RNA to 5'-NMPs. In some embodiments, RNA is converted to 5'-NMPs at a rate of (or at least) 50 mM/hr, 100 mM/hr or 200 mM/hr.

In some embodiments, salt is added to a cell lysate, for example, to prevent enzyme aggregation. For example, sodium chloride, potassium chloride, sodium acetate, potassium acetate, or a combination thereof, may be added to a cell lysate. The concentration of salt in a cell lysate during a RNA depolymerization reaction may be 5 mM to 1 M. In some embodiments, the concentration of salt in a cell lysate during a RNA depolymerization reaction 5 mM, 10 mM, 15 mM, 20 mM, 25 mM, 50 mM, 100 mM, 150 mM, 200 mM, 250 mM, 500 mM, 750 mM, or 1 M. In some embodiments, the cell lysate comprises a mixture that includes 40-60 mM potassium phosphate, 1-5 mM $MnCl_2$, and/or 10-50 mM $MgCl_2$ (e.g., 20 mM $MgCl_2$).

In some embodiments, buffer is added to a cell lysate, for example, to achieve a particular pH value and/or salt concentration. Examples of buffers include, without limitation, phosphate buffer, Tris buffer, MOPS buffer, HEPES buffer, citrate buffer, acetate buffer, malate buffer, MES buffer, histidine buffer, PIPES buffer, bis-tris buffer, and ethanolamine buffer.

Depolymerization of RNA results in the production of 5'-NMP, including 5'-AMP, 5'-UMP, 5'-CMP, and 5'-GMP. While the NMP may be present in the cell lysate at relatively equimolar amounts, depolymerization of RNA does not result in any predetermined ratio of NMPs.

In some embodiments, 50-98% of the endogenous RNA in a cell upon lysis is converted to (depolymerized to) 5'-NMPs. For example, 50-95%, 50-90%, 50-85%, 50-80%, 75-98%, 75-95%, 75-90%, 75-85% or 75-80% RNA is converted to (depolymerized to) 5'-NMPs. In some embodiments, 65-70% of the endogenous RNA in a cell upon lysis is converted to (depolymerized to) 5'-NMPs. Lower yields are also acceptable.

Elimination of Futile Cycles

Following conversion of RNA from biomass (e.g., endogenous RNA) to its monomeric constituents by endogenous and/or exogenous nucleases, there typically remains in the cell lysate several enzymes, including nucleases and phosphatases, which may have deleterious effects on RNA biosynthesis. For example, *Escherichia coli* has numerous phosphatases, many of which dephosphorylate NTPs, NDPs, and NMPs. Dephosphorylation of NMPs following RNA depolymerization results in the accumulation of the non-phosphorylated nucleosides and a loss of usable NMP substrate, thus reducing synthetic RNA yield. Dephosphorylation of NMPs. NDPs, or NTPs following RNA depolymerization results in futile energy cycles (energy cycles that produce a low yield of synthetic RNA) during which NMPs are phosphorylated to NDPs and NTPs, which in turn are dephosphorylated back to their NMP or nucleoside starting point. Futile cycles reduce the yield of RNA product per unit energy input (e.g., polyphosphate, ATP, or other sources of high energy phosphate). In some embodiments, the enzymatic activities are eliminated by removal from the host genome. In some embodiments, the enzymatic activities are eliminated by heat inactivation. In some embodiments, the enzymatic activities are eliminated by protease targeting. In some embodiments the enzymatic activities are eliminated through the use of chemical inhibitors. A combination of any of the foregoing approaches may also be used.

Enzymes deleterious to the biosynthesis of RNA, as provided herein, may be deleted from the host cell genome during the process of engineering the host cell, provided the enzymes are not essential for host cell (e.g., bacterial cell) survival and/or growth. Deletion of enzymes or enzyme activities may be achieved, for example, by deleting or modifying in the host cell genome a gene encoding the essential enzyme. An enzyme is "essential for host cell survival" if the enzyme is necessary for the survival of the host cell. That is, if a host cell cannot survive without expression and/or activity of a particular enzyme, then that enzyme is considered essential for host cell survival. Similarly, an enzyme is "essential for host cell growth" if the enzyme is necessary for the growth of the host cell. That is, if a host cell cannot divide and/or grow without expression and/or activity of a particular enzyme, then that enzyme is considered essential for host cell growth.

If enzymes deleterious to the biosynthesis of RNA are essential for host cell survival and/or growth, then it may not be possible to delete or modify the genes encoding the enzymes. In such instances, the enzymes may be heat inactivated. "Heat inactivation" refers to the process of heating a cell lysate to a temperature sufficient to inactivate (or at least partially inactivate) endogenous nucleases and phosphatases. Generally, the process of heat inactivation involves denaturation of (unfolding of) the deleterious enzyme. The temperature at which endogenous cellular proteins denature varies among organisms. In *E. coli*, for example, endogenous cellular enzymes generally denature at temperatures above 41° C. The denaturation temperature may be higher or lower than 41° C. for other organisms. Enzymes of a cell lysate, as provide here, may be heat inactivated at a temperature of 40° C.-95° C., or higher. In some embodiments, enzymes of a cell lysate may be heat inactivated at a temperature of 40-90° C., 40-80° C., 40-70° C. 40-60° C., 40-50° C., 50-80° C., 50-70° C., 50-60° C., 60-80° C., 60-70° C. or 70-80° C. For example, enzymes of a cell lysate may be heat inactivated at a temperature of 40) C., 42° C., 45° C., 50° C., 55° C., 60° C., 65° C., 70° C., 75° C., 80° C. 85° C., 90° C., or 95° C. In some embodiments, enzymes of a cell lysate may be heat inactivated at a temperature of 50-80° C. In some embodiments, enzymes of a cell lysate may be heat inactivated at a temperature of 70° C. In some embodiments, enzymes of a cell lysate may be heat inactivated at a temperature of 60° C. It may also be possible to introduce chemical inhibitors of deleterious enzymes. Such inhibitors may include, but are not limited to, sodium orthovanadate (inhibitor of protein phosphotyrosyl phosphatases), sodium fluoride (inhibitor of phosphoseryl and phosphothreonyl phosphatases), sodium pyrophosphate (phosphatase inhibitor), sodium phosphate, and/or potassium phosphate.

The period of time during which a cell lysate is incubated at elevated temperatures to achieve heat inactivation of endogenous enzymes may vary, depending, for example, on the volume of the cell lysate and the organism from which the cell lysate was prepared. In some embodiments, a cell lysate is incubated at a temperature of 35° C.-80° C. for 2 minutes (min) to 48 hours (hr). For example, a cell lysate may be incubated at a temperature of 35° C.-80° C. for 2 min, 4 min, 5 min, 10 min, 15 min, 30 min, 45 min, or 1 hr. In some embodiments, a cell lysate is incubated at a temperature of 35° C.-80° C. for 2, 3, 4, 5, 6, 7, 8, 9, 10, 11, 12, 13, 14, 15, 16, 17, 18, 19, 20, 24, 36, 42, or 48 hr.

In some embodiments, enzymes are heat inactivated at a temperature of 60-80° C. for 10-20 min. In some embodiments, enzymes are heat inactivated at a temperature of 70° C. for 15 min.

In some embodiments, enzymes that depolymerize endogenous RNA comprise one or more modifications (e.g., mutations) that render the enzymes more sensitive to heat. These enzymes are referred to as "heat-sensitive enzymes." Heat-sensitive enzymes denature and become inactivated at temperatures lower than that of their wild-type counterparts, and/or the period of time required to reduce the activity of the heat-sensitive enzymes is shorter than that of their wild-type counterparts.

It should be understood that enzymes that are heat inactivated may, in some instances, retain some degree of activity. For example, the activity level of a heat-inactivated enzyme may be less than 50% of the activity level of the same enzyme that has not been heat inactivated. In some embodiments, the activity level of a heat-inactivated enzyme is less than 40%, less than 30%, less than 20%, less than 10%, less than 5%, less than 1%, or less than 0.1% of the activity level of the same enzyme that has not been heat inactivated.

Thus, an enzyme's activity may be completely eliminated or reduced. An enzyme is considered completely inactive if the denatured (heat inactivated) form of the enzyme no longer catalyzes a reaction catalyzed by the enzyme in its native form. A heat-inactivated, denatured enzyme is considered "inactivated" when activity of the heat-inactivated enzyme is reduced by at least 50% relative to activity of the enzyme that is not heated (e.g., in its native environment). In some embodiments, activity of a heat-inactivated enzyme is reduced by 50-100% relative to the activity of the enzyme that is not heated. For example, activity of a heat-inactivated enzyme is reduced by 50-90%, 50-85%, 50-80%, 50-75%, 50-70%, 50-65%, 50-60%, or 50-55% relative to activity of the enzyme that is not heated. In some embodiments, the activity of a heat-inactivated enzyme is reduced by 25%, 30%, 35%, 40%, 45%, 50%, 55%, 60%, 65%, 70%, 75%, 80%, 85%, 90%, 95%, 98%, 99%, or 100% relative to the activity of the enzyme that is not heated.

Examples of enzymes that may be heat inactivated, or deleted from the genome of a host cell, include, without limitation, nucleases (e.g., RNase III, RNase I, RNase R, PNPase, RNase II, and RNase T), phosphatases (e.g., nucleoside monophosphatase, nucleoside diphosphatase, nucleoside triphosphatase), and other enzymes that depolymerize RNA or dephosphorylate nucleotides. Enzymes that depolymerize RNA include any enzyme that is able to cleave, partially hydrolyze, or completely hydrolyze a RNA molecule. Table 2 provides a list of non-limiting examples of nucleases that may be heat inactivated or, in some instances, deleted from an engineered host cell. Table 3 provides a list of non-limiting examples of phosphatases that may be heat inactivated or, in some instances, deleted from an engineered host cell. Heat inactivation of these and other nucleases and phosphatases is encompassed by the present disclosure.

TABLE 2

Examples of Nucleases

| Nuclease | Gene | Function | EC # | Uniprot | Reference |
|---|---|---|---|---|---|
| RNase III | rnc | Cleaves dsRNA, rRNA and some mRNA | 3.1.26.3 | P0A7Y0 | 6, 7, 8 |
| RNase I | rna | General ribonuclease, broad substrate specificity. Localizes to periplasm. | 3.1.27.6 | P21338 | 20 |
| RNase R | rnr | Cleaves some dsRNA, poly-A mRNA, mRNA and rRNA | 3.1.13.— | P21499 | 4, 21 |
| PNPase | pnp | General mRNA degradation, tRNA maturation and degradation. | 3.1.13.1 | P05055 | 22, 23, 24 |
| RNase II | rnb | Exonuclease. Plays a role in tRNA processing | 3.1.13.1 | P30850 | 4, 5 |
| RNase T | rnt | Processing of tRNAs, rRNA and other stable RNAs. Capable of degrading ssDNA and ssRNA. | 3.1.13.— | P30014 | 15, 16, 17 |

TABLE 2-continued

Examples of Nucleases

| Nuclease | Gene | Function | EC # | Uniprot | Reference |
|---|---|---|---|---|---|
| RNase E | rne | Processes rRNA, tRNA and other RNAs. Associates with the "degradasome" | 3.1.26.12 | P21513 | 18, 19 |

TABLE 3

Examples of Phosphatases.

| Phosphatase Class | Host | EC # | Examples | Uniprot | Reference |
|---|---|---|---|---|---|
| NMP/NDP phosphatase | E. coli | 3.1.3.5 3.6.1.6 | AphA PhoA UmpG YrfG UshA UmpH | P0AE22 P00634 P0A840 P64636 P07024 P0AF24 | 25, 26 27, 28 29 30 31, 32 33 |
| NTP phosphatase | E. coli | 3.6.1.15 | AppA RavA | P07102 P31473 | 34, 35 36 |
| NTP phosphohydrolase | E. coli | 3.6.1.19 | YhdE MazG | P25536 P0AEY3 | 37 38 |

E. coli RNase III preferentially cleaves dsRNA as well as some single-stranded mRNA molecules. The presence of RNase III in cell lysate may limit the accumulation of high concentrations of synthetic RNA (e.g., dsRNA), because the synthetic RNA is readily cleaved. Neither RNase III nor the gene encoding RNase III, rnc, is essential for cell viability, thus, in some embodiments, rnc is deleted or mutated in engineered host cells. In other embodiments. RNase III is heat inactivated following depolymerization of endogenous RNA.

E. coli RNase I localizes to the periplasmic space in intact cells and catalyzes depolymerization of a wide range of RNA molecules, including rRNA, mRNA, and tRNA. Under physiological conditions the periplasmic localization of this enzyme means that the enzyme has little impact on RNA stability within the cell; however, mixing of the periplasm and cytoplasm in cell lysates permits RNase I access to cellular RNA. The presence of RNaseI in a cell lysate may reduce the yield of synthetic RNA through RNA degradation. Neither RNase I nor the gene encoding RNase I, rna, is essential for cell viability, thus, in some embodiments, rna is deleted or mutated in engineered host cells. In other embodiments, RNase I is heat inactivated following depolymerization of endogenous RNA.

E. coli RNase R and RNase T catalyze the depolymerization of dsRNA, rRNA, tRNA, and mRNA, as well as small unstructured RNA molecules. Neither the enzymes nor the genes encoding the enzymes, rnr and rnt, respectively, are essential for cell viability, thus, in some embodiments, rnr and/or rnt are deleted or mutated in engineered host cells (e.g., E. coli host cells). In other embodiments, RNase R and/or RNase T are heat inactivated following the depolymerization of endogenous RNA.

E. coli RNase E and PNPase are components of the degradasome, which is responsible for mRNA turnover in cells. RNase E is thought to function together with PNPase and RNase II to turn over cellular mRNA pools. Disruption of the gene encoding RNase E, rne, is lethal in E. coli. Thus, in some embodiments, RNase E is heat inactivated following depolymerization of endogenous RNA. Neither PNPase nor the gene encoding PNPase, pnp, is essential for cell viability, thus, in some embodiments, pnp is deleted or mutated in engineered host cells (e.g., *E. coli* host cells). In other embodiments, PNPase is heat inactivated following depolymerization of endogenous RNA.

*E. coli* RNase II depolymerizes both mRNA and tRNA in a 3'→5' direction. Neither RNase II nor the gene encoding RNase II, rnb, is essential for cell viability, thus, in some embodiments, rnb is deleted or mutated in engineered host cells. In other embodiments, RNase II is heat inactivated following depolymerization of endogenous RNA.

While neither pnp nor rnb is essential to host cell survival, disruption of both simultaneously may be lethal. Thus, in some embodiments, both PNPase and RNase II are heat inactivated.

Phosphorylation of Nucleoside Monophosphates to Nucleoside Triphosphates

Following conversion of endogenous RNA to its monomeric form, and following heat inactivation of endogenous nucleases and phosphatases, the resulting nucleoside monophosphates (NMPs) in a cell lysate are phosphorylated before they are polymerized to form a desired synthetic RNA, such as a double-stranded RNA or single-stranded RNA (e.g., mRNA or antisense RNA). This process is highly energy dependent, thus, this process requires an energy source. The phosphates are typically donated from a high-energy phosphate source, such as, for example, phosphoenolpyruvate, ATP, or polyphosphate.

In some embodiments, the energy source is ATP that is directly added to a cell lysate. In other embodiments, the energy source is provided using an ATP regeneration system. For example, polyphosphate and polyphosphate kinase may be used to produce ATP. Other examples included the use of acetyl-phosphate and acetate kinase to produce ATP; phospho-creatine and creatine kinase to produce ATP; and phosphoenolpyruvate and pyruvate kinase to produce ATP. Other ATP (or other energy) regeneration systems may be used. In some embodiments, at least one component of the energy source is added to a cell lysate or cell lysate mixture. A "component" of an energy source includes the substrate(s) and enzyme(s) required to produce energy (e.g., ATP). Non-limiting examples of these components include polyphosphate, polyphosphate kinase, acetyl-phosphate, acetate kinase, phospho-creatine, creatine kinase, phosphoenolpyruvate, and pyruvate kinase.

A kinase is an enzyme that catalyzes the transfer of phosphate groups from high-energy, phosphate-donating molecules, such as ATP, to specific substrates/molecules. This process is referred to as phosphorylation, where the substrate gains a phosphate group and the high-energy ATP molecule donates a phosphate group. This transesterification produces a phosphorylated substrate and ADP. The kinases of the present disclosure, in some embodiments, convert the NMPs to NDPs and NDPs to NTPs.

In some embodiments, a kinase is a nucleoside monophosphate kinase, which catalyzes the transfer of a high-energy phosphate from ATP to an NMP, resulting in ADP and NDP. Non-limiting examples of nucleoside monophosphate kinases are provided in Tables 4 and 5. As discussed below, thermostable variants of the enzymes listed in Tables 4 and 5 are encompassed by the present disclosure. In some embodiments, a cell lysate comprises one or more (or all) of the following four nucleoside monophosphate kinases: thermostable uridylate kinase, thermostable cytidylate kinase, thermostable guanylate kinase and thermostable adenylate kinase. In some embodiments, UMP kinase is obtained from *Pyrococcus furiosus* (e.g., SEQ ID NO:3 or a variant comprising an amino acid sequence that is at least 70% identical to the amino acid sequence identified by SEQ ID NO:3). In some embodiments, CMP kinase is obtained from *Thermus thermophilus* (e.g., SEQ ID NO:4 or a variant comprising an amino acid sequence that is at least 70% identical to the amino acid sequence identified by SEQ ID NO:4). In some embodiments, GMP kinase is obtained from *Thermotoga martima* (e.g., SEQ ID NO:5 or a variant comprising an amino acid sequence that is at least 70% identical to the amino acid sequence identified by SEQ ID NO:5). In some embodiments. AMP kinase is obtained from *Thermus thermophilus* (e.g., SEQ ID NO:6 or a variant comprising an amino acid sequence that is at least 70% identical to the amino acid sequence identified by SEQ ID NO:6).

Thus, in some embodiments, a NMP kinase has an amino acid sequence identified by the amino acid sequence of any one of SEQ ID NO: 3-6. In some embodiments, the NMP kinase has an amino acid sequence that is at least 70% identical to the amino acid sequence of any one of SEQ ID NO: 3-6. For example, the NMP kinase may have an amino acid sequence that is at least 75%, at least 80%, at least 85%, at least 90%, at least 95%, at least 96%, at least 97%, at least 98%, or at least 99% identical to the amino acid sequence identified by any one of SEQ ID NO: 3-6.

It should be understood that the present disclosure encompasses the use of any one or more of the enzymes described herein as well as variants of the enzymes (e.g., "PPK2 variants"). Variant enzymes may share a certain degree of sequence identity with the reference enzyme. The term "identity" refers to a relationship between the sequences of two or more polypeptides or polynucleotides, as determined by comparing the sequences. Identity measures the percent of identical matches between the smaller of two or more sequences with gap alignments (if any) addressed by a particular mathematical model or computer program (e.g., "algorithms"). Identity of related molecules can be readily calculated by known methods. "Percent (%) identity" as it applies to amino acid or nucleic acid sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Identity depends on a calculation of percent identity but may differ in value due to gaps and penalties introduced in the calculation. Variants of a particular sequence may have at least 70%, 75%, 80%, 85%, 90%, 91%, 92%, 93%, 94%, 95%, 96%, 97%, 98%, 99% but less than 100% sequence identity to that particular reference sequence, as determined by sequence alignment programs and parameters described herein and known to those skilled in the art.

The comparison of sequences and determination of percent identity between two sequences can be accomplished using a mathematical algorithm. Techniques for determining identity are codified in publicly available computer programs. Exemplary computer software to determine homology between two sequences include, but are not limited to, GCG program package (Devereux, J. et al. Nucleic Acids Research, 12(1): 387, 1984), the BLAST suite (Altschul, S. F. et al. Nucleic Acids Res. 25: 3389, 1997), and FASTA (Altschul, S. F. et al. J. Molec. Biol. 215: 403, 1990). Other techniques include: the Smith-Waterman algorithm (Smith, T. F. et al. J. Mol. Biol. 147: 195, 1981; the Needleman-Wunsch algorithm (Needleman, S. B. et al. J. Mol. Biol. 48: 443, 1970; and the Fast Optimal Global Sequence Alignment Algorithm (FOGSAA) (Chakraborty, A. et al. Sci Rep. 3: 1746, 2013).

TABLE 4

Examples of Nucleoside Monophosphate Kinases

| Enz. Name | Host Organism | EC # | Reaction | Uniprot | Ref. |
|---|---|---|---|---|---|
| PyrH | E. coli | 2.7.4.22 | UMP + ATP → UDP + ADP | P0A7E9 | 39, 40 |
| | T. thermophilus | | | P43891 | 41 |
| | P. furiosus | | | Q8U122 | 42, 43 |
| Cmk | E. coli | 2.7.4.25 | CMP + ATP → CDP + ADP | P0A6I0 | 44, 45 |
| | T. thermophilus | | | Q5SL35 | 41 |
| | P. furiosus | | | Q8U2L4 | 46 |
| Gmk | E. coli | 2.7.4.8 | GMP + ATP → GDP + ADP | P60546 | 47, 48 |
| | T. thermophilus | | | Q5SI18 | 41 |
| | T. maritima | | | Q9X215 | 49 |
| Adk | E. coli | 2.7.4.3 | AMP + ATP → 2 ADP | P69441 | 50, 51 |
| | T. thermophilus | | | Q72I25 | 52, 53 |
| | P. furiosus | | | Q8U207 | 46 |

In some embodiments, a kinase is a nucleoside diphosphate kinase, which transfers a phosphoryl group to NDP, resulting in NTP. The donor of the phosphoryl group may be, without limitation, ATP, polyphosphate polymer, or phosphoenolpyruvate. Non-limiting examples of kinases that convert NDP to NTP include nucleoside diphosphate kinase, polyphosphate kinase, and pyruvate kinase. As discussed below, thermostable variants of the foregoing enzymes are encompassed by the present disclosure. In some embodiments, the NDP kinase(s) is/are obtained from *Aquifex aeolicus* (e.g., SEQ ID NO: 9 or a variant comprising an amino acid sequence that is at least 70% identical to the amino acid sequence identified by SEQ ID NO:9). In some embodiments, the NDP kinase has an amino acid sequence that is at least 70% identical to the amino acid sequence identified by SEQ ID NO: 9. For example, the NDP kinase may have an amino acid sequence that is at least 75%, at least 80%, at least 85%, at least 90%, at least 95%, at least 96%, at least 97%, at least 98%, or at least 99% identical to the amino acid sequence identified by SEQ ID NO: 9.

Figure 2A:
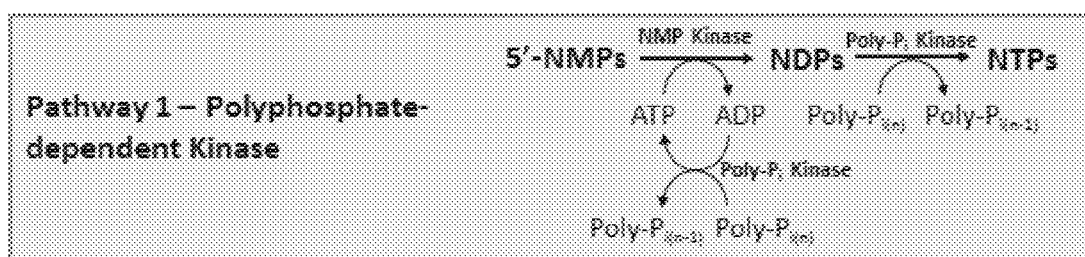
FIG. 2A shows a schematic of a polyphosphate-dependent kinase pathway for energy generation.
Figure 2B:
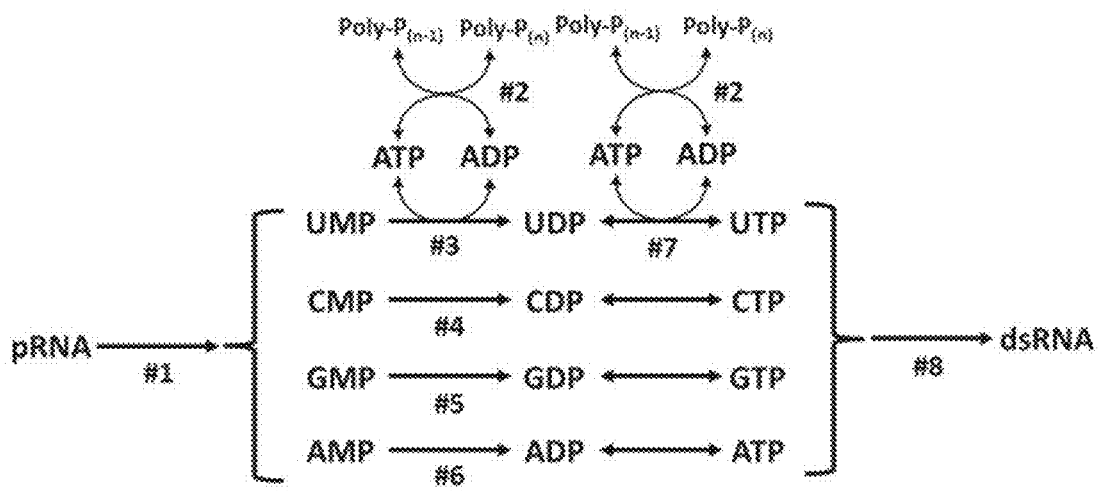
FIG. 2B shows a schematic of additional exemplary energy conversion pathways for use in the methods and systems of the present disclosure. A UMP kinase (e.g., obtained from *Pyrococcus furiosus*) and a polyphosphate kinase (e.g., obtained from *Thermosynechococcus elongatus, Caldilinea aerophila, Deinococcus geothermalis, Meiothermus ruber, Meiothermus silvanus, Deinococcus geothermalis, Anaerolinea thermophila, Chlorobaculum tepidum, Oceanithermus profundus, Roseiflexus castenholzii, Roseiflexus sp., or Truepera radiovctrix*) may be used to convert UMP to UDP, and NDP kinases (e.g., encoded by an *Aquifex aeolicus* ndk gene) and a polyphosphate kinase may be used to convert UDP to UTP. A CMP kinase (e.g., obtained from *Thermus thermophilus*) and a polyphosphate kinase may be used to convert CMP to CDP, and NDP kinases and a polyphosphate kinase may be used to convert CDP to CTP. A GMP kinase (e.g., obtained from *Thermotoga maritima*) and a polyphosphate kinase may be used to convert GMP to GDP, and NDP kinases and a polyphosphate kinase may be used to convert GDP to GTP. An AMP kinase (e.g., obtained from *Thermus thermophilus*) and a polyphosphate kinase may be used to convert AMP to ADP, and NDP kinases (e.g., encoded by an *Aquifex aeolicus* ndk gene) and a polyphosphate kinase may be used to convert ADP to ATP. Alternatively, a Class III PPK2 enzyme (see, e.g., Table 6) may be used to convert AMP to ATP.

Phosphorylation of NMPs to NTPs occurs, in some embodiments, through the polyphosphate-dependent kinase pathway (FIGS. 2A and 2B), where high-energy phosphate is transferred from polyphosphate to ADP via a polyphosphate kinase (PPK). In some embodiments, the polyphosphate kinase belongs to the polyphosphate kinase 1 (PPK1) family, which transfers high-energy phosphate from polyphosphate to ADP to form ATP. This ATP is subsequently used by NMP kinases (e.g., AMP kinase, UMP kinase, GMP kinase, and CMP kinase) to convert NMPs to their cognate ribonucleotide diphosphates (NDPs). Furthermore, ATP is subsequently used by nucleotide diphosphate kinase to convert NDPs to NTPs. See, e.g., Tables 5 and 6 for exemplary enzymes.

In some embodiments, the polyphosphate kinase belongs to the polyphosphate kinase 2 (PPK2) family. In some embodiments, the polyphosphate kinase belongs to a Class I PPK2 family, which transfers high-energy phosphate from polyphosphate to NDPs to form NTPs. ATP produced by the system is used as a high-energy phosphate donor to convert NMPs to NDPs. In some embodiments, the polyphosphate kinase belongs to a Class III PPK2 family, which transfers high-energy phosphate from polyphosphate to NMPs and NDPs to form NTPs. In some embodiments, Class III PPK2 is used alone to produce NTPs from NMPs. In other embodiments, Class III PPK2 is used in combination with other kinases. Class III PPK2 produces ATP from ADP, AMP, and polyphosphate, which is subsequently used by NMP and NDP kinases to convert NMPs to NTPs.

Non-limiting examples of PPK2 enzymes for use as provided herein are listed in Table 6 (SEQ ID NO: 8-18). Thus, in some embodiments, the PPK2 enzymes are thermostable. For example, the PPK2 enzymes may be thermostable Class III PPK2 enzymes, which favor ATP synthesis over polyphosphate polymerization, and convert both ADP and AMP to ATP. In some embodiments, the PPK2 enzymes are used to convert a polyphosphate, such as hexametaphosphate to ATP, at rates ranging, for example, from 10 to 800 mM per hour (e.g., 10, 15, 20, 25, 50, 75, 100, 150, 200, 250, 300, 350, 400, 450, 500, 550, 600, 650, 700, 750, or 800 mM per hour).

In some embodiments, the RNA biosynthesis methods of the present disclosure utilize a PPK2 enzyme that comprises an amino acid sequence identical to the amino acid sequence identified by any one of SEQ ID NO: 8-18. In some embodiments, the PPK2 enzyme comprises an amino acid sequence that is at least 70% identical to the amino acid sequence identified by any one of SEQ ID NO: 8-18. For example, the PPK2 enzyme may comprise an amino acid sequence that is at least 75%, at least 80%, at least 85%, at least 90%, at least 95%, at least 96%, at least 97%, at least 98%, or at least 99% identical to the amino acid sequence identified by any one of SEQ ID NO: 8-18.

The present disclosure also encompasses fusion enzymes. Fusion enzymes may exhibit multiple activities, each corresponding to the activity of a different enzyme. For example, rather than using an independent nucleoside monophosphate kinase and an independent nucleoside diphosphate kinase, a fusion enzyme (or any other enzyme) having both nucleoside monophosphate kinase activity and nucleoside diphosphate kinase activity may be used.

TABLE 5

Examples of Pathway Enzymes

| Enz. # | Enzyme Name | EC # | Organism | Uniprot # | Sequence Identification Number |
|---|---|---|---|---|---|
| 1 | RNase R | 3.1.13.— | Escherichia coli | P21499 | SEQ ID NO: 1 |
| 2 | PPK1 | 2.7.4.1 | Thermosynechococcus elongatus | Q8DMA8 | SEQ ID NO: 2 |
| 3 | UMP Kinase | 2.7.4.22 | Pyrococcus furiosus | Q8U122 | SEQ ID NO: 3 |
| 4 | CMP Kinase | 2.7.4.25 | Thermus thermophilus | Q5SL35 | SEQ ID NO: 4 |
| 5 | GMP Kinase | 2.7.4.8 | Thermotoga maritima | Q9X215 | SEQ ID NO: 5 |
| 6 | AMP Kinase | 2.7.4.3 | Thermus thermophilus | Q72I25 | SEQ ID NO: 6 |
| 7 | NDP Kinase | 2.7.4.6 | Aquifex aeolicus | O67528 | SEQ ID NO: 7 |
| 8 | RNA Polymerase | | | | |

TABLE 6

Examples of PPK2 Enzymes

| Organism | Accession # | Sequence Identification Number |
|---|---|---|
| Meiothermus ruber DSM 1279 | ADD29239.1 | SEQ ID NO: 8 |
| Meiothermus silvanus DSM 9946 | WP_013159015.1 | SEQ ID NO: 9 |

TABLE 6-continued

Examples of PPK2 Enzymes

| Organism | Accession # | Sequence Identification Number |
|---|---|---|
| Deinococcus geothermalis DSM 11300 | WP_011531362.1 | SEQ ID NO: 10 |
| Thermosynechococcus elongatus BP-1 | NP_682498.1 | SEQ ID NO: 11 |
| Anaerolinea thermophila UNI-1 | WP_013558940 | SEQ ID NO: 12 |
| Caldilinea aerophila DSM 14535 | WP_014433181 | SEQ ID NO: 13 |
| Chlorobaculum tepidum TLS | NP_661973.1 | SEQ ID NO: 14 |
| Oceanithermus profundus DSM 14977 | WP_013458618 | SEQ ID NO: 15 |
| Roseiflexus castenholzii DSM 13941 | WP_012120763 | SEQ ID NO: 16 |
| Roseiflexus sp. RS-1 | WP_011956376 | SEQ ID NO: 17 |
| Truepera radiovictrix DSM 17093 | WP_013178933 | SEQ ID NO: 18 |

Polymerization of Nucleoside Triphosphates to Ribonucleic Acid

Figure 3A:
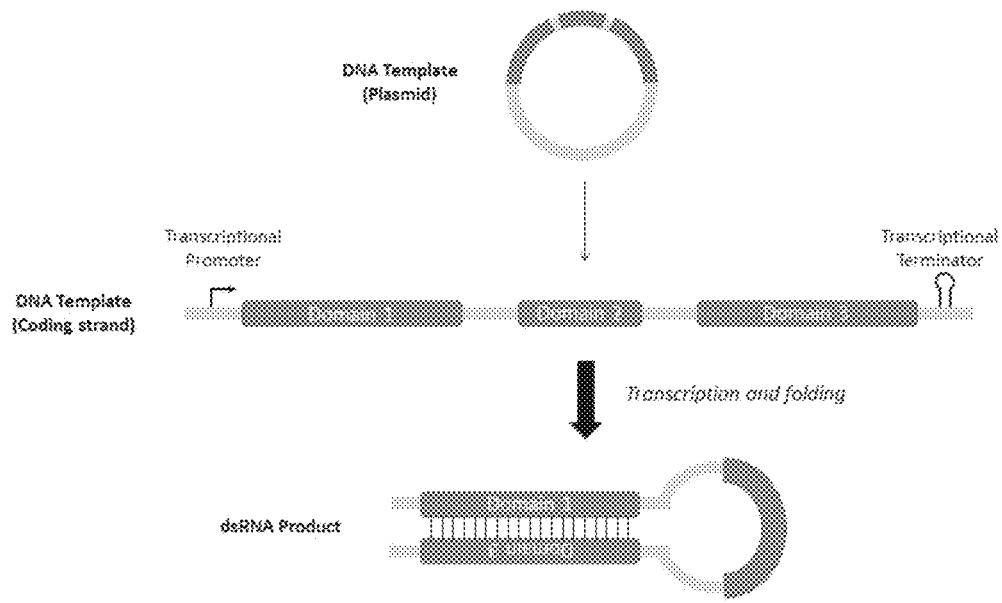
FIG. 3A shows a schematic of an example of a DNA template used for the biosynthesis of double-stranded RNA. The DNA template, encoded as part of a plasmid, contains a single coding region including of a promoter operably linked to the coding region of interest and one or more terminators. Following transcription, the RNA folds into a hairpin structure through intramolecular nucleotide base pairing. The DNA template, either alone or encoded as part of a plasmid, contains two complementary domains (1 and 3), separated by domain 2.

The final step in the biosynthesis of a RNA of interest is the polymerization of NTPs to the RNA (e.g., dsRNA or ssRNA) end product using, for example, a DNA-dependent RNA polymerase. In this step of the process, a DNA designed to encode the RNA of interest serves as the template for the synthesis of the RNA of interest. The DNA template may be engineered, in some instances, to have a transcriptional promoter that selectively drives transcription of the RNA of interest. An example DNA template is shown in FIG. 3A. The DNA template encodes three RNA domains: a sense domain (domain 1), a flexible hinge domain (domain 2) and a domain complementary to the sense domain (antisense domain 3). Following transcription of the DNA template, the antisense domain binds (hybridizes) to the sense domain to form a double-stranded RNA hairpin stem domain and an adjacent hairpin loop domain. Other examples of a DNA template are shown in FIGS. 3B-3E. The DNA template in FIG. 3B contains converging promoter sequences on complementary strands. RNA sequences transcribed from each template strand anneal after transcription. The DNA template in FIG. 3C, encoded as part of a plasmid, contains converging promoter sequences on complementary strands, as well as one or more terminator sequences to minimize read-through transcription. The DNA template in FIG. 3D, encoded as part of a plasmid, contains independent promoter-terminator cassettes driving transcription of complementary sequences, which anneal after transcription. The DNA template in FIG. 3E encodes a single RNA domain. Use of both DNA-dependent RNA polymerase and RNA-dependent RNA polymerase produces a double-stranded RNA end product.

Polymerization of RNA requires NTPs, a DNA template comprising a transcriptional promoter, and a polymerase (RNA polymerase) specific to the transcriptional promoter. Typically, a polymerase for use as provided herein is a single subunit polymerase, is highly selective for its cognate transcriptional promoters, has high fidelity, and is highly efficient. Examples of polymerases include, without limitation, T7 RNA polymerase, T3 RNA polymerase, and SP6 RNA polymerase. Bacteriophage T7 RNA polymerase is a DNA-dependent RNA polymerase that is highly specific for the T7 phage promoters. The 99 KD enzyme catalyzes in vitro RNA synthesis from a cloned DNA sequence under control of the T7 promoter. Bacteriophage T3 RNA polymerase is a DNA-dependent RNA polymerase that is highly specific for the T3 phage promoters. The 99 KD enzyme catalyzes in vitro RNA synthesis from a cloned DNA sequence under the T3 promoter. Bacteriophage SP6 RNA polymerase is a DNA-dependent RNA polymerase that is highly specific for the SP6 phage promoter. The 98.5 KD polymerase catalyzes in vitro RNA synthesis from a cloned DNA template under the SP6 promoter. Each of T7, T3, and SP6 polymerase are optimally active at 37-40° C. In some embodiments, thermostable variants of T7, T3, and SP6 polymerase are used. Thermostable variant polymerases are typically optimally active at temperatures above 40° C. (or about 50-60° C.).

"Conditions that result in production of nucleoside triphosphates and polymerization of the nucleoside triphosphates," also referred to as "conditions for the biosynthesis of RNA," may be determined by one of ordinary skill in the art, taking into consideration, for example, optimal conditions for polymerase activity, including pH, temperature, length of time, and salt concentration of the cell lysate as well as any exogenous cofactors.

The pH of a cell lysate during the biosynthesis of RNA may have a value of 3.0 to 8.0. In some embodiments, the pH value of a cell lysate is 3.0-8.0, 4.0-8.0, 5.0-8.0, 6.0-8.0, 7.0-8.0, 3.0-7.0, 4.0-7.0, 5.0-7.0, 6.0-7.0, 3.0-6.0, 4.0-6.0, 5.0-6.0, 3.0-5.0, 3.0-4.0, or 4.0-5.0. In some embodiments, the pH value of a cell lysate is 3.0, 3.5, 4.0, 4.5, 5.0, 5.5, 6.0, 6.5, 7.0, 7.5, or 8.0. In some embodiments, the pH value of a cell lysate during biosynthesis of RNA is 7.0.

The temperature of a cell lysate during biosynthesis of RNA may be 15° C. to 70° C. In some embodiments, the temperature of a cell lysate during biosynthesis of RNA is 15-60° C., 15-50° C., 15-40° C., 15-30° C., 25-70° C. 25-60° C., 25-50° C., 25-40° C., 30-70° C., 30-60° C., 30-50° C., 40-70° C. 40-60° C., 40-50° C., 50-70° C., or 50-60° C. In some embodiments, the temperature of a cell lysate during biosynthesis of RNA is 15° C., 25° C., 32° C., 37° C., 42° C., 45° C., 55° C. 56° C., 57° C., 58° C., 59° C., 60° C., 61° C., 62° C., 63° C., 64° C., 65° C., 66° C., 67° C., 68° C., 69° C., or 70° C. In some embodiments, the temperature of a cell lysate during biosynthesis of RNA is 50° C.

A cell lysate during biosynthesis of RNA may be incubated for 15 minutes (min) to 72 hours (hrs). In some embodiments, a cell lysate during biosynthesis of RNA is incubated for 30 min-48 hrs. For example, a cell lysate during biosynthesis of RNA may be incubated for 30 min, 45 min, 1 hr, 2 hrs, 3 hrs, 4 hrs, 5 hrs, 6 hrs, 7 hrs, 8 hrs, 9 hrs, 10 hrs, 11 hrs, 12 hrs, 18 hrs, 24 hrs, 30 hrs, 36 hrs, 42 hours, or 48 hours. In some embodiments, a cell lysate during biosynthesis of RNA is incubated for 3 hours. In some embodiments, a cell lysate during biosynthesis of RNA is incubated for 24 hours at a temperature of 37° C.

In some embodiments, a cell lysate during biosynthesis of RNA is incubated at a pH of 7.0 for 2-4 hours at a temperature of 50° C.

Some polymerase activities may require the presence of metal ions. Thus, in some embodiments, metal ions are added to a cell lysate. Non-limiting examples of metal ions include $Mg^{2+}$, $Li^+$, $Na^+$, $K^+$, $Ni^{2+}$, $Ca^{2+}$, $Cu^{2+}$, and $Mn^{2+}$. Other metal ions may be used. In some embodiments, more than one metal ion may be used. The concentration of a metal ion in a cell lysate may be 0.1 mM to 100 mM, or 10 mM to 50 mM. In some embodiments, the concentration of a metal ion in a cell lysate is 0.1, 0.2, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 20.0, 25.0, 30.0, 35.0, 40.0, 45.0, 50.0, 60.0, 70.0, 80.0, 90.0, or 100.0 mM.

In some embodiments, salt is added to a cell lysate, for example, to prevent enzyme aggregation. For example, sodium chloride, potassium chloride, sodium acetate, potassium acetate, or a combination thereof, may be added to a cell lysate. The concentration of salt in a cell lysate during a RNA depolymerization reaction may be 5 mM to 1 M. In some embodiments, the concentration of salt in a cell lysate during a RNA depolymerization reaction 5 mM, 10 mM, 15 mM, 20 mM, 25 mM, 50 mM, 100 mM, 150 mM, 200 mM, 250 mM, 500 mM, 750 mM, or 1 M.

Thermostable Enzymes

One advantage of the cell-free RNA-biosynthesis methods of the present disclosure is that all of the enzymes needed to convert endogenous RNA to synthetic double-stranded RNA, for example, may be (but need not be) expressed in a single engineered cell. For example, a clonal population of the engineered cell is cultured to a desired cell density, the cells are lysed, incubated under conditions that result in depolymerization of endogenous RNA to its monomer form (e.g., at a temperature of 30-37° C.), subjected to temperatures sufficient to inactivate endogenous nucleases and phosphatases (e.g., 40-90° C.), and incubated under conditions that result in the polymerization of RNA (e.g., dsRNA or ssRNA) (e.g., 30-50° C.). In order to proceed to end product synthetic RNA, the enzymes required for conversion of NMPs to NDPs (e.g., nucleoside monophosphate kinases and/or polyphosphate kinases), from NDPs to NTPs (e.g., nucleoside diphosphate kinases and/or polyphosphate kinase), and from NTPs to RNA (e.g., polymerase) should be thermostable to avoid denaturation during heat inactivation of the endogenous nuclease (and/or exogenous nucleases) and phosphatases. Thermostability refers to the quality of enzymes to resist denaturation at relatively high temperature. For example, if an enzyme is denatured (inactivated) at a temperature of 42° C., an enzyme having similar activity (e.g., kinase activity) is considered "thermostable" if it does not denature at 42° C.

An enzyme (e.g., kinase or polymerase) is considered thermostable if the enzyme (a) retains activity after temporary exposure to high temperatures that denature other native enzymes or (b) functions at a high rate after temporary exposure to a medium to high temperature where native enzymes function at low rates.

In some embodiments, a thermostable enzyme retains greater than 50% activity following temporary exposure to relatively high temperature (e.g., higher than 41° C. for kinases obtained from E. coli, higher than 37° C. for many RNA polymerases) that would otherwise denature a similar (non-thermostable) native enzyme. In some embodiments, a thermostable enzyme retains 50-100% activity following temporary exposure to relatively high temperature that would otherwise denature a similar (non-thermostable) native enzyme. For example, a thermostable enzyme may retain 50-90%, 50-85%, 50-80%, 50-75%, 50-70%, 50-65%, 50-60%, or 50-55% activity following temporary exposure to relatively high temperature that would otherwise denature a similar (non-thermostable) native enzyme. In some embodiments, a thermostable enzyme retains 25%, 30%, 35%, 40%, 45%, 50%, 55%, 60%, 65%, 70%, 75%, 80%, 85%, 90%, 95%, 98%, 99%, or 100% activity following temporary exposure to relatively high temperature that would otherwise denature a similar (non-thermostable) native enzyme.

In some embodiments, the activity of a thermostable enzyme after temporary exposure to medium to high temperature (e.g., 42-80° C.) is greater than (e.g., 25%, 30%, 35%, 40%, 45%, 50%, 55%, 60%, 65%, 70%, 75%, 80%, 85%, 90%, 95%, 98%, 99%, or 100% greater than) the activity of a similar (non-thermostable) native enzyme.

The activity of a thermostable kinase, for example, may be measured by the amount of NMP or NDP the kinase is able to phosphorylate. Thus, in some embodiments, a thermostable kinase, at relatively high temperature (e.g., 42° C.) converts greater than 50% of NMP to NDP, or greater than 50% of NDP to NTP, in the same amount of time required to complete a similar conversion at 37° C. In some embodiments, a thermostable kinase, at relatively high temperature (e.g., 42° C.) converts greater than 60% of NMP to NDP, or greater than 60% of NDP to NTP, in the same amount of time required to complete a similar conversion at 37° C. In some embodiments, a thermostable kinase, at relatively high temperature (e.g., 42° C.) converts greater than 70% of NMP to NDP, or greater than 70% of NDP to NTP, in the same amount of time required to complete a similar conversion at 37° C. In some embodiments, a thermostable kinase, at relatively high temperature (e.g., 42° C.) converts greater than 80% of NMP to NDP, or greater than 80% of NDP to NTP, in the same amount of time required to complete a similar conversion at 37° C. In some embodiments, a thermostable kinase, at relatively high temperature (e.g., 42° C.) converts greater than 90% of NMP to NDP, or greater than 90% of NDP to NTP, in the same amount of time required to complete a similar conversion at 37° C.

The activity of a thermostable polymerase, for example, is assessed based on fidelity and polymerization kinetics (e.g., rate of polymerization). Thus, one unit of a thermostable T7 polymerase, for example, may incorporate 10 nmoles of NTP into acid insoluble material in 30 minutes at temperatures above 37° C. (e.g., at 50° C.).

Thermostable enzymes (e.g., kinases or polymerases) may remain active (able to catalyze a reaction) at a temperature of 42° C. to 80° C., or higher. In some embodiments, thermostable enzymes remain active at a temperature of 42-80° C., 42-70° C., 42-60° C., 42-50° C., 50-80° C., 50-70° C., 50-60° C., 60-80° C., 60-70° C., or 70-80° C. For example, thermostable enzymes may remain active at a temperature of 42° C., 43° C. 44° C., 45° C., 46° C., 47° C., 48° C., 49° C., 50° C., 51° C., 52° C., 53° C., 54° C., 55° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C. 79° C., or 80° C. Thermostable enzymes may remain active at relatively high temperatures for 15 minutes to 48 hours, or longer. For example, thermostable enzymes may remain active at relatively high temperatures for 1, 2, 3, 4, 5, 6, 7, 8, 9, 10, 11, 12, 13, 14, 15, 16, 17, 18, 19, 20, 24, 36, 42, or 48 hours.

Non-limiting examples of thermostable NMP kinases are listed in Tables 5 and 7. Other thermostable kinases include thermostable nucleoside diphosphate kinases, thermostable pyruvate kinases, and thermostable polyphosphate kinases (see, e.g., Table 6). Other thermostable kinases are encompassed by the present disclosure.

TABLE 7

Examples of Thermostable Nucleoside Monophosphate Kinases.

| Enzyme Name | Host Organism | EC # | Reaction | Uniprot | Ref. |
| --- | --- | --- | --- | --- | --- |
| Uridylate kinase | T. thermophilus, P. furiosus | 2.7.4.22 | UMP → UDP + ADP | P43891 | 41 |
| | | | | Q8U122 | 42, 43 |
| Cytidylate kinase | T. thermophilus, P. furiosus | 2.7.4.25 | CMP → CDP + ADP | Q5SL35 | 41 |
| | | | | Q8U2L4 | 46 |
| Guanylate kinase | T. thermophilus, T. maritima | 2.7.4.8 | GMP → GDP + ADP | Q5SI18 | 41 |
| | | | | Q9X215 | 49 |
| Adenylate kinase | T. thermophilus, P. furiosus | 2.7.4.3 | AMP → 2ADP | Q72I25 | 52, 53 |
| | | | | Q8U207 | 46 |

Non-limiting examples of RNA polymerases are listed in Table 8. Other RNA polymerases, including thermostable RNA polymerases, are encompassed by the present disclosure.

TABLE 8

Examples of RNA Polymerases

| Enzyme Name | Host Organism | Function | Uniprot | Ref |
| --- | --- | --- | --- | --- |
| T7 RNA Polymerase | T7 Phage | DNA-dependent RNA polymerase | P00573 | 54, 55 |
| Φ6 RdRP | Phage Φ6 | RNA-dependent RNA polymerase | P11124 | 56 |
| T3 RNA polymerase | T3 Phage | DNA-dependent RNA polymerase | P07659 | 57 |
| SP6 Polymerase | SP6 Phage | DNA-Dependent RNA polymerase | P06221 | 58 |

Thermostable RNA polymerases may be prepared by modifying wild-type enzymes. Such modifications (e.g., mutations) are known. For example, variant thermostable T7 RNA polymerases may include one or more of the following point mutations: V426L, A702V, V795I, S430P, F849I, S633I, F880Y, C510R, and S767G (EP2377928 and EP1261696A1, each of which is incorporated herein by reference). In some embodiments, a variant thermostable T7 RNA polymerase includes V426L, A702V, and V795I mutations. In some embodiments, a variant thermostable T7 RNA polymerase includes S430P, F849I, S633I, and F880Y mutations. In some embodiments, a variant thermostable T7 RNA polymerase includes F880Y, S430P, F849I, S633I, C510R, and S767G mutations. In some embodiments, a variant thermostable T7 RNA polymerase includes Y639V, H784G, E593G, and V685A mutations. In some embodiments, a variant thermostable T7 RNA polymerase includes S430P, N433T, S633P, F849I, and F880Y mutations. Other variant and recombinant thermostable polymerases are encompassed by the present disclosure.

In some embodiments, a thermostable T7 polymerase is used to produce a RNA of interest. For example, a thermostable T7 polymerase (e.g., incubated at a temperature of 40-60° C.) having a concentration of 1-2% total protein may be used to synthesize RNA of interest at a rate of greater than 2 g/L/hr (or, e.g., 2 g/L/hr-10 g/L/hr). As another example, a thermostable T7 polymerase (e.g., incubated at a temperature of 40-60° C.) having a concentration of 3-5% total protein may be used to synthesize RNA of interest at a rate of greater than 10 g/L/hr (or, e.g., 10 g/L/hr-20 g/L/hr).

It should be understood that while many embodiments of the present disclosure describe the use of thermostable polymerases/enzymes, other enzymes/polymerases may be used. In some embodiments, polymerase may be exogenously added to heat-inactivated cell lysates, for example, to compensate for any reduction or loss of activity of the thermostable enzyme(s).

RNA of Interest

Methods of the present disclosure are used to biosynthesize a RNA of interest. The RNA may be single-stranded or double-stranded. In some embodiments, the RNA is a double-stranded RNA interference molecule. For example, a RNA of interest may be an siRNA or a hairpin RNA interference molecule. As discussed above, a RNA of interest is encoded by a DNA template, examples of which are shown in FIGS. 3A-3E. The RNA produced using the template of FIG. 3A includes a sense domain (domain 1), a flexible hinge domain (domain 2) and a domain complementary to the sense domain (antisense domain 3). Following transcription of the DNA template, the antisense domain binds (hybridizes) to the sense domain to form a double-stranded RNA hairpin stem domain and an adjacent hairpin loop (hinge) domain.

A double-stranded hairpin stem domain is formed by the binding of two complementary nucleic acid domains (e.g., discrete nucleotide sequences) to each other. Nucleic acid domains are "complementary" if they bind (base pair via Watson-Crick interactions, hybridize) to each other to form a double-stranded nucleic acid. The complementary domains of a DNA template encoding a RNA of interest may vary, depending, for example, on the desired end product. Complementary domains may have a length of, for example, 4 to 1000 nucleotides, or longer. For example, complementary domains may have a length of 4 to 10, 4 to 20, 4 to 30, 4 to 50, 4 to 60, 4 to 70, 4 to 80, 4 to 90, 4 to 100, 4 to 200, 4 to 300, 4 to 400, or 4 to 500, or 4 to 1000 nucleotides. In some embodiments complementary domains have a length of 15, 16, 17, 18, 19, 20, 21, 22, 23, 24, or 25 nucleotides. In some embodiments, complementary domains have a length of 4, 5, 6, 7, 8, 9, 10, 15, 20, 25, 30, 35, 40, 45, 50, 55, 60, 65, 70, 75, 80, 85, 90, 95 or 100 nucleotides.

A hairpin loop domain is also formed by binding of two complementary nucleic acid domains. A hairpin loop domain is the intervening sequence between two complementary domains. Typically, a hairpin loop domain is non-specific, meaning that it is not designed to bind intramolecularly or to another nucleic acid. A hairpin loop domain forms a loop-like structure upon binding of the complementary domains to form a double-stranded hairpin stem domain. In some embodiments, a hairpin loop domain has a length of 4 to 500 nucleotides, or more. For example, a hairpin loop domain may have a length of 4 to 10, 4 to 20, 4 to 30, 4 to 50, 4 to 60, 4 to 70, 4 to 80, 4 to 90, 4 to 100, 4 to 200, 4 to 300, 4 to 400, or 4 to 500 nucleotides. In some embodiments, a hairpin loop domain has a length of 4, 5, 6, 7, 8, 9, 10, 15, 20, 25, 30, 35, 40, 45, 50, 55, 60, 65, 70, 75, 80, 85, 90, 95 or 100 nucleotides.

Figure 3B:
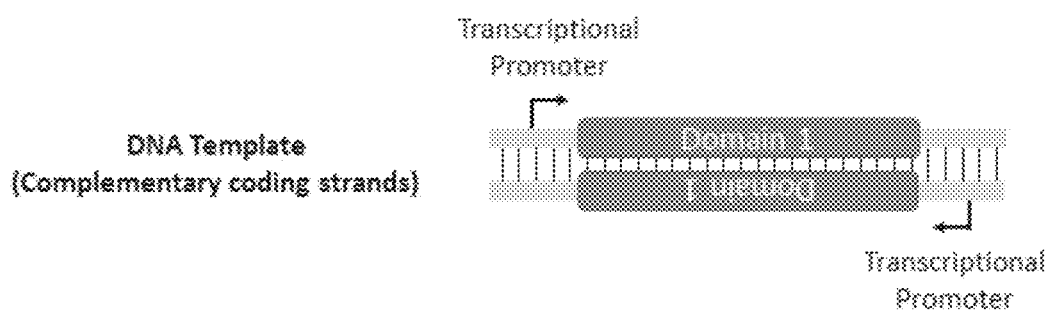
FIG. 3B shows a schematic of another example of a DNA template used for biosynthesis of double-stranded RNA. The DNA template contains converging promoter sequences on complementary strands. RNA sequences transcribed from each template strand anneal after transcription.
Figure 3C:
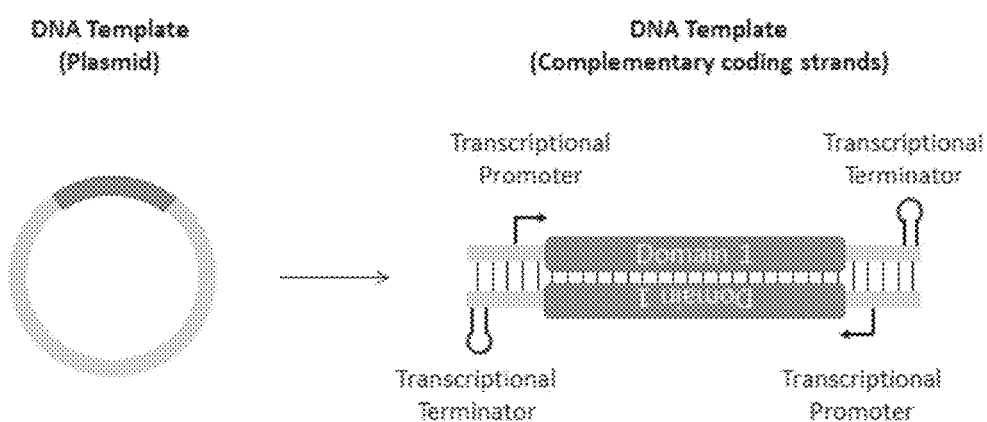
FIG. 3C shows a schematic of another example of a DNA template used for biosynthesis of double-stranded RNA. The DNA template, encoded as part of a plasmid, contains converging promoter sequences operably linked to coding regions of interest on complementary strands, as well as one or more terminator sequences to prevent read-through transcription.
Figure 3D:
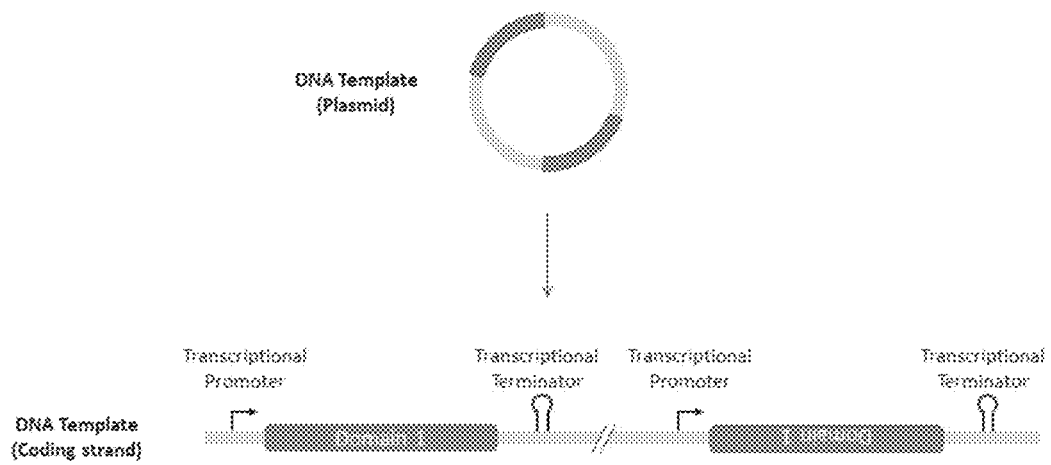
FIG. 3D shows a schematic of another example of a DNA template used for biosynthesis of double-stranded RNA. The DNA template, encoded as part of a plasmid, contains independent cassettes, each including of a promoter operably linked to the coding region of interest and one or more terminators, driving transcription of complementary sequences, which anneal after transcription.
Figure 3E:
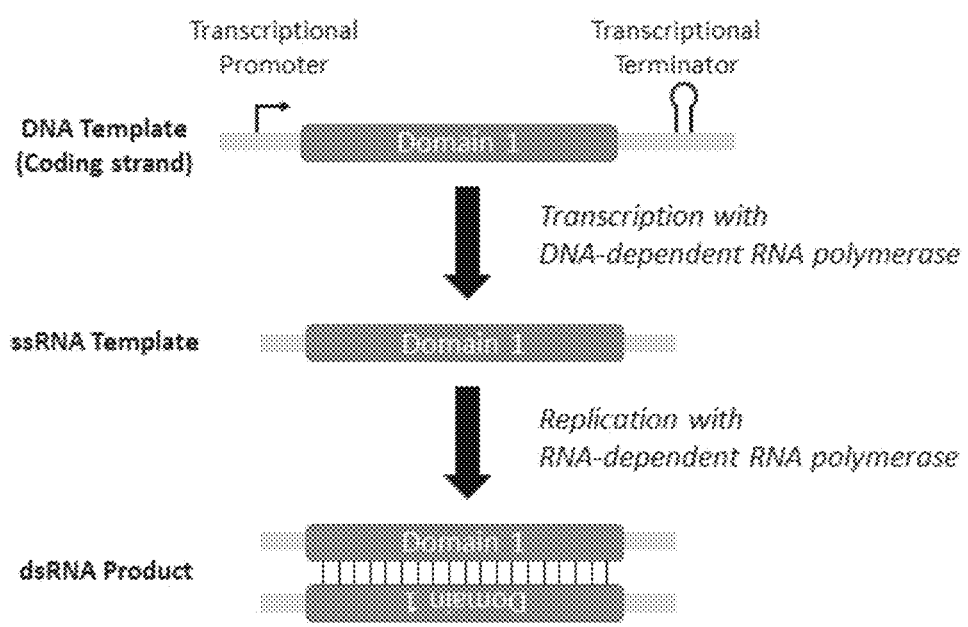
FIG. 3E shows a schematic of another example of a DNA template used for biosynthesis of double-stranded RNA. DNA-dependent RNA polymerase is used to produce ssRNA template, and the RNA-dependent RNA polymerase is used to produce double-stranded RNA.

A "double-stranded RNA" of the present disclosure encompasses wholly double-stranded molecules, which do not contain a single-stranded region (e.g., a loop or overhang), as well as partially double-stranded molecules, which contain a double-stranded region and a single-stranded region (e.g., a loop or overhang). The dsRNA product depicted at the bottom of FIG. 3A is considered a partially double-stranded molecule, while the dsRNA product depicted at the bottom of FIG. 3B is considered a wholly double-stranded molecule.

Examples of "single-stranded RNA" of interest include messenger RNA (mRNA) and antisense RNA. Thus, provided herein are methods of synthesizing mRNA and other single-stranded RNA molecules.

These methods may comprise (a) lysing cultured engineered cells that comprise RNA, an enzyme that depolymerizes RNA, thermostable kinases, a thermostable RNA polymerase, thereby producing a cell lysate, (b) incubating the cell lysate produced in step (a) under conditions that result in depolymerization of RNA, thereby producing a cell lysate that comprises nucleoside monophosphates, (c) heating the cell lysate produced in step (b) to a temperature that inactivates endogenous nucleases and phosphatases without inactivating the thermostable kinases and thermostable RNA polymerase, thereby producing a cell lysate that comprises heat-inactivated nucleases and phosphatases, and (d) incubating the cell lysate produced in (c) in the presence of an energy source and an engineered DNA template containing a promoter operably linked to a nucleotide sequence encoding a RNA of interest, under conditions that result in production of nucleoside triphosphates and polymerization of the nucleoside triphosphates, thereby producing a cell lysate that comprises the mRNA of interest.

Alternatively, such methods may comprise (a) combining cell lysates obtained from engineered cells that comprise endogenous, polymeric RNA, an enzyme that depolymerizes RNA, thermostable nucleoside monophosphate (NMP) kinases, thermostable nucleoside diphosphate (NDP) kinases, a thermostable PPK2 kinase, and/or a polyphosphate, to produce a cell lysate mixture, (b) incubating the cell lysate mixture produced in step (a) under conditions that result in depolymerization of RNA, thereby producing a cell lysate that comprises nucleoside monophosphates, (c) heating the cell lysate produced in step (b) to a temperature that inactivates phosphatases and RNases (and any other activities that may be detrimental to RNA stability or polymerization fidelity, such as native RNA polymerase, NMP reductases, and/or nucleosides) without inactivating the thermostable kinase and thermostable RNA polymerase, thereby producing a cell lysate that comprises heat-inactivated phosphatases and RNases (and other deleterious cellular activities), and (d) incubating the cell lysate produced in step (c) in the presence of an energy source and an engineered DNA template containing a promoter operably linked to a nucleotide sequence encoding a RNA of interest, under conditions that result in production of nucleoside triphosphates and polymerization of the nucleoside triphosphates, thereby producing a cell lysate that comprises mRNA.

In some embodiments, the DNA template encoding the RNA containing a single target domain is transcribed using a DNA-dependent RNA polymerase, such as, for example, a T7 RNA polymerase, and the resulting RNA transcript serves as a template for a RNA-dependent RNA polymerase, such as, for example, the phage Φ6 RdRP, to synthesize a complementary RNA molecule, yielding a dsRNA. See, e.g., FIG. 3B. Phage Φ6 is a double stranded RNA virus that infects members of the genus *Pseudomonas*. This phage encodes an RdRP that is capable of synthesizing RNA using a RNA template, yielding a dsRNA molecule. The Φ6 RdRP is capable of polymerizing RNA absent a primer molecule, thus the polymerase requires only template RNA (Wright, S. et al, 2012. *Journal of Virology. March;* 86(5):2837-49; Van Dijk, A A., et al, 2004. *J Gen Virol.* May; 85 (Pt 5), incorporated herein by reference). Other RNA-dependent RNA polymerase (RdRP) are encompassed by the present disclosure.

In some embodiments, the engineered cells comprise a DNA template encoding the RNA of interest. A DNA template encoding the RNA may be integrated into the genomic DNA of the engineered cells, or a DNA template may be introduced into the engineered cells on a plasmid. In other embodiments, the DNA template is added to the cell lysate during biosynthesis of the RNA of interest (e.g., following a heat inactivation step). In some embodiments, the concentration of the DNA template in a cell lysate is 0.05-1 µg/µl. In some embodiments, the concentration of the DNA template in a cell lysate is 0.05 µg/µl, 0.1 µg/µl, 0.5 µg/µl, 1.0 µg/µl.

As discussed above, other examples of RNA end products of interest include messenger RNA (mRNA) and short/small-interfering RNA (siRNA) (a synthetic RNA duplex designed to specifically target a particular mRNA for degradation).

In some embodiments, the concentration of RNA end product (biosynthesized RNA of interest) is at least 1 g/L to 50 g/L of cell lysate. For example, the concentration of RNA end product may be 1, 5, 10, 15, 20, 25, 30, 35, 40, 45, or 50 g/L, or more.

In some embodiments, a RNA of interest is designed to bind to a target nucleic acid of interest and is used, for example, as a therapeutic, prophylactic, or diagnostic agent.

Protease Targeting

Engineered cells of the present disclosure may express (e.g., endogenously express) enzymes necessary for the health of the cells that may have a negative impact on the production of nucleic acids, such as RNA. Such enzymes are referred to herein as "target enzymes." For example, target enzymes expressed by engineered cells may compete for substrates or cofactors with an enzyme that increases the rate of precursor supplied to a RNA biosynthetic pathway. As another example, target enzymes expressed by the engineered cells may compete for substrates or cofactors with an enzyme that is a key pathway entry enzyme of a RNA biosynthetic pathway. As yet another example, target enzymes expressed by the engineered cells may compete for substrates or cofactors with an enzyme that supplies a substrate or cofactor of a RNA biosynthetic pathway.

To negate, or reduce, this negative impact, target enzymes can be modified to include a site-specific protease-recognition sequence in their protein sequence such that the target enzyme may be "targeted" and cleaved for inactivation during RNA production (see, e.g., U.S. Publication No. 2012/0052547 A1, published on Mar. 1, 2012; and International Publication No. WO 2015/021058 A2, published Feb. 12, 2015, each of which is incorporated by reference herein).

Cleavage of a target enzyme containing a site-specific protease-recognition sequence results from contact with a cognate site-specific protease is sequestered in the periplasm of cell (separate from the target enzyme) during the cell growth phase (e.g., as engineered cells are cultured) and is brought into contact with the target enzyme during the RNA production phase (e.g., following cell lysis to produce a cell lysate). Thus, engineered cells of the present disclosure comprise, in some embodiments, (i) an engineered nucleic acid encoding a target enzyme that negatively impacts the rate of RNA production and includes a site-specific protease-recognition sequence in the protein sequence of the target enzyme, and (ii) an engineered nucleic acid encoding a site-specific protease that cleaves the site-specific protease-recognition sequence of the target enzyme and includes a periplasmic-targeting sequence. This periplasmic-targeting sequence is responsible for sequestering the site-specific protease to the periplasmic space of the cell until the cell is lysed. Examples of periplasmic-targeting sequences are provided below.

Examples of proteases that may be used in accordance with the present disclosure include, without limitation, alanine carboxypeptidase, proteases obtained from *Armillaria mellea*, astacin, bacterial leucyl aminopeptidase, cancer procoagulant, cathepsin B, clostripain, cytosol alanyl aminopeptidase, elastase, endoproteinase Brg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2B, picornain 3C, proendopeptidase, prolyl aminopeptidase, proprotein convertase I, proprotein convertase II, russellysin, saccharopepsin, semenogelase, T-plasminogen activator, thrombin, tissue kallikrein, proteases obtained from tobacco etch virus (TEV), togavirin, tryptophanyl aminopeptidase, U-plasminogen activator, V8, venombin B, venombin BB and Xaa-pro aminopeptidase.

Periplasmic Targeting

Enzymes of a nucleic acid (e.g., RNA) biosynthetic pathway may include at least one enzyme that has a negative impact on the health (e.g., viability) of a cell. To negate or reduce this negative impact, an enzyme can be modified to include a relocation sequence such that the enzyme is relocated to a cellular or extra-cellular compartment where it is not naturally located and where the enzyme does not negatively impact the health of the cell (see, e.g., Publication No. US-2011-0275116-A1, published on Nov. 10, 2011, incorporated by reference herein). For example, an enzyme of a biosynthetic pathway may be relocated to the periplasmic space of a cell.

Thus, in some embodiments, engineered cells of the present disclosure comprise at least one enzyme of a nucleic acid (e.g., RNA) biosynthetic pathway that is linked to a periplasmic-targeting sequence. A "periplasmic-targeting sequence" is an amino acid sequence that targets to the periplasm of a cell the protein to which it is linked. A protein that is linked to a periplasmic-targeting sequence will be sequestered in the periplasm of the cell in which the protein is expressed.

Periplasmic-targeting sequences may be derived from the N-terminus of bacterial secretory protein, for example. The sequences vary in length from about 15 to about 70 amino acids. The primary amino acid sequences of periplasmic-targeting sequences vary, but generally have a common structure, including the following components: (i) the N-terminal part has a variable length and generally carries a net positive charge; (ii) following is a central hydrophobic core of about 6 to about 15 amino acids; and (iii) the final component includes four to six amino acids which define the cleavage site for signal peptidases.

Periplasmic-targeting sequences of the present disclosure, in some embodiments, may be derived from a protein that is secreted in a Gram negative bacterium. The secreted protein may be encoded by the bacterium, or by a bacteriophage that infects the bacterium. Examples of Gram negative bacterial sources of secreted proteins include, without limitation, members of the genera *Escherichia, Pseudomonas, Klebsiella, Salmonella, Caulobacter, Methylomonas, Acetobacter, Achromobacter, Acinetobacter, Aeromonas, Agrobacterium, Alcaligenes, Azotobacter, Burkholderia, Citrobacter, Comamonas, Enterobacter, Erwinia, Rhizobium, Vibrio*, and *Xanthomonas*.

Examples of periplasmic-targeting sequences for use in accordance with the present disclosure include, without limitation, sequences selected from the group consisting of: MKIKTGARILALSALTTMMFSASALA (SEQ ID NO: 19); MKQSTIALALLPLLFTPVTKA (SEQ ID NO: 20); MMITLRKLPLAVAVAAGVMSAQAMA (SEQ ID NO: 21); MNKKVLTLSAVMASMLFGAAAHA (SEQ ID NO: 22); MKYLLPTAAAGLLLLAAQPAMA (SEQ ID NO: 23); MKKIWLALAGLVLAFSASA (SEQ ID NO: 24); MMTKIKLLMLIIFYLIISASAHA (SEQ ID NO: 25); MKQALRVAFGFLILWASVLHA (SEQ ID NO: 26); MRVLLFLLLSLFMLPAFS (SEQ ID NO: 27); and MANNDLFQASRRRFLAQLGGLTVAGMLGPSLLTPRRATA (SEQ ID NO: 28).

Engineered Cells

Engineered cells of the present disclosure typically comprise at least one, most, or all, of the enzymatic activities required to biosynthesize RNA. "Engineered cells" are cells that comprise at least one engineered (e.g., recombinant or synthetic) nucleic acid, or are otherwise modified such that they are structurally and/or functionally distinct from their naturally-occurring counterparts. Thus, a cell that contains an engineered nucleic acid is considered an "engineered cell."

Engineered cells of the present disclosure, in some embodiments, comprise RNA, enzymes that depolymerizes RNA, thermostable kinases, and/or thermostable polymerases. In some embodiments, the engineered cells further comprise a DNA template containing a promoter operably linked to a nucleotide sequence encoding a RNA of interest.

Engineered cells, in some embodiments, express selectable markers. Selectable markers are typically used to select engineered cells that have taken up and expressed an engineered nucleic acid following transfection of the cell (or following other procedure used to introduce foreign nucleic acid into the cell). Thus, a nucleic acid encoding product may also encode a selectable marker. Examples of selectable markers include, without limitation, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds. Additional examples of selectable markers include, without limitation, genes encoding proteins that enable the cell to grow in media deficient in an otherwise essential nutrient (auxotrophic markers). Other selectable markers may be used in accordance with the present disclosure.

An engineered cell "expresses" a product if the product, encoded by a nucleic acid (e.g., an engineered nucleic acid), is produced in the cell. It is known in the art that gene expression refers to the process by which genetic instructions in the form of a nucleic acid are used to synthesize a product, such as a protein (e.g., an enzyme).

Engineered cells may be prokaryotic cells or eukaryotic cells. In some embodiments, engineered cells are bacterial cells, yeast cells, insect cells, mammalian cells, or other types of cells.

Engineered bacterial cells of the present disclosure include, without limitation, engineered *Escherichia* spp., *Streptomyces* spp., *Zymomonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp.

Engineered yeast cells of the present disclosure include, without limitation, engineered *Saccharomyces* spp., *Schizosaccharomyces, Hansenula. Candida. Kluyveromyces. Yarrowia* and *Pichia*.

In some embodiments, engineered cells of the present disclosure are engineered *Escherichia coli* cells, *Bacillus subtilis* cells, *Pseudomonas putida* cells, *Saccharomyces cerevisae* cells, or *Lactobacillus brevis* cells. In some embodiments, engineered cells of the present disclosure are engineered *Escherichia coli* cells.

Engineered Nucleic Acids

A "nucleic acid" is at least two nucleotides covalently linked together, and in some instances, may contain phosphodiester bonds (e.g., a phosphodiester "backbone"). Nucleic acids (e.g., components, or portions, of nucleic acids) may be naturally occurring or engineered. "Naturally occurring" nucleic acids are present in a cell that exists in nature in the absence of human intervention. "Engineered nucleic acids" include recombinant nucleic acids and synthetic nucleic acids. A "recombinant nucleic acid" refers to a molecule that is constructed by joining nucleic acid molecules (e.g., from the same species or from different species) and, typically, can replicate in a living cell. A "synthetic nucleic acid" refers to a molecule that is biologically synthesized, chemically synthesized, or by other means synthesized or amplified. A synthetic nucleic acid includes nucleic acids that are chemically modified or otherwise modified but can base pair with naturally-occurring nucleic acid molecules. Recombinant and synthetic nucleic acids also include those molecules that result from the replication of either of the foregoing. Engineered nucleic acids may contain portions of nucleic acids that are naturally occurring, but as a whole, engineered nucleic acids do not occur naturally and require human intervention. In some embodiments, a nucleic acid encoding a product of the present disclosure is a recombinant nucleic acid or a synthetic nucleic acid. In other embodiments, a nucleic acid encoding a product is naturally occurring.

An engineered nucleic acid encoding RNA, as provided herein, may be operably linked to a "promoter," which is a control region of a nucleic acid at which initiation and rate of transcription of the remainder of a nucleic acid are controlled. A promoter drives expression or drives transcription of the nucleic acid that it regulates.

A promoter may be one naturally associated with a gene or sequence, as may be obtained by isolating the 5' non-coding sequences located upstream of the coding segment of a given gene or sequence. Such a promoter can be referred to as "endogenous."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR).

A promoter is considered to be "operably linked" when it is in a correct functional location and orientation in relation to the nucleic acid it regulates to control ("drive") transcriptional initiation and/or expression of that nucleic acid.

Engineered nucleic acids of the present disclosure may contain a constitutive promoter or an inducible promoter. A "constitutive promoter" refers to a promoter that is constantly active in a cell. An "inducible promoter" refers to a promoter that initiates or enhances transcriptional activity when in the presence of, influenced by, or contacted by an inducer or inducing agent, or activated in the absence of a factor that causes repression. Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters, steroid-regulated promoters, metal-regulated promoters, pathogenesis-regulated promoters, temperature/heat-inducible, phosphate-regulated (e.g., PhoA), and light-regulated promoters.

An inducer or inducing agent may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

Engineered nucleic acids may be introduced into host cells using any means known in the art, including, without limitation, transformation, transfection (e.g., chemical (e.g., calcium phosphate, cationic polymers, or liposomes) or non-chemical (e.g., electroporation, sonoporation, impalefection, optical transfection, hydrodynamic transfection)), and transduction (e.g., viral transduction).

Enzymes or other proteins encoded by a naturally-occurring, intracellular nucleic acid may be referred to as "endogenous enzymes" or "endogenous proteins."

Cell Cultures and Cell Lysates

Typically, engineered cells are cultured. "Culturing" refers to the process by which cells are grown under controlled conditions, typically outside of their natural environment. For example, engineered cells, such as engineered bacterial cells, may be grown as a cell suspension in liquid nutrient broth, also referred to as liquid "culture medium."

Examples of commonly used bacterial *Escherichia coli* growth media include, without limitation, LB (Lysogeny Broth) Miller broth (1% NaCl): 1% peptone, 0.5% yeast extract, and 1% NaCl; LB (Lysogeny Broth) Lennox Broth (0.5% NaCl); 1% peptone, 0.5% yeast extract, and 0.5% NaCl; SOB medium (Super Optimal Broth): 2% peptone, 0.5% Yeast extract, 10 mM NaCl, 2.5 mM KCl, 10 mM $MgCl_2$, 10 mM $MgSO_4$; SOC medium (Super Optimal broth with Catabolic repressor): SOB+20 mM glucose; 2×YT broth (2× Yeast extract and Tryptone): 1.6% peptone, 1% yeast extract, and 0.5% NaCl; TB (Terrific Broth) medium: 1.2% peptone, 2.4% yeast extract, 72 mM $K_2HPO_4$, 17 mM $KH_2PO_4$ and 0.4% glycerol; and SB (Super Broth) medium: 3.2% peptone, 2% yeast extract, and 0.5% NaCl and or Korz medium (Korz, D J et al. 1995).

Examples of high density bacterial *Escherichia coli* growth media include, but are not limited to, DNAGro™ medium, ProGro™ medium, AutoX™ medium. DetoX™ medium, InduX™ medium, and SecPro™ medium.

In some embodiments, engineered cells are cultured under conditions that result in expression of enzymes or nucleic acids. Such culture conditions may depend on the particular product being expressed and the desired amount of the product.

In some embodiments, engineered cells are cultured at a temperature of 30° C. to 40° C. For example, engineered cells may be cultured at a temperature of 30° C., 31° C., 32° C., 33° C., 34° C., 35° C., 36° C., 37° C., 38° C., 39° C. or 40° C. Typically, engineered cells, such as engineered *E. coli* cells, are cultured at a temperature of 37° C.

In some embodiments, engineered cells are cultured for a period of time of 12 hours to 72 hours, or more. For example, engineered cells may be cultured for a period of time of 12, 18, 24, 30, 36, 42, 48, 54, 60, 66, or 72 hours. Typically, engineered cells, such as engineered bacterial cells, are cultured for a period of time of 12 to 24 hours. In some embodiments, engineered cells are cultured for 12 to 24 hours at a temperature of 37° C.

In some embodiments, engineered cells are cultured (e.g., in liquid cell culture medium) to an optical density, measured at a wavelength of 600 nm (OD600), of 5 to 200. In some embodiments, engineered cells are cultured to an OD600 of 5, 10, 15, 20, 25, 50, 75, 100, 150, or 200.

In some embodiments, engineered cells are cultured to a density of $1 \times 10^8$ (OD<1) to $2 \times 10^{11}$ (OD~200) viable cells/ml cell culture medium. In some embodiments, engineered cells are cultured to a density of $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, or $2 \times 10^{11}$ viable cells/ml. (Conversion factor: OD $1=8 \times 10^8$ cells/ml).

In some embodiments, engineered cells are cultured in a bioreactor. A bioreactor refers simply to a container in which cells are cultured, such as a culture flask, a dish, or a bag that may be single-use (disposable), autoclavable, or sterilizable. The bioreactor may be made of glass, or it may be polymer-based, or it may be made of other materials.

Examples of bioreactors include, without limitation, stirred tank (e.g., well mixed) bioreactors and tubular (e.g., plug flow) bioreactors, airlift bioreactors, membrane stirred tanks, spin filter stirred tanks, vibromixers, fluidized bed reactors, and membrane bioreactors. The mode of operating the bioreactor may be a batch or continuous processes and will depend on the engineered cells being cultured. A bioreactor is continuous when the feed and product streams are continuously being fed and withdrawn from the system. A batch bioreactor may have a continuous recirculating flow, but no continuous feeding of nutrient or product harvest. For intermittent-harvest and fed-batch (or batch fed) cultures, cells are inoculated at a lower viable cell density in a medium that is similar in composition to a batch medium. Cells are allowed to grow exponentially with essentially no external manipulation until nutrients are somewhat depleted and cells are approaching stationary growth phase. At this point, for an intermittent harvest batch-fed process, a portion of the cells and product may be harvested, and the removed culture medium is replenished with fresh medium. This process may be repeated several times. For production of recombinant proteins and antibodies, a fed-batch process may be used. While cells are growing exponentially, but nutrients are becoming depleted, concentrated feed medium (e.g., 10-15 times concentrated basal medium) is added either continuously or intermittently to supply additional nutrients, allowing for further increase in cell concentration and the length of the production phase. Fresh medium may be added proportionally to cell concentration without removal of culture medium (broth). To accommodate the addition of medium, a fedbatch culture is started in a volume much lower that the full capacity of the bioreactor (e.g., approximately 40% to 50% of the maximum volume).

Some methods of the present disclosure are directed to large-scale production of RNA (e.g., ssRNA or dsRNA). For large-scale production methods, engineered cells may be grown in liquid culture medium in a volume of 5 liters (L) to 250,000 L, or more. In some embodiments, engineered cells may be grown in liquid culture medium in a volume of greater than (or equal to) 10 L, 100 L, 1000 L, 10000 L, or 100000 L. In some embodiments, engineered cells are grown in liquid culture medium in a volume of 5 L, 10 L, 15 L, 20 L, 25 L, 30 L, 35 L, 40 L, 45 L, 50 L, 100 L, 500 L, 1000 L, 5000 L, 10000 L, 100000 L, 150000 L, 200000 L, 250000 L, or more. In some embodiments, engineered cells may be grown in liquid culture medium in a volume of 5 L to 10 L, 5 L to 15 L, 5 L to 20 L, 5 L to 25 L, 5 L to 30 L, 5 L to 35 L, 5 L to 40 L, 5 L to 45 L, 10 L to 15 L, 10 L to 20 L, 10 L to 25 L, 20 L to 30 L, 10 L to 35 L, 10 L to 40 L, 10 L to 45 L, 10 L to 50 L, 15 L to 20 L, 15 L to 25 L, 15 L to 30 L, 15 L to 35 L, 15 L to 40 L, 15 L to 45 L, or 15 L to 50 L. In some embodiments, engineered cells may be grown in liquid culture medium in a volume of 100 L to 300000 L, 100 L to 200000 L, or 100 L to 100000 L.

Typically, culturing of engineered cells is followed by lysing the cells. "Lysing" refers to the process by which cells are broken down, for example, by viral, enzymatic, mechanical, or osmotic mechanisms. A "cell lysate" refers to a fluid containing the contents of lysed cells (e.g., lysed engineered cells), including, for example, organelles, membrane lipids, proteins, nucleic acids and inverted membrane vesicles. Cell lysates of the present disclosure may be produced by lysing any population of engineered cells, as provided herein.

Methods of cell lysis, referred to as "lysing," are known in the art, any of which may be used in accordance with the present disclosure. Such cell lysis methods include, without limitation, physical lysis such as homogenization.

Cell lysis can disturb carefully controlled cellular environments, resulting in protein degradation and modification by unregulated endogenous proteases and phosphatases. Thus, in some embodiments, protease inhibitors and/or phosphatase inhibitors may be added to the cell lysate or cells before lysis, or these activities may be removed by heat inactivation, gene inactivation, or protease targeting.

Cell lysates, in some embodiments, may be combined with at least one nutrient. For example, cell lysates may be combined with $Na_2HPO_4$, $KH_2PO_4$, $NH_4Cl$, NaCl, $MgSO_4$, $CaCl_2$. Examples of other nutrients include, without limitation, magnesium sulfate, magnesium chloride, magnesium orotate, magnesium citrate, potassium phosphate monobasic, potassium phosphate dibasic, potassium phosphate tribasic, sodium phosphate monobasic, sodium phosphate dibasic, sodium phosphate tribasic, ammonium phosphate monobasic, ammonium phosphate dibasic, ammonium sulfate, ammonium chloride, and ammonium hydroxide.

Cell lysates, in some embodiments, may be combined with at least one cofactor. For example, cell lysates may be combined with adenosine diphosphate (ADP), adenosine triphosphate (ATP), nicotinamide adenine dinucleotide (NAD+), or other non-protein chemical compounds required for activity of an enzyme (e.g., inorganic ions and coenzymes).

In some embodiments, cell lysates are incubated under conditions that result in RNA depolymerization. In some embodiments, cell lysates are incubated under conditions that result in production of ssRNA or dsRNA.

The volume of cell lysate used for a single reaction may vary. In some embodiments, the volume of a cell lysate is 0.001 to 250 $m^3$. For example, the volume of a cell lysate may be 0.001 $m^3$, 0.01 $m^3$, 0.1 $m^3$, 1 $m^3$, 5 $m^3$, 10 $m^3$, 15 $m^3$, 20 $m^3$, 25 $m^3$, 30 $m^3$, 35 $m^3$, 40 $m^3$, 45 $m^3$, 50 $m^3$, 55 $m^3$, 60 $m^3$, 65 $m^3$, 70 $m^3$, 75 $m^3$, 80 $m^3$, 85 $m^3$, 90 $m^3$, 95 $m^3$, 100 $m^3$, 105 $m^3$, 110 $m^3$, 115 $m^3$, 120 $m^3$, 125 m, 130 $m^3$, 135 $m^3$, 140 $m^3$, 145 $m^3$, 150 $m^3$, 155 m, 160 $m^3$, 165 $m^3$, 170 $m^3$, 175 $m^3$, 180 $m^3$, 185 $m^3$, 190 $m^3$, 195 $m^3$, 200 $m^3$, 205 $m^3$, 210 $m^3$, 215 m, 220 $m^3$, 225 $m^3$, 230 $m^3$, 235 $m^3$, 240 $m^3$, 245 $m^3$, or 250 $m^3$. In some embodiments, the volume of a cell lysate is 25 $m^3$ to 250 $m^3$, 50 $m^3$ to 250 $m^3$, or 100 $m^3$ to 250 $m^3$.

Downstream Processing

Figure 4:
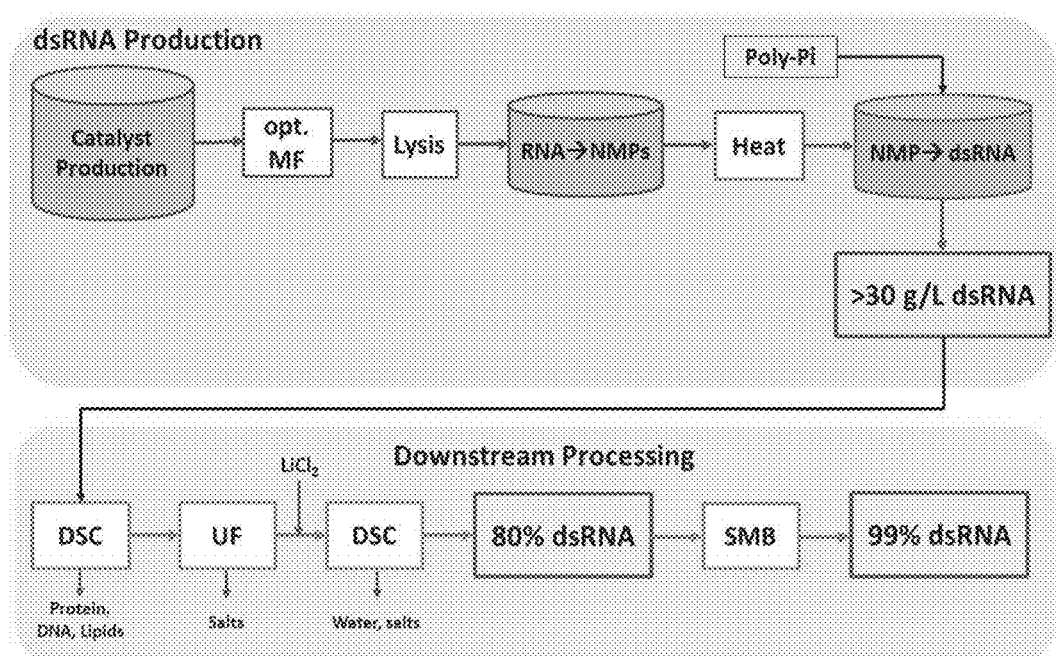
FIG. 4 shows a schematic of another example of a cell-free RNA production method of the present disclosure. The process starts with a single fermentation vessel in which engineered cells are produced using standard fermentation techniques. Biomass generated from the fermentation is optionally concentrated by microfiltration (MF) followed by lysis via mechanical homogenization, for example. The lysate is then pumped into a second fermentation vessel wherein the expressed nuclease enzymes convert RNA to its monomeric constituents. The entire reaction is heated to inactivate any endogenous phosphatase or nuclease (e.g., RNase) activities as well as any other exogenous/introduced cellular (e.g., nuclease) activity that would be detrimental to RNA product stability and/or fidelity. Following heat inactivation, polyphosphate is fed to the reaction as a source of high-energy phosphate for the phosphorylation of NMPs to NTPs via a series of thermostable kinases, followed by polymerization to dsRNA. Downstream processing may be used to increase purity to as much as 99% (e.g., 50%, 60%, 70%, 80%, 90%, 95%, 98%, or 99%) dsRNA by weight. For example, processing may be used to increase purity to 50-60%, 50-70%, 50-80%, 50-90%, 50-95%, 70-80%, 70-90%, or 70-95%. An exemplary downstream process starts with the addition of a protein precipitating agent (e.g., ammonium acetate) followed by removal of protein, lipids and some DNA from the product stream by disc stack centrifugation (DSC) or tangential flow filtration (TFF). Ultrafiltration is then implemented to remove salts and reduce volume. Addition of lithium chloride to the product stream leads to precipitation of the dsRNA product, is subsequently be separated from the bulk liquid using disc stack centrifugation, yielding an 80% purity dsRNA product stream. Further chromatographic polishing yields a 99% pure product (Nilsen, T W. *Cold Spring Harb Protoc.* 2012 Dec. 1; 2012(12)).

The methods and systems provided herein, in some embodiments, yield RNA (e.g., dsRNA, ssRNA) product at a concentration of 1-50 g/L (e.g., 30, 35, 40, 45, or 50 g/L). Downstream processing increases purity to as much as 99% (e.g., 75, 80, 85, 90, 95, 96, 97, 98, or 99%) dsRNA by weight. An example of downstream processing is shown in FIG. 4, starting with the addition of a protein precipitating agent (e.g., ammonium acetate) followed by disc-stack centrifugation (DSC) to remove protein, lipids, and some DNA from the product stream. Ultrafiltration is then implemented to remove salts and volume. Addition of lithium chloride to the product stream leads to precipitation of the RNA product, which is subsequently separated from the bulk liquid using disc stack centrifugation, for example, yielding an ~80% purity RNA product stream. Further chromatographic polishing yield a ~99% pure product.

Additional Embodiments

Additional embodiments of the present disclosure are encompassed by the following numbered paragraphs 1-46:

1. A cell-free method of biosynthesizing ribonucleic acid (RNA), the method comprising:
   (a) lysing cultured engineered cells that comprise RNA, an enzyme that depolymerizes RNA, thermostable kinases, a thermostable RNA polymerase, thereby producing a cell lysate;
   (b) incubating the cell lysate produced in step (a) under conditions that result in depolymerization of RNA, thereby producing a cell lysate that comprises nucleoside monophosphates;
   (c) heating the cell lysate produced in step (b) to a temperature that inactivates endogenous nucleases and phosphatases without inactivating the thermostable kinases and thermostable RNA polymerase, thereby producing a cell lysate that comprises heat-inactivated nucleases and phosphatases; and
   (d) incubating the cell lysate produced in (c) in the presence of an energy source and an engineered DNA template containing a promoter operably linked to a nucleotide sequence encoding a RNA of interest, under conditions that result in production of nucleoside triphosphates and polymerization of the nucleoside triphosphates, thereby producing a cell lysate that comprises the RNA of interest.

2. The method of paragraph 1, wherein the energy source is polyphosphate, polyphosphate kinase, or both polyphosphate and polyphosphate kinase.

3. The method of paragraph 1 or 2, wherein the cultured engineered cells comprise the engineered DNA template.

4. The method of paragraph 1 or 2, wherein the engineered DNA template is added to the cell lysate of step (d).

5. The method of any one of paragraphs 1-4, wherein an ATP regeneration system is added to the cell lysate of step (d).

6. The method of paragraph 1, wherein the cultured engineered cells further comprise a thermostable polyphosphate kinase.

7. The method of any one of paragraphs 1-6, wherein the RNA of the engineered cells of step (a) is endogenous RNA.

8. The method of any one of paragraphs 1-7, wherein the RNA comprises ribosomal RNA, messenger RNA, transfer RNA, or a combination thereof.

9. The method of any one of paragraphs 1-8, wherein the cultured engineered cells comprise at least two enzymes that depolymerize RNA.

10. The method of any one of paragraphs 1-9, wherein the enzyme that depolymerizes RNA is selected from the group consisting of: S1 nuclease, Nuclease P1, RNase II, RNase III, RNase R, RNase JI, NucA, PNPase, RNase T, RNase E, RNaseG and combinations thereof.

11. The method of paragraph 10, wherein the enzyme that depolymerizes RNA is Nuclease P1.

12. The method of any one of paragraphs 1-11, wherein the cell lysate of step (b) comprises a $Mg^{2+}$ chelating agent.

13. The method of paragraph 12, wherein the $Mg^{2+}$ chelating agent is ethylenediaminetetraacetic acid (EDTA).

14. The method of paragraph 13, wherein the concentration of the EDTA is 0.1 mM to 25 mM.

15. The method of paragraph 14, wherein the concentration of the EDTA is 8 mM.

16. The method of any one of paragraphs 1-15, wherein the thermostable kinases comprise thermostable nucleoside monophosphate kinases.

17. The method of paragraph 16, wherein the thermostable nucleoside monophosphate kinases are selected from the group consisting of thermostable uridylate kinases, thermostable cytidylate kinases, thermostable guanylate kinases, and thermostable adenylate kinases.

18. The method of paragraph 17, wherein the stable nucleoside monophosphate kinases a selected from the group consisting of a thermostable *Pyrococcus furiosus* uridylate kinase encoded by a pyrH gene (PfPyrH), a thermostable *Thermus thermophilus* adenylate kinase encoded by a adk gene (TthAdk), a thermostable *Thermus thermophilus* cytidylate kinase encoded by a cmk gene (TthCmk), and a thermostable *Pyrococcus furiosus* guanylate kinase encoded by a gmk gene (PfGmk).

19. The method of any one of paragraphs 1-18, wherein the thermostable kinases comprise thermostable nucleoside diphosphate kinases.

20. The method of paragraph 19, wherein the thermostable nucleoside diphosphate kinases are selected from the group consisting of thermostable nucleoside phosphate kinases, thermostable pyruvate kinases, and thermostable polyphosphate kinases.

21. The method of paragraph 20, wherein at least one of the thermostable nucleoside diphosphate kinases is a thermostable *Aquifex aeolicus* enzyme encoded by a ndk gene.

22. The method of any one of paragraphs 1-21, wherein the cells comprise a thermostable nucleoside monophosphate kinase and a thermostable nucleoside diphosphate kinase.

23. The method of any one of paragraphs 1-22, wherein the cultured engineered cells comprise thermostable uridylate kinase, thermostable cytidylate kinase, thermostable guanylate kinase, thermostable adenylate kinase, and thermostable polyphosphate kinase.

24. The method of any one of paragraphs 1-23, wherein the thermostable RNA polymerase is a thermostable DNA-dependent RNA polymerase.

25. The method of paragraph 24, wherein the DNA-dependent RNA polymerase is selected from the group consisting of thermostable T7 RNA polymerases, thermostable SP6 RNA polymerases, and thermostable T3 RNA polymerases.

26. The method of paragraph 25, wherein the DNA-dependent RNA polymerase is a thermostable T7 RNA polymerase.

27. The method of any one of paragraphs 1-26, wherein the temperature in step (c) is at least 50° C.

28. The method of paragraph 27, wherein the temperature in step (c) is at 50° C.-80° C.

29. The method of any one of paragraphs 1-28, wherein step (c) comprises heating the cell lysate for at least 15 minutes.

30. The method of any one of paragraphs 1-29, wherein step (c) comprises heating the cell lysate to a temperature of at least 65° C. for 15 minutes.

31. The method of any one of paragraphs 1-30, wherein the nucleoside triphosphates in step (d) are produced at a rate of 15-30 mM/hour.

32. The method of any one of paragraphs 1-31, wherein the RNA of interest produced in step (d) is double-stranded RNA.

33. The method of any one of paragraphs 1-32, wherein the RNA of interest is produced in step (d) a RNA interference molecule.

34. The method of any one of paragraphs 1-33, wherein the RNA of interest produced in step (d) is an mRNA containing complementary domains linked by a hinged domain.

35. The method of any one of paragraphs 1-34, wherein the RNA of interest produced in step (d) is produced at a concentration of at least 4 g/L, at least 6 g/L, at least 6 g/L, or at least 10 g/L.

36. The method of paragraph 35 further comprising purifying the double-stranded RNA.

37. The method of paragraph 36, wherein the purifying step comprises combining the cell lysate of step (d) with a protein precipitating agent and removing precipitated protein, lipids, and DNA.

38. A cell lysate produced by the method of any one of paragraphs 1-37.

39. An engineered cell comprising RNA, an enzyme that depolymerizes RNA, a thermostable kinase and a thermostable RNA polymerase.

40. The engineered cell of paragraph 39 further comprising an engineered DNA template containing a promoter operably linked to a nucleotide sequence encoding a RNA of interest.

41. A population of engineered cells of paragraph 39 or 40.

42. A method, comprising:
maintaining in cell culture media engineered cells of paragraph 39.

43. The method of paragraph 42 further comprising lysing the cultured engineered cells to produce a cell lysate.

44. The method of paragraph 43 further comprising incubating the cell lysate under conditions that result in depolymerization of RNA to produce a cell lysate that comprises nucleoside monophosphates.

45. The method of paragraph 44 further comprising heating the cell lysate to a temperature that inactivates endogenous nucleases and phosphatases without inactivating the thermostable kinases and thermostable RNA polymerase to produce a cell lysate that comprises heat-inactivated nucleases and phosphatases.

46. The method of paragraph 45 further comprising incubating the cell lysate that comprises heat-inactivated nucleases and phosphatases in the presence of an energy source and an engineered DNA template containing a promoter operably linked to a nucleotide sequence encoding a RNA of interest, under conditions that result in production of nucleoside triphosphates and polymerization of the nucleoside triphosphates, to produce a cell lysate that comprises the RNA of interest.

EXAMPLES

Example 1

Nuclease Downselection

Figure 5A:
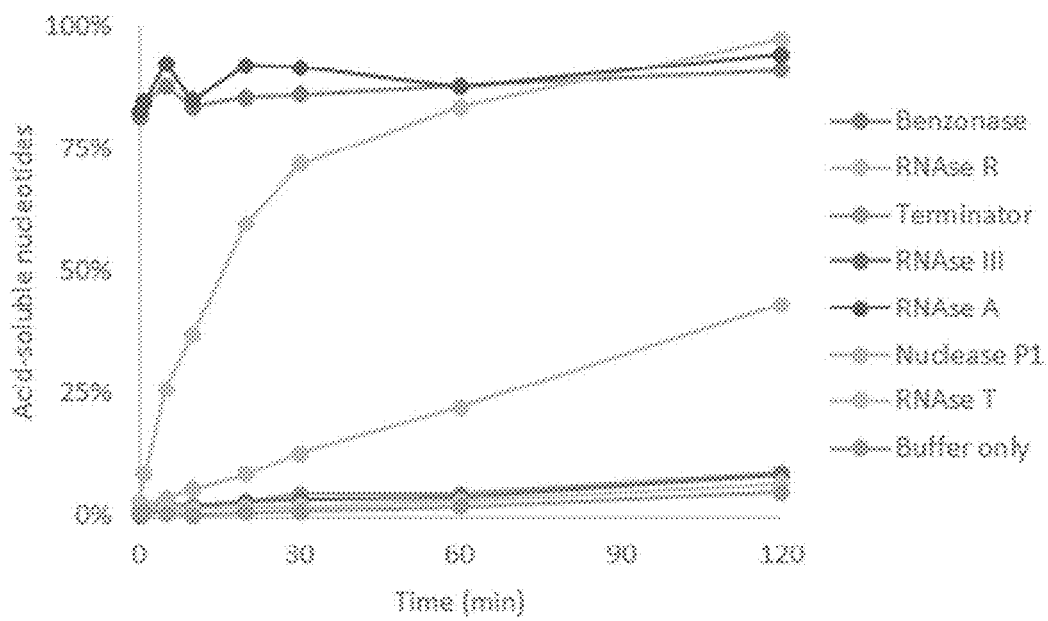
FIGS. 5A-5B show a comparison of ribonuclease activities by digestion of purified *E. coli* RNA.
Figure 5B:
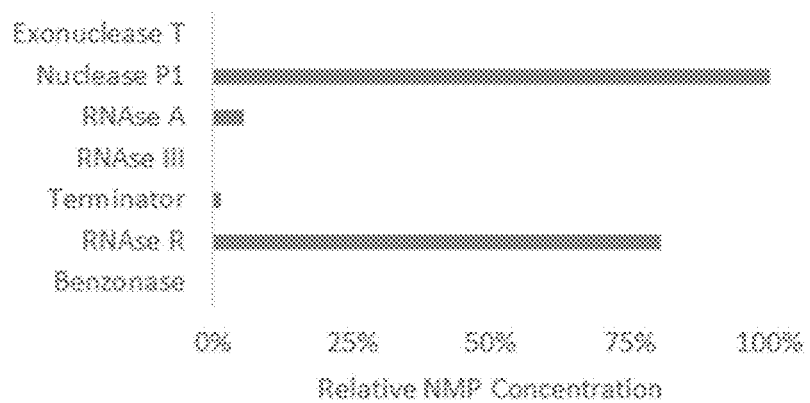

To identify the optimal nuclease(s) for digesting lysate RNA, a series of screening experiments were performed using commercially-available enzymes chosen based on their ability to generate 5'-NMPs or oligonucleotides. The activity of these enzymes was first determined using purified *E. coli* RNA and reaction conditions recommended by the manufacturer, where RNA depolymerization was monitored by the release of acid-soluble nucleotides. Under these conditions, four nucleases demonstrated depolymerization activity over background. The endonucleases Benzonase and RNase A, which served as positive controls, yielded immediate conversion of RNA to acid-soluble nucleotides (FIG. 5A). Treatment of RNA with the exonucleases P1 and RNase R yielded a time-dependent conversion of RNA to acid-soluble nucleotides, with RNase R reaching nearly 100% depolymerization in 2 hours. The remaining nucleases (terminator exonuclease, RNase III and RNase T) did not produce detectable depolymerization in this assay. Subsequent analyses by LC-MS revealed NMP liberation in samples treated with RNase R and Nuclease P1, but not Benzonase or RNase A (FIG. 5B). These results suggest that RNase R and Nuclease P1 may be suitable for depolymerizing lysate RNA into 5'-NMPs. RNase R was chosen for further study for several reasons, including its lack of DNAse activity, its ability to degrade dsRNA and structured RNA, and its processive 3'→5' exonuclease activity.

RNA Depolymerization in Lysates

Figure 6:
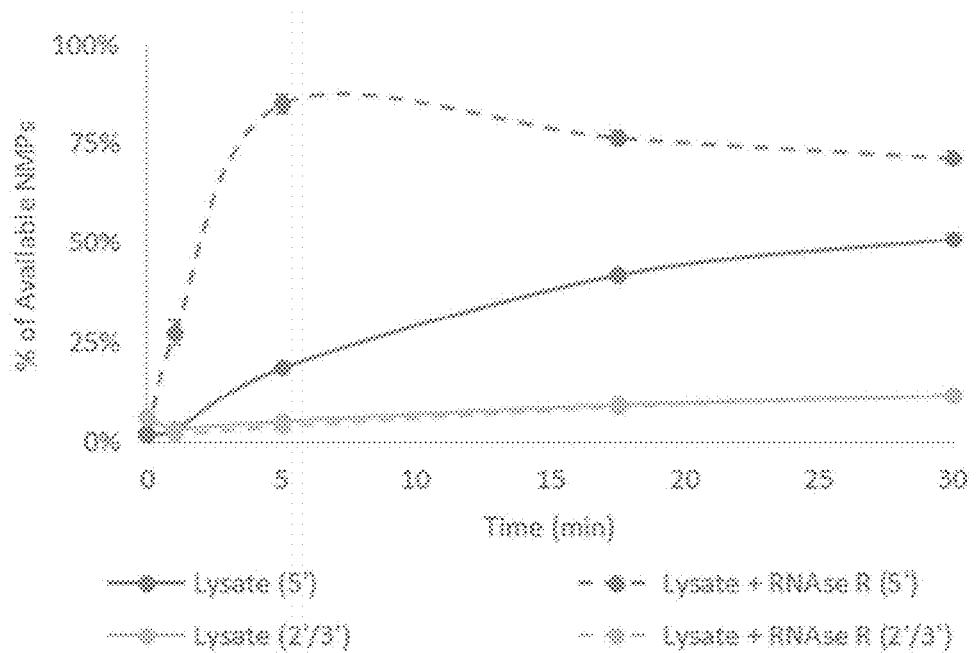
FIG. 6 is a graph showing depolymerization of lysate RNA using exogenous RNase R, with products analyzed by UPLC to specifically identify 5'-NMPs. In the absence of RNase R, lysates exhibited endogenous RNase activity that led to the slow accumulation of 5'-NMPs (solid dark gray line). Addition of exogenous RNase R led to rapid 5'-NMP release (dashed dark gray line) without affecting rates of 2' or 3' NMP accumulation (light gray lines). Thus, overexpression of RNase R accelerates the rate of polymeric RNA to 5'-NMP conversion, reducing the deleterious effects of phosphatase/nuclease activities present in the extract. Experiments were performed at a final concentration of 50% lysate.

RNase R was then tested for its ability to depolymerize endogenous RNA in bacterial lysates. In these experiments, purified RNase R (0.5 mg/mL final concentration) was added to lysates (50% final concentration), and free nucleotides were quantified by UPLC. A representative experiment is shown in FIG. 6. Adding purified RNase R to lysates resulted in the rapid release of 5'-NMPs from lysate RNA, with maximal NMP liberation after 5-10 minutes. After this initial period of rapid depolymerization, NMP concentrations stabilized, then began to slowly decline. Endogenous RNase activity also resulted in 5'-NMP liberation, albeit at much lower rates. Importantly, RNase R addition did not increase the rate of 2' or 3' NMP liberation from RNA, consistent with its known mechanism of action. Across multiple independent experiments, addition of RNase R to lysates resulted in the conversion of 68% of lysate RNA to 5'-NMPs in 5-10 minutes at rates in excess of 200 mM/hr.

Figure 7A:
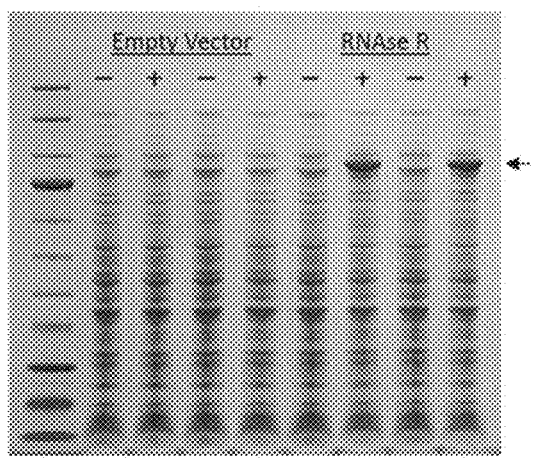
FIGS. 7A-7C show results of RNase R overexpression in 1 L bioreactors cultures grown in batch phase.
Figure 7B:
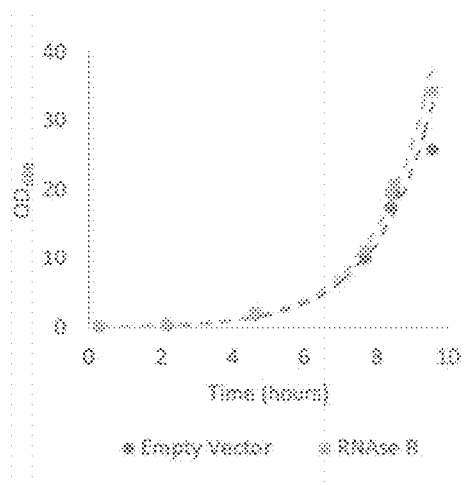
Figure 7C:
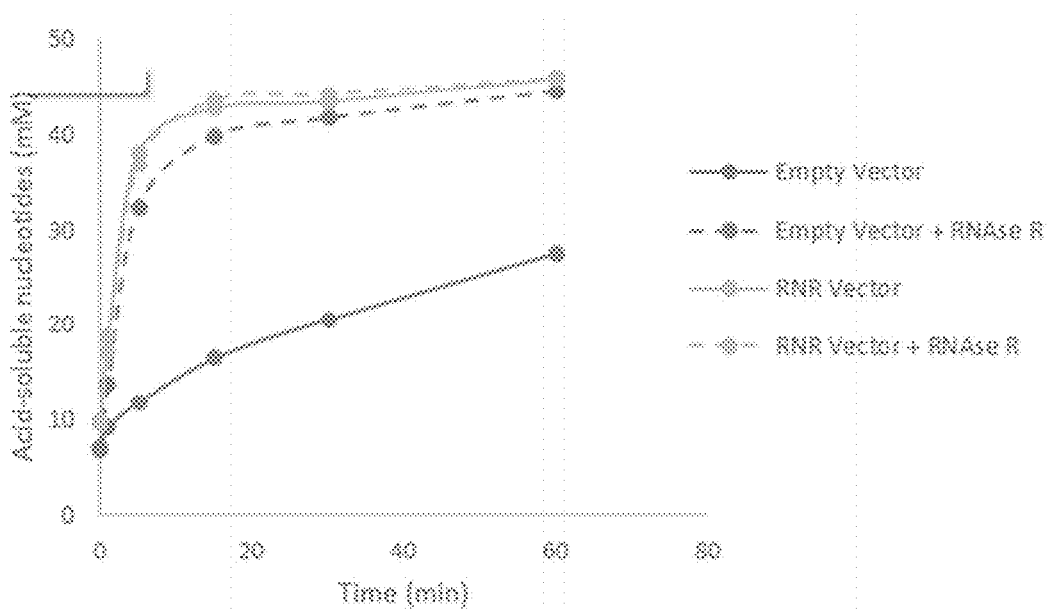

To assess the toxicity of RNase R expression, two bacterial strains were constructed. One strain included the base strain (GL16-170) transformed with an empty protein expression vector, and the other included GL16-170 transformed with the same protein expression vector encoding RNase R. Both strains were grown under batch conditions in 1 L bioreactors, induced at OD600=20, and harvested before glucose exhaustion. Induction yielded strong expression of RNase R (FIG. 7A) with no detectable change in growth rate (FIG. 7B). Upon lysis and 50% dilution, the strain expressing RNase R exhibited rapid depolymerization of RNA into acid-soluble nucleotides (FIG. 7C), indicating that overexpressed RNase R was functional. Notably, additional RNase R activity, which was supplied by adding purified enzyme to the reaction, did not increase rates of depolymerization or yields of acid-soluble nucleotides, suggesting that overexpressed RNase R is fully active upon lysis and dilution.

Figure 8:
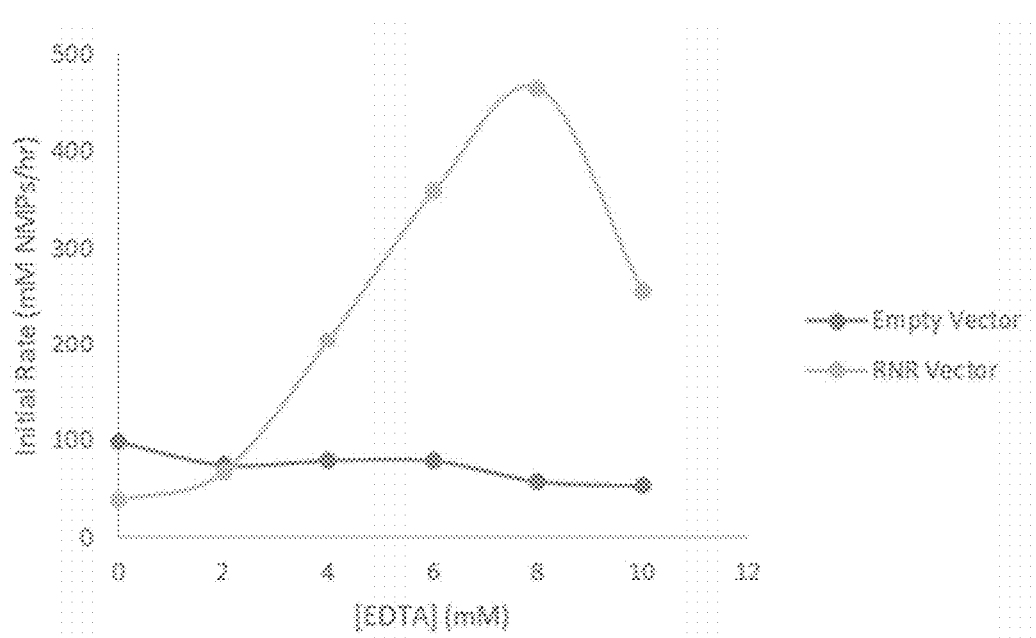
FIG. 8 is a graph describing the effects of chelating $Mg^{2+}$ on depolymerization rates in high-density lysates. Lysates prepared from biomass containing Empty Vector (dark gray) were insensitive to EDTA. Lysates with overexpressed RNase R (light gray) exhibited rapid RNA depolymerization with $Mg^{2+}$ removal, with 8 mM EDTA providing maximum depolymerization rates. Experiments were performed at a final concentration of 90% lysate.
Figure 9A:
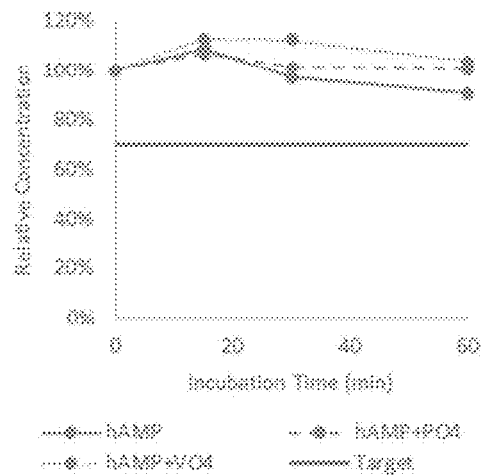
FIGS. 9A-9D show graphs demonstrating stability of exogenous isotopically-labeled "heavy" NMPs (hNMPs) in lysates.
Figure 9B:
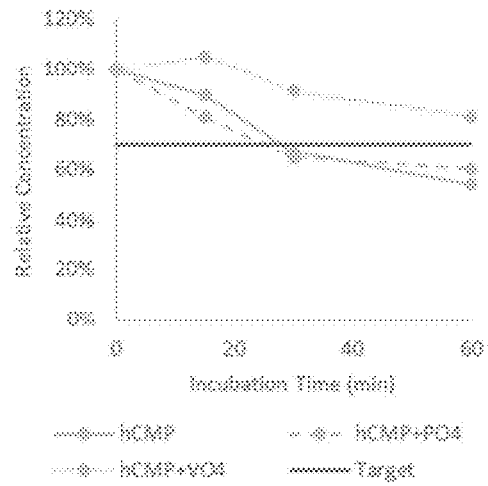
Figure 9C:
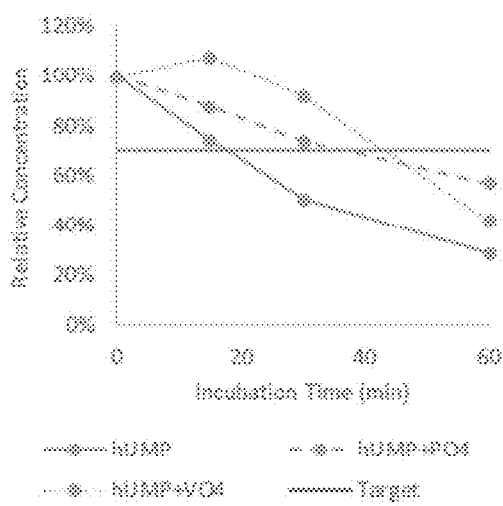
Figure 9D:
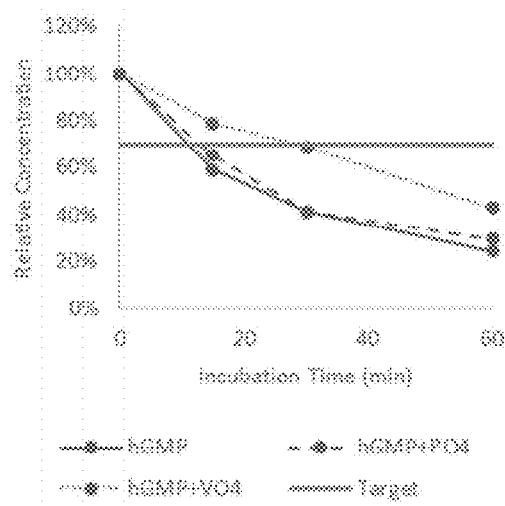

Next, the activity of overexpressed RNase R was assessed in high-density lysates. $Mg^{2+}$, which is known to stabilize ribosome structure and protect rRNA from nucleases, is also required (in low amounts) for RNase R activity. Therefore, depolymerization rates were measured in the presence of varying concentrations of EDTA (FIG. 8). Lysates from the empty vector strain exhibited relatively slow depolymerization rates that were insensitive to EDTA, while lysates with overexpressed RNase R exhibited higher rates of depolymerization with increasing EDTA concentration, with maximal rates at 8 mM EDTA. Above 8 mM, depolymerization rates decreased, likely due to inactivation of $Mg^{2+}$-dependent RNase R. Taken together, these results suggest that overexpressed RNase R is non-toxic and can be activated upon lysis.

NMP Stability in Lysates

After RNA depolymerization, the resulting NMP pool is progressively phosphorylated to NTPs before polymerization into dsRNA. Deleterious enzymatic activities, such as NMP degradation into nucleosides and subsequent hydrolysis into sugars and bases, negatively impact dsRNA yields. Therefore, the stability of individual NMPs was assessed in lysates. Stability assessments were performed by adding isotopically-labeled "heavy" NMPs (hAMP, hCMP, hUMP, and hGMP) to lysates, and quantifying abundance over time using LC-MS (Figured 9A-9D, solid lines). In contrast to hAMP, which is relatively stable, hCMP, hUMP, and hGMP are actively degraded by the lysate, with approximate half-lives ($t_{1/2}$) of 1 hour, 30 minutes, and 20 minutes, respectively.

One pathway for metabolism of NMPs is dephosphorylation into nucleosides. To assess whether dephosphorylation was contributing to NMP degradation, stability assessments were repeated with the addition of inexpensive phosphatase inhibitors. Increased concentrations of phosphate ($PO_4$, 150 mM), as well as the structural mimic orthovandate ($VO_4$, 10 mM) were pre-incubated with lysates before hNMP addition. Increasing phosphate concentration stabilized hUMP ($t_{1/2} \approx 60$ minutes), while minimally affecting hCMP and hGMP (FIGS. 9A-9D, dashed lines). In contrast, orthovanadate stabilized hCMP ($t_{1/2} \gg 60$ minutes), hUMP ($t_{1/2} \approx 60$ minutes), and hGMP ($t_{1/2} \approx 45$ minutes) (FIGS. 9A-9D, dotted lines). Taken together, these stability assessments define an overall NMP degradation rate of 13 mM/hr in lysates, with 70% of exogenously-added NMPs present after 15 minutes. Even in the absence of phosphatase inhibitors, the relatively low rate of hNMP consumption (13 mM/hr) compared to the rate of RNase R-dependent depolymerization (>200 mM/hr), suggested that NMPs released from RNA should be available for polymerization into dsRNA.

Development of Heat Inactivation

Figure 10:
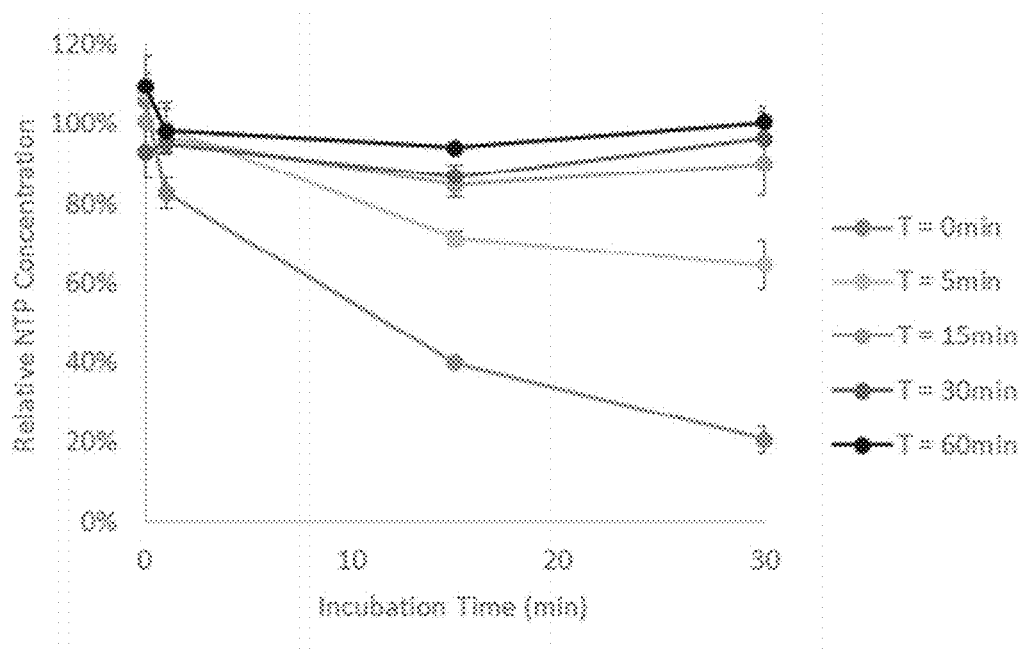
FIG. 10 is a graph demonstrating the effect of heat inactivation on the stability of exogenous NTPs in lysates. Lysates were pre-incubated at 70° C. before the temperature was lowered to 37° C. and an equimolar mixture of NTPs (ATP, CTP, UTP, and GTP) was added. Pre-incubation times are listed in the legend at right. Control lysates (not subject to heat inactivation) rapidly consumed NTPs (T=0 min). Increasing pre-incubation time stabilized NTPs, with 15 minutes at 70° C. eliminating NTPase activity (T=15 min).

To stabilize NMPs, as well as NDPs, NTPs, and dsRNA, a heat inactivation protocol was developed. The objective was to identify the lowest temperature and shortest incubation time that would eliminate nucleotide and RNA degradation activities in lysates. To assess the efficacy of heat inactivation, NTP consumption rates (at 37° C.) were compared across heat-inactivated lysates by LC-MS, where the time and temperature of heat inactivation was varied. Before heat inactivation, lysates consumed NTPs at approximately 120 mM/hr (FIG. 10). Temperatures below 70° C. did not affect NTPase activity, while incubation at 70° C. produced a time-dependent decrease in NTPase activity. Complete inhibition of NTPase activity occurred after a 15 minute incubation at 70° C. (FIG. 10).

Figure 11A:
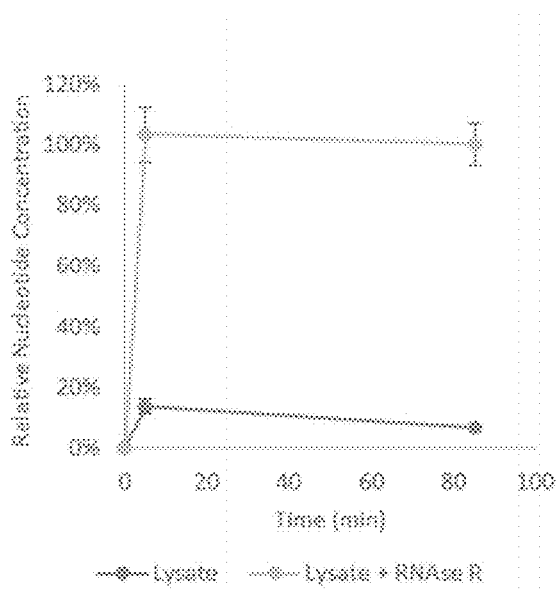
FIGS. 11A-11B are graphs demonstrating the effect of heat inactivation on the stability of NMPs and dsRNA in lysates.

Next, these conditions were evaluated for their ability to stabilize NMPs and dsRNA in lysates. To evaluate the effects of heat inactivation on NMP degradation, lysates were treated with exogenous RNase R to release RNA, then subjected to heat inactivation at 70° C. Post-inactivation, the temperature was lowered to 37° C., and the reaction incubated for an additional 60 minutes. As shown in FIG. 11A, treatment with RNase R for 5 minutes rapidly depolymerized RNA. After heat inactivation and incubation at 37° C., NMP concentrations were unchanged, suggesting that the chosen heat-inactivation conditions rendered NMPs stable.

Figure 11B:
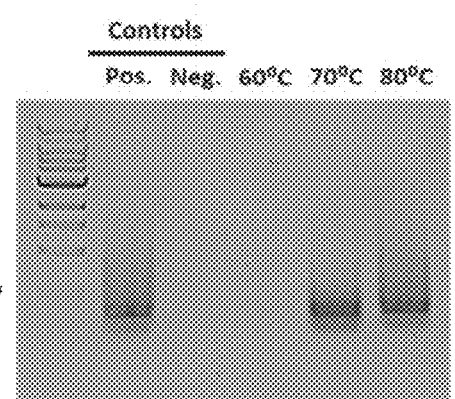

Finally, these conditions were evaluated for their ability to stabilize the reactants and products of an in vitro transcription reaction (including NTPs and dsRNA) in lysates. First, lysates were pre-incubated at elevated temperature for 15 minutes. Then, the temperature was lowered to 37° C. and transcription reactants (including exogenous NTPs, DNA template, and purified T7 RNA polymerase) were added. As shown in FIG. 11B, transcription reactions in lysates that were heat inactivated at ≥70° C. yielded RNA products qualitatively similar to the positive control reaction (performed in buffer). No RNA product was apparent in the reaction performed at 60° C.

Taken together, these results suggest that a 70° C. incubation for 15 minutes is sufficient to stabilize NMPs, NTPs, and dsRNA in cell-free reactions.

Selection and Evaluation of Thermostable Kinases

After heat-inactivation, a series of kinase activities are required to sequentially phosphorylate 5'-NMPs liberated from RNA to NTPs that can be polymerized to form dsRNA. These kinases, which use high-energy phosphate groups from ATP to phosphorylate NMPs and NDPs, must be sufficiently thermostable to remain active following high-temperature incubation, as well as sufficiently active to produce NTPs at high rates (21 mM/hr NTPs for 1 g dsRNA/L/hr). Enzymes from thermophilic organisms were chosen for evaluation (Table 9) based on literature reports of successful expression in *E. coli* and biochemical characterization of the recombinant enzymes.

TABLE 9

Origins of thermostable kinases tested for each class of activity.

| Enzyme class | Organism | Prefix |
|---|---|---|
| NMP kinase | Escherichia coli | Ec |
| | Thermus thermophilus | Tth |
| | Pyrococcus furiosus | Pf |
| | Thermosynechococcus elongatus | Te |
| | Thermotoga maritima | Tm |
| NDP kinase | Escherichia coli | Ec |
| | Thermus thermophilus | Tth |
| | Aquifex aeolicus | Aa |
| Polyphosphate kinase | Escherichia coli | Ec |
| | Thermus thermophilus | Tth |
| | Thermosynechococcus elongatus | Te |

To evaluate the suitability of these enzymes for cell-free production of dsRNA, enzymes were cloned into an *E. coli* protein expression vector with an N-terminal hexahistidine tag, overexpressed, and purified using immobilized metal affinity chromatography (IMAC). Activities of the purified enzymes were first quantified using luciferase-coupled assays, where the consumption of ATP served as a proxy for NMP and NDP phosphorylation. Assays were performed at a range of incubation temperatures to determine the optimal reaction temperature for each enzyme.

Figure 12:
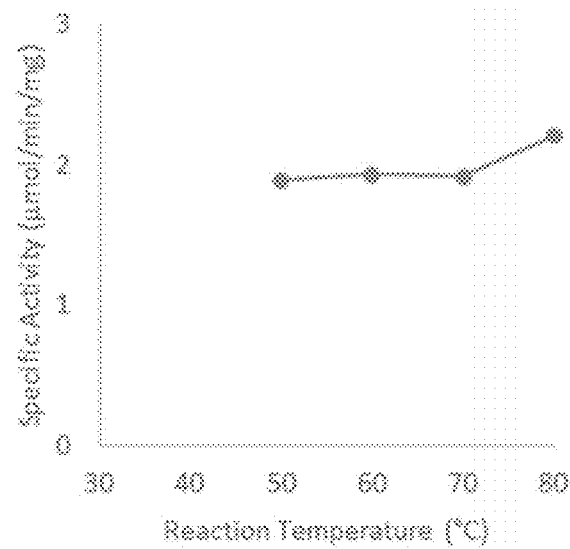
FIG. 12 is a graph demonstrating temperature-dependent activity of UMP kinase from *P. furiosus* (PfPyrH), quantified by luciferase assay for ATP consumption. The specific activity of purified PfPyrH was largely insensitive to incubation temperature.

Expression of UMP kinases (encoded by the pyrH gene) from *T. thermophilus* and *E. coli* yielded insoluble protein under the tested induction and purification conditions. Purified PyrH from *P. furiosus* exhibited a specific activity of approximately 2 µmol/min/mg protein that was largely temperature-independent (FIG. 12). Based on this specific activity, a high-density cell lysate (90 g dcw/L) expressing PfPyrH at 1% total protein would, in the presence of excess ATP, phosphorylate UMP at rates in excess of 50 mM/hr (Table 10). As dsRNA production at 1 g/L/hr requires approximately 5.25 mM/hr of UMP kinase activity. PfPyrH was chosen for further evaluation. Table 10 shows predicted PyrH rates in high-density (90 g dcw/L) lysates, assuming PfPyrH constitutes 1% of total lysate protein.

TABLE 10

Predicted PyrH reaction rates

| Temperature (° C.) | Predicted Rate (mM/hr) |
|---|---|
| 50 | 51.0 |
| 60 | 52.4 |
| 70 | 51.8 |
| 80 | 59.7 |

Figure 13:
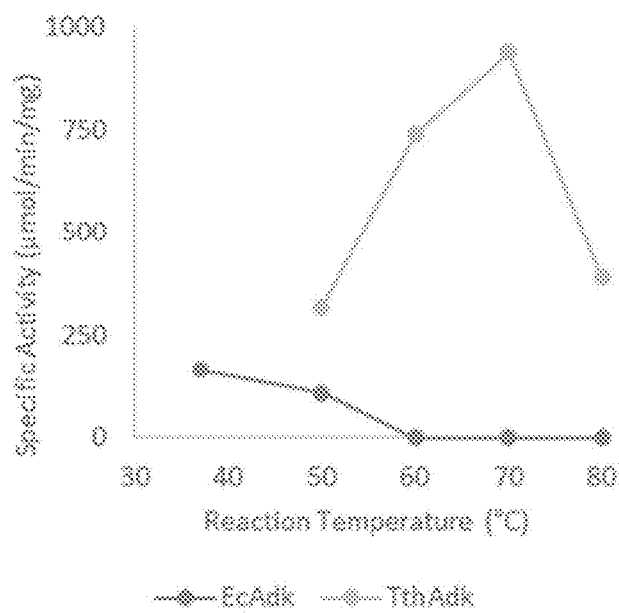
FIG. 13 is a graph demonstrating temperature-dependent activity of AMP kinase from *T. thermophilus* (TthAdk) compared to Adk from *E. coli* (EcAdk), measured via luciferase. Purified EcAdk was active at temperatures below 60° C. TthAdk had higher specific activity, with a maximum at 70° C.

Expression of AMP kinases (encoded by the adk gene) from *E. coli* and *T. thermophilus* yielded soluble recombinant protein, while the *Thermosynechococcus* enzyme was insoluble under the tested expression and purification conditions. The purified *E. coli* enzyme was active at 37° C. and 50° C., but exhibited no detectable activity at higher temperatures (FIG. 13). The *T. thermophilus* enzyme exhibited higher specific activity than the *E. coli* enzyme at all tested temperatures, with an optimal activity of nearly 1 mM/min per mg enzyme at 70° C. This activity, when the enzyme is expressed at 0.01% of total protein in a high-density lysate, translates to an expected rate in excess of 250 mM/hr of AMP phosphorylation in lysates (Table 11). As approximately 5.25 mM/hr of AMP kinase activity is required to synthesize 1 g/L/hr dsRNA, TthAdk was chosen for further study. Table 11 shows predicted Adk reaction rates in high-density (90 g dcw/L) lysates, assuming TthAdk constitutes 0.01% of total lysate protein.

TABLE 11

Predicted Adk reaction rates

| Temperature (° C.) | Predicted Rate (mM/hr) |
|---|---|
| 37 | n.d. |
| 50 | 86.4 |
| 60 | 199.5 |
| 70 | 253.8 |
| 80 | 106.1 |

Figure 14:
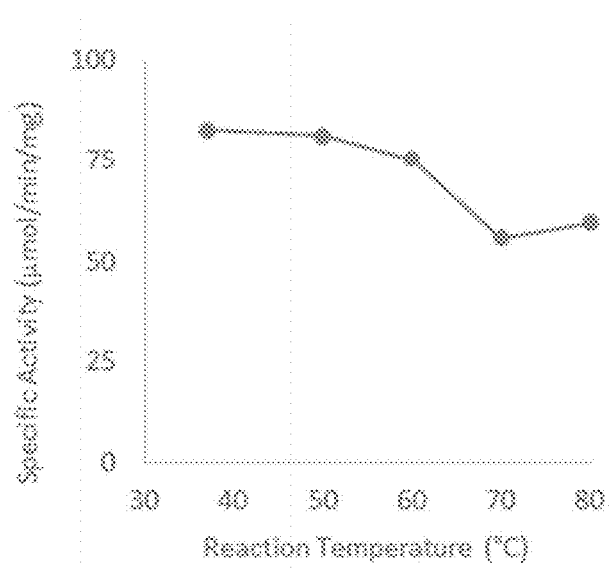
FIG. 14 is a graph demonstrating temperature-dependent activity of CMP kinase from *T. thermophilus* (TthCmk), measured via luciferase. Purified TthCmk was relatively insensitive to temperature, with high activity from 37-80° C.
Figure 15:
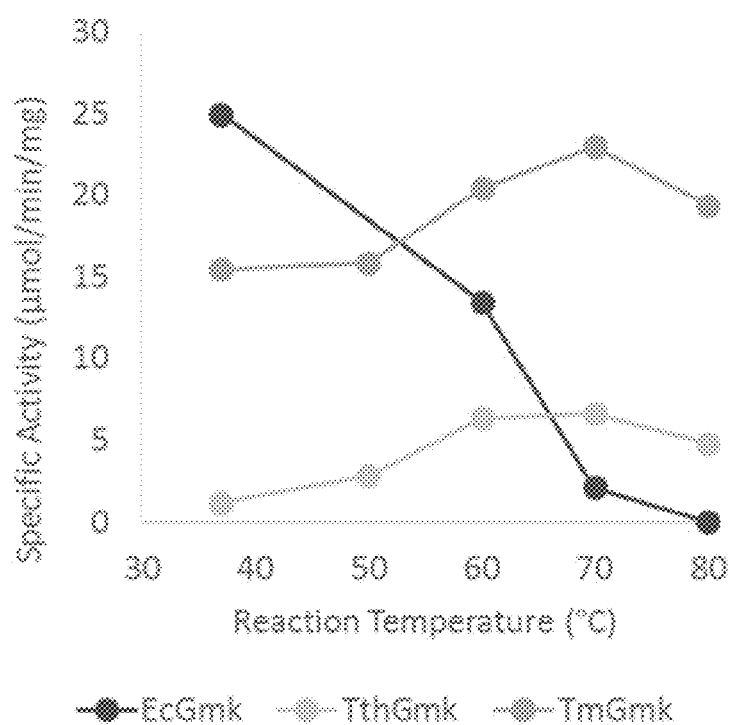
FIG. 15 is a graph demonstrating temperature-dependent activity of GMP kinases from *E. coli* (EcGmk), *T. thermophilus* (TthGmk), and *T. maritima* (TmGmk), measured via luciferase. Purified EcGmk (dark gray) was more active at lower temperatures, while TthGmk (light gray) and TmGmk (medium gray) were most active at 70° C.

Expression of CMP kinases (encoded by the cmk gene) from *E. coli* and *P. furiosus* yielded insoluble protein, while expression of the *T. thermophilus* enzyme yielded soluble protein under the tested conditions. *T. thermophilus* CMP kinase exhibited activity largely independent of temperature, although enzyme activity decreased slightly at temperatures above 60° C. (FIG. 14). Based on these results, expression of TthCmk in high-density lysates at 0.02% of total protein would yield CMP kinase activities of 30-45 mM/hr (depending on temperature, Table 12), well in excess of the 5.25 mM/hr target. Therefore, TthCmk was chosen for further evaluation. Table 12 shows predicted Cmk reaction rates in high-density (90 g dcw/L) lysates, assuming TthCmk constitutes 0.02% of total lysate protein.

TABLE 12

Predicted Cmk reaction rates

| Temperature (° C.) | Predicted Rate (mM/hr) |
|---|---|
| 37 | 44.8 |
| 50 | 44.0 |
| 60 | 40.8 |
| 70 | 30.2 |
| 80 | 32.2 |

In contrast to the tested CMP kinases, expression of GMP kinases from *E. coli*, *T. thermophilus*, and *T. maritima* yielded soluble recombinant protein. The *E. coli* enzyme had the highest tested specific activity at 37° C., but was less active at higher temperatures (FIG. 14). While the *T. thermophilus* and *T. maritima* enzymes both exhibited optimal activity at higher temperatures, the *T. maritima* enzyme was more active at all tested temperatures. Based on the measured specific activities of TmGmk, expression in a high-density cell lysate at 0.1% of total protein would yield an expected rate in excess of 60 mM/hr at 70° C. in the presence of excess ATP, compared to a target rate of 5.25 mM/hr (Table 13). Therefore, TmGmk was chosen for further evaluation. Table 13 shows predicted Gmk reaction rates in high-density (90 g dcw/L) lysates, assuming TmGmk constitutes 0.1% of total lysate protein.

TABLE 13

Predicted Gmk reaction rates

| Temperature (° C.) | Predicted Rate (mM/hr) |
|---|---|
| 37 | 41.8 |
| 50 | 42.8 |
| 60 | 55.2 |

TABLE 13-continued

Predicted Gmk reaction rates

| Temperature (° C.) | Predicted Rate (mM/hr) |
|---|---|
| 70 | 62.0 |
| 80 | 52.4 |

Figure 16:
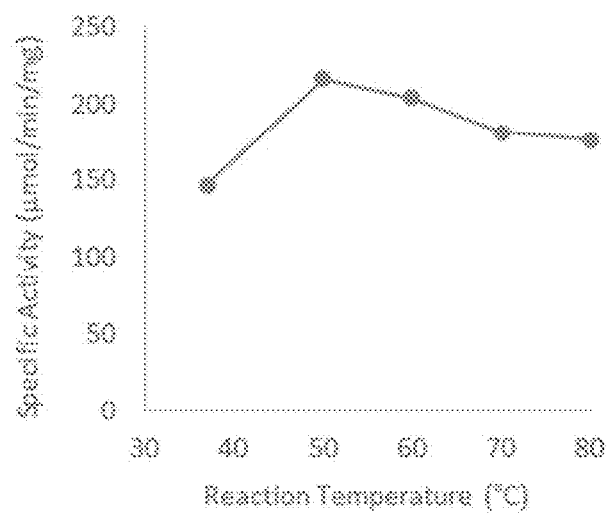
FIG. 16 is a graph of data demonstrating activity of purified NDP kinase from *A. aeolicus* (AaNdk), measured via luciferase. Purified AaNdk was highly active from 37-80° C., using ATP and GDP as substrates, with optimal activity at 50° C.

Unlike the NMP kinases, which are largely specific for a single substrate, NDP kinase phosphorylates ADP, CDP, UDP, and GDP. To compare NDP kinases, enzymes from the thermophiles *T. thermophilus* and *A. aeolicus* were cloned and expressed in *E. coli*. While the *T. thermophilus* enzyme was insoluble under the tested conditions, expression of the *A. aeolicus* enzyme yielded soluble protein. Activity measurements in a luciferase assay using ATP and GDP as substrates revealed that AaNdk is highly active across a broad range of temperatures, with a temperature optimum of 50° C. (FIG. 16). Comparison across substrates revealed specific activities in excess of 100 µmol/min/mg at 50° C. for each nucleotide, confirming that AaNdk could phosphorylate multiple NDP substrates (Table 14). Based on these measurements, expression of AaNdk in high density lysates at 0.01% total protein translates to UDP kinase rates well in excess of 60 mM/hr. Given that 21 mM/hr of NDP kinase activity is required to support 1 g/L/hr dsRNA synthesis, AaNdk was chosen for further evaluation. Table 14 shows that at 50° C., AaNdk is highly active with CDP, UDP, and GDP substrates.

TABLE 14

AaNdk specific activity by substrate.

| Substrate | Specific Activity (µmol/min/mg) |
|---|---|
| CDP | 259.6 |
| UDP | 110.4 |
| GDP | 217 |

Figure 17:
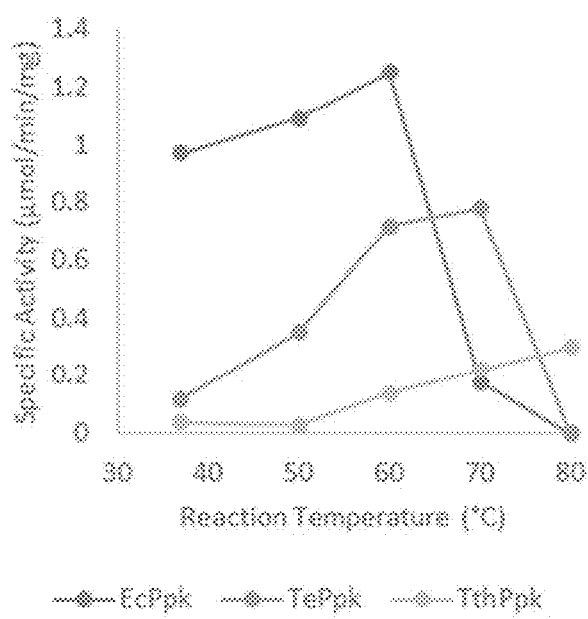
FIG. 17 is a graph demonstrating activity of purified polyphosphate kinase 1 (PPK1) enzymes from *E. coli* (EcPpk), *Thermosynechococcus elongatus* (TePpk), and *Thermus thermophilus* (TthPpk) measured via luciferase. EcPpk was most active at temperatures≤60° C., while TePpk was optimally active at 70° C. TthPpk exhibited relatively low activity.

Polyphosphate kinase (Ppk) reversibly transfers high-energy phosphate groups between polymeric phosphate chains and adenosine nucleotides. Multiple Ppk enzymes, belonging to the Type I family of polyphosphate kinases, were evaluated for activity, including enzymes from *E. coli* as well as the thermophilic organisms *T. thermophilus* and *Thermosynechococcus elongatus*. These enzymes were selected for testing as they belonged to the well-characterized Type I family or had previously been shown to be active. Expression and purification of Ppk enzymes yielded soluble protein, which was then tested for activity in a luciferase assay system using ADP and sodium hexametaphosphate as substrates. As shown in FIG. 17, the specific activity of all tested Ppk enzymes was low relative to other kinase activities. The *E. coli* Ppk had the highest specific activity at lower temperatures (up to 60° C.), while the *Thermosynechococcus* enzyme had the highest activity at 70° C. Additionally, incubation of the *E. coli* enzyme under heat inactivation conditions (70° C. for 15 minutes) led to irreversible inactivation (not shown). Based on the specific activity of the *Thermosynechococcus* enzyme, expression in a high density lysate at 2% of total protein would lead to an expected rate of 42 mM/hr at 70° C. (Table 15), matching the required ATP production rate to support 1 g/L/hr dsRNA synthesis. However, cell-free dsRNA synthesis at lower temperatures (e.g., 50° C.) would require higher expression of TePpk (in excess of 4% total protein). Table 15 shows predicted Ppk reaction rates in high-density (90 g dcw/L) lysates, assuming TePpk constitutes 2% of total lysate protein.

TABLE 15

Predicted PPK1 reaction rates

| Temperature (° C.) | Predicted Rate (mM/hr) |
|---|---|
| 37 | 6.5 |
| 50 | 18.9 |
| 60 | 38.9 |
| 70 | 42.1 |
| 80 | 0 |

After evaluating each enzymatic activity in a purified system, enzymes were tested for activity in heat-inactivated lysates. Lysates expressing individual kinases were pre-incubated at 70° C. for 15 minutes before substrates were added. As in the purified reactions, ATP consumption (for NMP and NDP kinases) or ATP production (for polyphosphate kinase) were quantified using a luciferase assay kit. As shown in Table 16 below, rates of NMP and NDP phosphorylation were well in excess of targets.

TABLE 16

Kinase activities in heat-inactivated lysates

| Enzyme | Reaction | Rate (mM/hr) | Target (mM/hr) |
|---|---|---|---|
| PfPyrH | UMP + ATP ⇌ UDP + ADP + $P_i$ | 151 | 5.25 |
| TthAdk | AMP + ATP ⇌ 2 ADP + 2 $P_i$ | 199 | 5.25 |
| TthCmk | CMP + ATP ⇌ CDP + ADP + $P_i$ | 183 | 5.25 |
| PfGmk | GMP + ATP ⇌ GDP + ADP + $P_i$ | 168 | 5.25 |
| AaNdk | NDP + ATP ⇌ NTP + ADP + $P_i$ | 163 | 21 |
| TePpk | ADP + Poly-$P_n$ ⇌ ATP + Poly-$P_{n-1}$ | 2.7 | 42 |

After confirming that individual kinases were sufficiently active in lysates (with the exception of Ppk), kinases were evaluated in a multi-enzyme system for their ability to convert NMPs to NTPs. In these studies, equal volumes of lysates expressing individual kinases (5) were combined, heat-inactivated, then assayed for ATP-dependent production of NTPs from an equimolar mix of NMPs by LC-MS. As shown in Table 17, overall NTP production rates exceeded 24 mM/hr for UTP, CTP, and GTP, suggesting that a simple mixture of lysates, without any optimization of reaction conditions, could provide NTPs at sufficient rates to support synthesis of 1 g/L/hr dsRNA, in the presence of adequate ATP.

TABLE 17

Production of NTPs in a heat-inactivated 1:1 mixture of lysates expressing individual kinase activities, using an equimolar mixture of NMPs as substrates and ATP as a high-energy phosphate donor

| Pathway | Rate (mM/hr) |
|---|---|
| UMP → UTP | 3.24 |
| CMP → CTP | 9.24 |
| GMP → GTP | 11.8 |

TABLE 17-continued

Production of NTPs in a heat-inactivated 1:1 mixture of lysates expressing individual kinase activities, using an equimolar mixture of NMPs as substrates and ATP as a high-energy phosphate donor

| Pathway | Rate (mM/hr) |
| --- | --- |
| AMP → ATP | n.d. |
| NMPs → NTPs | >24.3 |

RNA Polymerase Downselection

After depolymerization of RNA into NMPs and phosphorylation of NMPs to their corresponding NTPs, a RNA polymerase is required to convert NTPs into the dsRNA product. RNA polymerase from the bacteriophage T7 is an attractive enzyme for use in a recombinant system for several reasons. T7 RNA polymerase includes a single subunit (unlike many RNA polymerases from Bacteria and Eukarya) and has been extensively characterized by biochemical and molecular biology studies. Additionally, multiple T7 RNA polymerase mutants have been described that confer improved thermostability (see Table 18).

TABLE 18

List of T7 RNA polymerases evaluated for activity and thermostability

| Enzyme Name | Source | Rationale |
| --- | --- | --- |
| MegaScript T7 | Invitrogen | Component of high-yield transcription kit |
| T7 RNA Polymerase | New England Biolabs | Control |
| ThermoT7 RNA Polymerase «TT7» | Toyobo Life Sciences JP4399684 (Toyobo) | Claimed activity at 50° C. |
| T7 RNA Polymerase (LVI) | EP2377928 (Roche) | Claimed activity at 50° C. |
| T7 RNA Polymerase (PPIY) | EP1261696 (bioMerieux) | Claimed activity at 50° C. |
| T7 RNA Polymerase (LPPVIIY) | Combination of LVI & PPIY | Mutations potentially synergistic |

Figure 18:
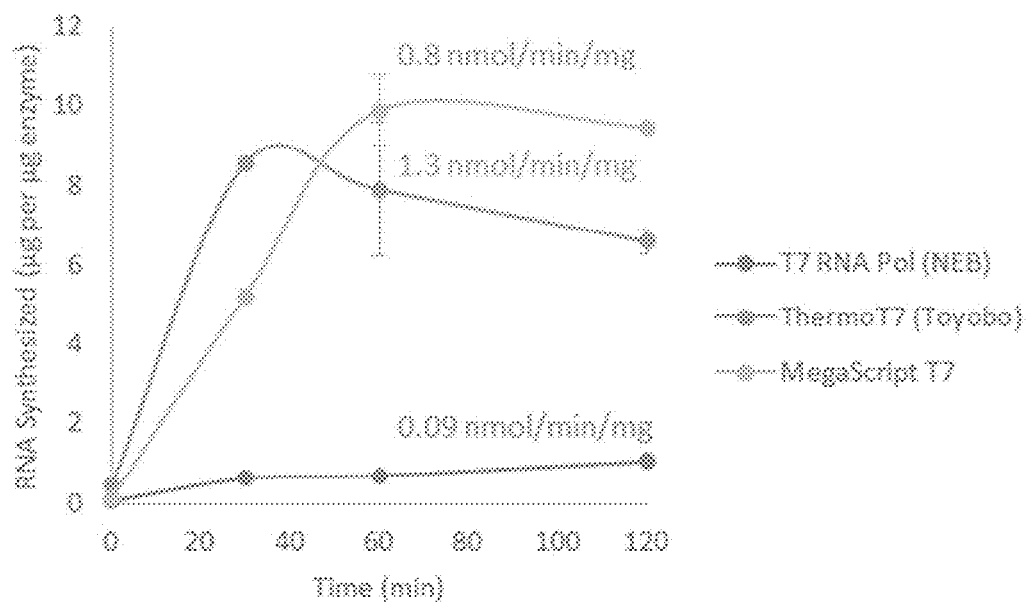
FIG. 18 is a graph demonstrating activity of commercially-available T7 RNA polymerases in buffer using conditions recommended by their respective manufacturers at 37° C. ThermoT7 and MegaScript polymerases exhibited higher specific activity than the NEB polymerase under the tested conditions with duplex DNA template (e.g.

First, the activities of commercially-available T7 RNA polymerases were evaluated using duplex DNA template (e.g. FIG. 3B) and a 37° C. reaction temperature. The production of RNA was quantified over time using the Quant-iT RNA Kit (Broad Range) (Thermo Fisher Scientific). Under conditions recommended by each manufacturer, the ThermoT7 and MegaScript enzymes were highly active, while the NEB enzyme displayed significantly lower activity (FIG. 18).

Next, the LVI mutant of T7 RNA polymerase was cloned with an N-terminal hexahistidine tag, expressed in E. coli, and purified using IMAC.

Figure 19:
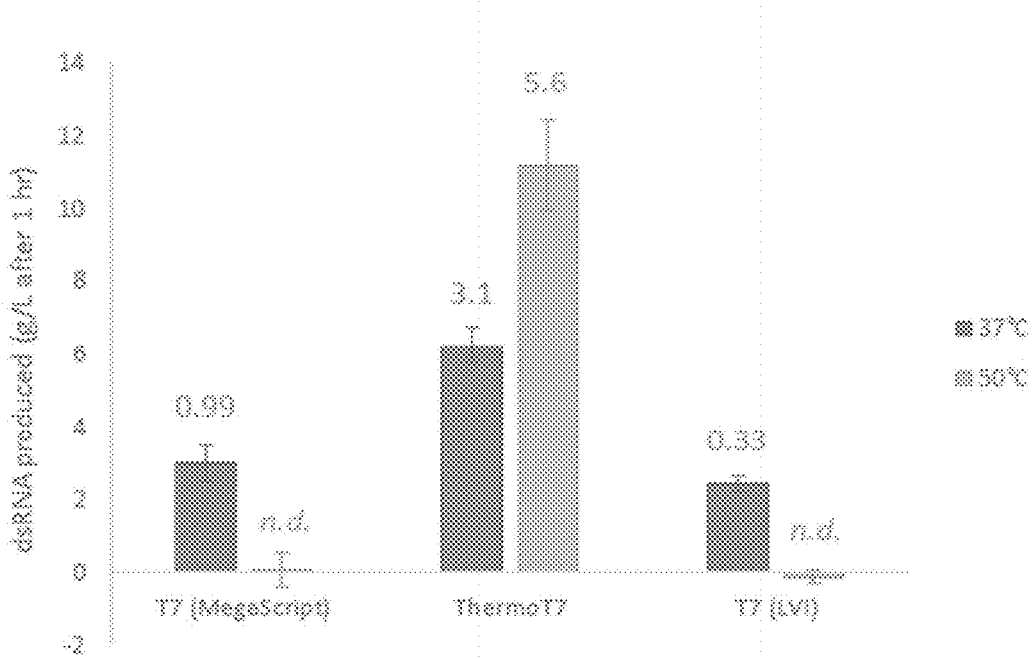
FIG. 19 is a graph comparing T7 RNA polymerase activities in dilute lysates at 37° C. and 50° C. under standardized reaction conditions with duplex DNA template. At 37° C., ThermoT7 exhibited the highest specific activity. At 50° C., only ThermoT7 had detectable activity, producing over 10 g/L/hr dsRNA.

Next, activities of the MegaScript and ThermoT7 polymerases were tested alongside the LVI mutant polymerase in dilute heat-inactivated lysates (35% final lysate concentration) under standardized reaction conditions (FIG. 19). As in a purified system, ThermoT7 exhibits higher specific activity at 37° C. (3.1 nmol RNA/min/mg protein) than the MegaScript enzyme. The LVI mutant had the lowest specific activity (0.33 nmol/min/mg) of the three enzymes tested. When tested under otherwise identical conditions at 50° C., neither the MegaScript enzyme nor the LVI mutant exhibited any detectable activity. In contrast, activity of ThermoT7 was higher than at 37° C. With approximately 4% of total protein in the assay as ThermoT7 polymerase, RNA synthesis rates exceeded 11 g/L/hr at 50° C. with duplex DNA template and ThermoT7 polymerase (FIG. 19). ThermoT7 was then selected for further characterization.

Figure 20:
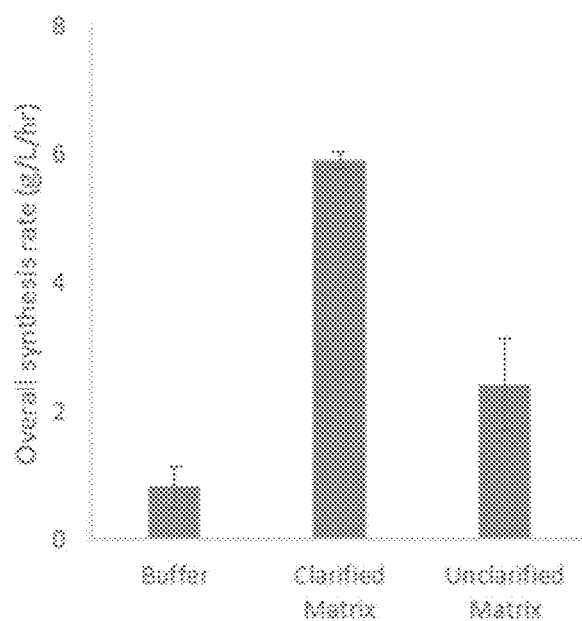
FIG. 20 is a graph demonstrating activity of ThermoT7 activities in buffer and high-density heat-inactivated lysates. ThermoT7 activity was highest in lysates clarified by centrifugation after heat-inactivation. Omitting the clarification step led to a 60% decrease in activity, although polymerase activity in unclarified matrix was greater than in buffer alone.

After confirming the activity of ThermoT7 at 50° C. in dilute heat-inactivated lysate, the activity of ThermoT7 was investigated under conditions representative of cell-free dsRNA production at scale. In addition to increased concentrations of lysate, reactions at scale may include precipitated lysate components (e.g., protein) that arise from the heat inactivation process. To assess the performance of ThermoT7 under these conditions, RNA polymerization was quantified in heat-inactivated high-density lysates (68% final lysate concentration) with and without clarification to remove precipitated proteins after heat inactivation (FIG. 20). RNA synthesis rates were significantly higher in matrix than in buffer, with the highest rates occurring in heat-inactivated matrix that had been clarified by centrifugation. In unclarified reactions, overall RNA synthesis rates (over a 2-hour reaction) were in excess of 2 g/L/hr with 1.4% of total protein in the assay as ThermoT7 polymerase.

Figure 21:
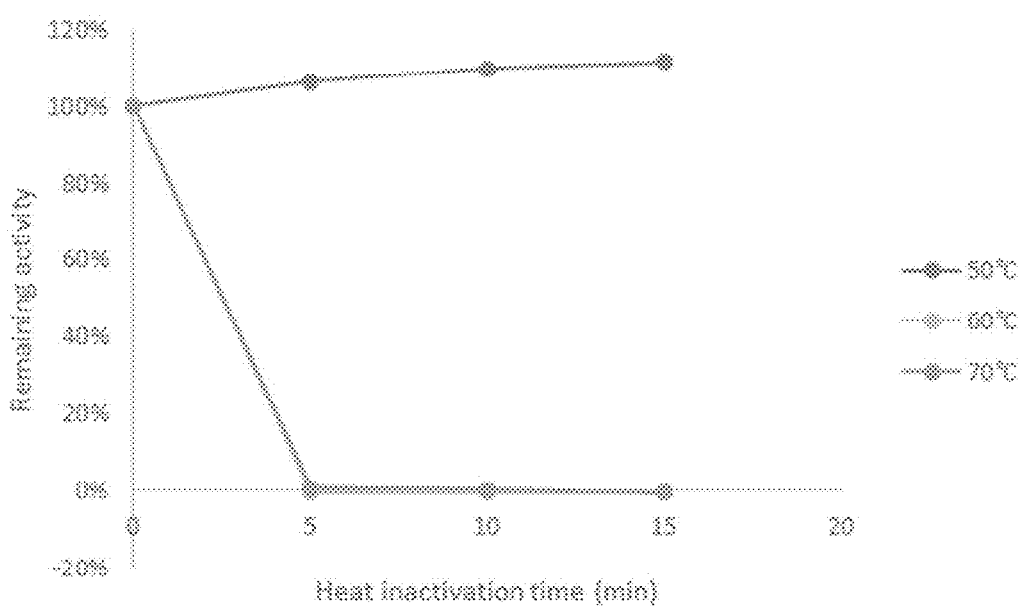
FIG. 21 is a graph demonstrating tolerance of ThermoT7 to elevated temperatures. Pre-incubating ThermoT7 at 50° C. had no effect on subsequent polymerase activity assayed at 37° C. Pre-incubating at 60° C. and 70° C. led to rapid, irreversible inhibition of enzyme function.

Finally, the thermostability of ThermoT7 was tested at higher temperatures to evaluate compatibility with the heat inactivation conditions established earlier in this program. In these studies, ThermoT7 enzyme was pre-incubated at elevated temperature (50-70° C.) for varying lengths of time (0-15 minutes), and the remaining activity quantified at 37° C. As shown in FIG. 21, incubation at 50° C. is well-tolerated by the enzyme, but higher temperatures lead to rapid irreversible inactivation of polymerase activity. Therefore, in these experiments, this particular Thermo T7 was not compatible with heat-inactivation at 50-70° C. Thus, in some instances, purified ThermoT7 enzyme may be added to cell-free reactions following a thermal inactivation, or an alternate T7 RNA polymerase mutant may be used, having sufficient half-life at 70° C., for example.

Materials and Methods

Nucleotide Analysis

Analysis of nucleotide monophosphates (AMP, CMP. UMP, and GMP) was performed by liquid chromatography coupled with mass spectrometry (LC-MS). Samples were separated using an Agilent 1100 series HPLC equipped with a ZIC-cHILIC column (2.1×20 mm, 3 μm i.d.) (Merck) at room temperature with a flow rate of 0.5 mL/min and a 2 μL injection volume. Mobile phases consisted of 20 mM ammonium acetate (A) and 20 mM ammonium acetate in 90% acetonitrile (B). The separation method consisted of a gradient from 15-50% (B) for 3.5 minutes, followed by 50% (B) for 1.5 minutes, then 15% B for 3 minutes. Quantification was performed on an ABSciex API 3200 mass spectrometer using electrospray ionization (capillary voltage: −3000V, temperature: 600° C., desolvation gas: 20 psi) in multiple reaction monitoring (MRM) mode. Analysis of nucleotide monophosphate, diphosphate, and triphosphate species (NMPs, NDPs, and NTPs) used the method described above with the following separation gradient: 15% B to 50% B for 3.5 minutes, followed by 50% B for 2.5 min, then 15% B for 4 minutes. Peak areas were compared to standard curves consisting of purified compounds (Sigma-Aldrich). For analysis of samples in lysates, standard curves were prepared in lysate backgrounds that had been acid-quenched, clarified, pH-neutralized, and filtered as in the sample preparation steps described below.

Analysis of 2'-, 3'-, and 5'-NMPs was performed by liquid chromatography using an ACQUITY H-Class UPLC (Waters) equipped with an ACQUITY CSH fluoro-phenyl column (2.1×150 mm, 1.7 μm i.d.) (Waters) at 40° C. with a flow rate of 0.5 mL/min and a 0.5 μL injection volume. Mobile phases consisted of 10 mM ammonium acetate in 0.2% formic acid (A) and 10 mM ammonium acetate in 95% acetonitrile, 0.2% formic acid (B). The separation method consisted of 1% B for 2.8 minutes, followed by a gradient from 1%-30% B for 2.2 minutes, followed by 100% B for 7 minutes, then 1% B for 3 minutes. Quantification was performed using an ACQUITY UPLC PDA (Waters) at 260, 254, and 210 nm. Peak areas were compared to standard curves consisting of purified compounds (purchased from Sigma-Aldrich except for 2' and 3' CMP, UMP, and GMP which were purchased from Biolog Life Science Institute). For analysis of samples in lysates, standard curves were prepared in lysate backgrounds that had been acid-quenched, clarified, pH-neutralized, and filtered as in the sample preparation steps described below.

Extraction and Purification of *E. coli* RNA

RNA was extracted and purified from high-density *E. coli* lysates (protein concentration: 40-50 mg/mL) according to established protocols (Mohanty, B. K., Giladi, H., Maples, V. F., & Kushner, S. R. (2008). Analysis of RNA decay, processing, and polyadenylation in *Escherichia coli* and other prokaryotes. Methods in enzymology, 447, 3-29). For every 400 μL of frozen *E. coli* lysate, 67 μL of 20 mM acetic acid was added to reduce RNase activity. Samples were thawed in a bead bath at 37° C. Immediately upon thawing, 400 μL of a 10% (w/v) solution of trimethyl(tetradecyl)ammonium bromide (Sigma-Aldrich) was added. The resulting suspensions were then clarified by centrifugation at 10,000×g in a microcentrifuge at 4° C., and the supernatant removed. Pellets were resuspended in 1 mL of a 2M solution of lithium chloride (Sigma-Aldrich) in 35% ethanol. The suspensions were incubated at room temperature for 5 minutes, then clarified by centrifugation at 15,000×g for 6 minutes at 4° C. and the supernatants removed. Pellets were then resuspended in 1 mL of a 2M solution of lithium chloride in water, and incubated at room temperature for 2 minutes before clarification at 15,000×g for 6 minutes. Supernatants were then removed and the remaining pellets washed by resuspending in 70% ethanol and centrifuging at maximum speed (21,000×g) for 5 minutes at 4° C. Supernatants were then removed and the pellets were air-dried for 15 minutes at room temperature. Pellets were then resuspended in 200 μL nuclease-free water, and incubated overnight at 4° C. to solubilize RNA. RNA solutions were clarified by centrifugation (maximum speed for 5 minutes at 4° C.) and supernatants containing soluble RNA were transferred to sterile RNase-free tubes and stored at −20° C.

Nuclease Downselection

Nucleases were obtained from commercial sources as follows: Benzonase and Nuclease P1 were obtained from Sigma-Aldrich, RNase R, Terminator exonuclease, and RNase III were obtained from Epicentre, RNase A was obtained from Thermo Fisher, and Exonuclease T was obtained from New England BioLabs. For screening assays, 1 μL of each enzyme solution was added to 100 μL of 2× assay buffer (100 mM potassium phosphate pH 7.4, 10 mM magnesium chloride, 1 mM zinc chloride), then combined with an equal volume of 1 mM RNA solution (~340 ng/μL) at time t=0 and mixed well. Reactions were incubated at 37° C. and periodically sampled by transferring 20 μL to acid quench solution (180 μL of 0.2M sulfuric acid) on ice. After completion of the time course, quenched samples were clarified by centrifugation at 3,000×g for 5 minutes at 4° C. 170 μL of supernatant from each sample was then transferred to a UV-transparent 96-well half area plate (Corning) and acid-soluble nucleotides were quantified by absorbance at 260 nm using a microplate reader and an extinction coefficient of 10665 $M^{-1}$ $cm^{-1}$, estimated by averaging individual extinction coefficients for each mononucleotide. For subsequent analysis by LC-MS, 45 μL clarified supernatant was pH-neutralized with 5 μL of 2.5 M potassium hydroxide. The total nucleotide pool (i.e. 100% depolymerization) was determined by alkaline hydrolysis of RNA: RNA was combined with an equal volume of 0.2M potassium hydroxide, then heated to 99° C. for 20 minutes. Alkaline-hydrolyzed samples were then quenched and analyzed as described above.

Protein Expression and Purification

Recombinant proteins were cloned from synthetic DNA encoding the relevant gene along with a hexahistidine tag into pETDuet-1 (Novagen). Plasmids were transformed into *E. coli* T7Express (New England Biolabs), then grown in 1 L cultures using ZYM-505 media (Studier, F. W. (2005). Protein production by auto-induction in high-density shaking cultures. Protein expression and purification, 41(1), 207-234) supplemented with 50 μg/mL carbenicillin. Expression was induced at $A_{600}$=0.6. For RNase R and kinases, expression was induced with 0.1 mM IPTG, the temperature lowered to 16*C, and the culture grown for 24 hours at 16° C. For T7 RNA polymerase, expression was induced with 0.8 mM IPTG and the culture grown for 3 hours at 37° C. Biomass was harvested by centrifugation and the supernatant decanted before storing the cell pellets at −80° C. Cell pellets were thawed and lysed by resuspension into 4 volumes B-PER Complete (Thermo Fisher Scientific) supplemented with Benzonase (0.04 μL/mL) and incubation with gentle agitation for 15 minutes at room temperature. Lysates were then clarified by centrifugation at 16,000×g for 1 hour at 4° C. Proteins were purified by immobilized metal affinity chromatography using His GraviTrap columns (GE Healthcare) or HisTrap HP columns connected to an AKTAPrime Plus FPLC system (GE Healthcare). For both purification methods, columns were equilibrated in Equilibration/Wash buffer (50 mM phosphate buffer pH 7.4, 500 mM NaCl, 20 mM imidazole), loaded with lysate, and then washed with 30 column volumes Equilibration/Wash Buffer. Proteins were eluted with Elution Buffer (50 mM phosphate buffer pH 7.4, 500 mM NaCl, 500 mM imidazole). For purification of kinases, Equilibration/Wash and Elution buffers used 50 mM Tris-HCl pH 7.5 instead of phosphate buffer. Elution fractions were analyzed by SDS-PAGE and protein content quantified by BCA (Thermo Fisher Scientific). Fractions were then combined and buffer exchanged by dialysis into 1000 volumes 2× Storage Buffer. For RNase R, 2× Storage Buffer consisted of 2×PBS supplemented with an additional 500 mM NaCl. For T7 RNA polymerase, 2× Storage Buffer consisted of 2×PBS. For kinases, 2× Storage Buffer consisted of 100 mM Tris-HCl pH 7.0 with 100 mM NaCl. After dialysis, proteins were mixed with an equal volume of 100% glycerol (50% final concentration) and stored at −20° C.

Cell Lysate Preparation

E. coli strains GL16-170 (BL21(DE3) .t526pgi.Δedd.ΔtktB.ΔtolC_wt-7-E1.ΔmgsA*-F3.ΔappA*.Δamn*-F1.nagD(keio)::zeoR-1.ΔphoA*.t352BAA1644.ΔushA*-C4.rna::tolC-B04) and GL14-322 (BL21 (DE3).t526pgi.Δedd.ΔtktB.ΔtolC_wt-7-E.ΔmgsA*-F3.ΔappA*.Δamn*-F1.nagD(keio)::zeoR-1.ΔphoA*.t352BAA1644.ΔushA::tolC-A01) were grown in Korz media in 10 L bioreactors until the end of batch phase, then harvested by centrifugation and frozen at −80° C. Pellets were resuspended to 10% dry cell weight in 58.8 mM potassium phosphate dibasic and lysed using 2 passes through a PandaPLUS homogenizer (GEA Niro Soavi) cooled to 4° C. at 15,000 psi. Lysates were clarified by centrifugation at 16,000×g for 1 hour at 4° C. and protein content was analyzed by BCA assay (Thermo Fisher) before storage at −80° C.

Depolymerization of Lyate RNA with Exogenous RNase R

GL16-170 lysate (protein content 34.5 mg/mL) and RNase R solution (1 mg/mL in 300 mM potassium phosphate buffer pH 7.4, 200 mM KCl, 2 mM $MgCl_2$) were pre-equilibrated at 2° C. before initiating the reaction. At time t=0, 50 μL of E. coli lysate and 50 μL RNase R solution were mixed and the reaction initiated by transferring to a pre-heated 37° C. block. Reactions including deoxycholate were assembled as described above, except that lysates were premixed with 0.2 volumes of 5× sodium deoxycholate solutions in water and incubated at 2° C. for 15 minutes before initiation. After initiation, reactions were incubated at 37° C. and periodically sampled by transferring 10 μL to acid quench solution (90 μL of 0.2M sulfuric acid) on ice. After completion of the time course, quenched samples were clarified by centrifugation at 3,200×g for 10 minutes at 2° C. Depolymerization was first quantified by absorbance of acid-soluble nucleotides: 10 μL of quenched and clarified reactions was added to 160 μL of 0.2M sulfuric acid in a UV-transparent 96-well half area plate (Corning). Acid-soluble nucleotides were quantified by absorbance at 260 nm using a microplate reader (see above). Depolymerization was also quantified by UPLC analysis of 5′, 2′, and 3′ NMPs: 30 μL of each acid-quenched sample was pH-neutralized by adding 10 μL of 1M KOH, then passed through a 0.2 μm filter before UPLC analysis. The total nucleotide pool (i.e. 100% depolymerization) was determined by alkaline hydrolysis of lysate RNA: 50 μL lysate was combined with 150 μL of 0.2 M potassium hydroxide, then heated to 99° C. for 20 minutes. Alkaline-hydrolyzed samples were then quenched and analyzed as described above.

Depolymerization of RNA in Lysates with Overexpressed RNase R

E. coli strain GL16-170 was transformed with pETDuet-1 encoding the E. coli rnr gene with a C-terminal hexahistidine tag. This strain, alongside GL16-170 transformed with empty pETDuet-1, was grown in batch phase in Korz medium supplemented with 50 mg/L carbenicillin. Cultures were induced with 0.8 mM IPTG at $A_{600}$=20 and supplemented with an additional 10 g/L glucose at induction. One hour following induction, biomass was harvested by centrifugation and frozen. Lysates were prepared from frozen biomass as described above (Protein concentrations: 36.6 mg/mL for GL16-170 biomass with empty pETDuet-1; 53.2 mg/mL for GL16-170 with pETDuet-1 carrying cloned RNase R). Depolymerization in dilute lysates was assessed as described above with 50% final lysate concentration in the reaction. Depolymerization in concentrated lysates was assessed by pre-incubating 9 volumes lysate with 1 volume 10×EDTA solution for 5 minutes at 2° C. Reactions were then initiated by transferring to a preheated 37° C. block and sampling as described above.

NMP Stability Assessment

Four volumes of GL14-322 lysate (protein concentration: 50.5 mg/mL) were combined with one volume of phosphatase inhibitor solution (final concentrations of 50 mM potassium phosphate pH 7.4, 150 mM potassium phosphate pH 7.4, or 10 mM sodium orthovanadate) on ice. An equimolar solution of isotopically labeled NMPs (Adenosine-$^{13}C_{10}$, $^{15}N_5$ 5′-monophosphate, Cytidine-$^{15}N_3$-5′-monophosphate, Uridine-$^{15}N_2$-5′-monophosphate, and Guanosine-$^{15}N_5$-5′-monophosphate [Sigma-Aldrich], 25 mM each) was prepared in water. Lysates and NMPs were equilibrated to 37° C. for 10 minutes before reactions were initiated. To initiate reactions, 90 μL lysate solution was added to 10 μL NMP solution, and the reactions mixed well. Reactions were monitored by sampling at the indicated time points. During sampling, 12 μL of reaction mixture were transferred to 108 μL of 0.2M sulfuric acid on ice. Quenched reactions were then clarified by centrifugation, pH-neutralized, and filtered for LC-MS analysis as described above.

Development of Heat Inactivation

GL14-322 lysate was aliquoted into 5 microcentrifuge tubes on ice, then transferred to a heat block equilibrated at the desired heat inactivation temperature. At the indicated times, tubes were cooled on ice, then clarified by centrifugation (21,000×g for 5 minutes) and the supernatants harvested. Supernatants from heat-inactivated lysates, along with an equimolar mixture of NTPs (Sigma-Aldrich, 25 mM each) were equilibrated at 37° C. for 10 minutes. At time t=0, 9 volumes of heat-inactivated lysate supernatant were combined with 1 volume of NTP solution, and the reaction monitored by sampling into acid quench solution, pH-neutralized, filtered, and analyzed by LC-MS as described above. For transcription reactions in lysates, 10 μL reactions were performed using the MegaScript T7 Transcription Kit (Thermo Fisher) following kit instructions, except for a reduced amount of enzyme mix (5% of final reaction volume), and including heat-inactivated lysate supernatant (40% of final reaction volume). Positive control reactions were performed in MegaScript reaction buffer alone, while negative control reactions included lysate but omitted enzyme mix. Reactions were analyzed by agarose gel electrophoresis stained with SYBR Safe (Invitrogen) alongside the 1 kb DNA ladder (New England Biolabs).

Nucleotide Kinase Activity Assays

Nucleotide kinases were assayed at varying temperatures (37° C., 50° C., 60° C., 70° C. and 80° C.) in a buffer consisting of 50 mM Tris-HCl pH 7.0, 4 mM $MgSO_4$, 4 mM ATP, and 4 mM of the corresponding NMP or NDP. Reaction buffer (1.2× concentrate) and enzyme solution (0.5 mg/mL) were pre-equilibrated at reaction temperature for 1 minute before reactions were initiated. At time t=0, reactions were initiated by mixing 80 μL reaction buffer with 20 μL enzyme. Reactions were monitored by sampling at the indicated time points. During sampling, 15 μL of reaction mixture were transferred to 135 μL of 0.2M sulfuric acid on ice. After completion of the reaction, samples were pH-neutralized with 1M KOH as described above, then diluted 1:10 in ice-cold water. ATP was quantified in each sample using the ATP Bioluminescent Assay Kit (Sigma-Aldrich), following kit instructions. For reactions in lysates, the above protocol was modified as follows: lysates were aliquoted into individual reaction tubes, then heat-inactivated by incubating at 70° C. for 15 minutes. Reaction buffer (2× concentrate) and heat-inactivated lysates were pre-equilibrated at reaction temperature, and the reactions initiated by combining equal volumes of lysate and reaction buffer. Reactions were sampled by quenching individual reaction tubes with 9 volumes acid quench solution, then analyzed as described above.

To assay the combined activity of kinases in lysates (i.e. from NMPs to NTPs), lysates individually expressing each kinase were mixed in a 1:1 ratio, divided into 10 µL aliquots, then heat-inactivated as described above. Kinase activity was analyzed in a buffer consisting of 50 mM Tris-HCl pH 7.0, 16 mM $MgSO_4$, 2 mM each nucleotide monophosphate (AMP, CMP, UMP, and GMP), and 16 mM ATP. Reaction buffer (2× concentrate) pre-equilibrated at reaction temperature was combined with an equal volume of lysate to initiate the reaction. Reactions were performed at 70° C. and sampled by quenching individual reaction tubes with 9 volumes acid quench solution, then analyzed as described above.

Polyphosphate Kinase Activity Assays

Polyphosphate kinases were assayed at varying temperatures (37° C., 50° C., 60° C. 70° C., and 80° C.) in a buffer consisting of 50 mM Tris-HCl pH 7.0, 4 mM $MgSO_4$, 25 mM $(NH_4)_2SO_4$, 1 mM ADP, and 1 mM sodium hexametaphosphate. Reaction buffer (1.2× concentrate) and enzyme solution (0.25 mg/mL) were pre-equilibrated at reaction temperature for 1 minute before reactions were initiated. At time t=0, reactions were initiated by mixing 80 µL reaction buffer with 20 µL enzyme. Reactions were monitored by sampling at the indicated time points. During sampling, 15 µL of reaction mixture were transferred to 135 µL of 0.2M sulfuric acid on ice. After completion of the reaction, samples were pH-neutralized with 1M KOH as described above, then diluted 1:10 in ice-cold water. ATP was quantified in each sample using the ATP Bioluminescent Assay Kit (Sigma-Aldrich), following kit instructions. For reactions in lysates, the above protocol was modified as follows: lysates were aliquoted into individual reaction tubes, then heat-inactivated by incubating at 70° C. for 15 minutes. Reaction buffer (2× concentrate) and heat-inactivated lysates were pre-equilibrated at reaction temperature, and the reactions initiated by combining equal volumes of lysate and reaction buffer. Reactions were sampled by quenching individual reaction tubes with 9 volumes acid quench solution, then analyzed as described above. Reaction rates in lysates were calculated by subtracting signal from a control lysate (without overexpressed polyphosphate kinase) under the same reaction conditions.

Generation of Transcription Templates

Duplex DNA template was prepared by PCR amplification of synthetic gBlock DNA (Integrated DNA Technologies). Reactions were purified and concentrated by isopropanol precipitation.

RNA Polymerase Downselection

Commercially-available RNA polymerases were compared using conditions recommended by each manufacturer. Each 50 µL reaction consisted of 10× reaction buffer (supplied by the manufacturer), NTPs, DNA template (0.5 µg), and enzyme. For the NEB T7 RNA polymerase, reactions included 0.5 mM each NTP, 5 mM DTT, and 100 U enzyme. Reactions with ThermoT7 polymerase were identical, except that DTT was omitted. Reactions with MegaScript T7 included 7.5 mM each NTP and 5 µL enzyme mix. Enzyme concentrations were determined by BCA assay (Thermo Fisher). Reactions were monitored by sampling at the indicated time points. During sampling, 10 µL of reaction mixture were transferred to 90 µL of RNA quench solution (10 mM Tris-HCl pH 8.0, 5 mM EDTA) and stored on ice. RNA samples in quench solution were quantified using the Quant-iT RNA Broad Range Assay Kit (Thermo Fisher), following kit instructions. Serial dilutions of purified dsRNA, prepared using the MegaScript Kit and purified following kit instructions, were used to construct standard curves for quantitation. Reactions were qualitatively analyzed by agarose gel electrophoresis.

RNA Polymerase Evaluation in Lysates

GL14-322 lysates were heat-inactivated and clarified by centrifugation as described previously. Each 20 µL reaction consisted of clarified lysate (7 µL), 10× cofactor solution (300 mM $MgCl_2$, 20 mM spermidine). NTPs (7.5 mM each, prepared from pH-neutralized stock solutions), DNA template (0.6 µg), and enzyme (1 µL). Reactions were incubated for 1 hour at 37° C. or 50° C., then quenched by adding 9 volumes RNA quench solution. Quenched reactions were further diluted 10-fold in quench solution (final dilution: 100-fold). Diluted reactions were then quantified using the Quant-iT kit (see above). RNA produced by the reaction was calculated by subtracting RNA quantified in a control reaction (omitting RNA polymerase).

RNA polymerase assays in high-density lysates were performed as described above, with the following modifications. Each 100 µL reaction consisted of lysate (67.5 µL), 10× cofactor solution (300 mM $MgCl_2$, 20 mM spermidine), NTPs (7.5 mM each, prepared from pH-neutralized stock solutions), DNA template (3 µg), and enzyme (10 µL). For reactions performed in unclarified reaction matrix, GL14-322 lysates (67.5 µL) were aliquoted into individual reaction tubes, then heat-inactivated as described previously. Additional reactants were added to heat-inactivated matrix, then mixed well by vortexing until homogenous. For reactions performed in buffer, the 10× cofactor solution consisted of 300 mM $MgCl_2$, 20 mM spermidine, and 400 mM DTT. In addition, 50 mM potassium phosphate pH 7.4 was included in buffer-only reactions. All reactions were incubated for 2 hours at 50° C. Samples from each reaction were quenched by adding 9 volumes RNA quench solution, then clarified by centrifugation for 1 minute at maximum speed (21,000×g). Supernatants from these reactions were further diluted 40-fold in quench solution (final dilution: 400-fold), then quantified using the Quant-iT kit (see above).

Example 2

Thermostable PPK2 enzymes were codon-optimized for expression in *E. coli*, synthesized, and cloned into pET-Duet-1 (Novagen). Plasmids were then transformed into GL16-170. To generate the Control strain, empty pETDuet-1 plasmid was transformed into GL16-170. After overnight preculture in 5 mL Lysogeny Broth (LB), strains were cultivated in 1 L LB at 37° C. until cell densities reached an $OD_{600}$ of approximately 0.5. Cultures were then briefly chilled on ice, and PPK2 expression was induced by adding isopropyl thiogalactopyranoside (IPTG) to a final concentration of 0.25 mM. Post-induction, cultures were grown at 20° C. for approximately 16 hours. Cultures were harvested by centrifugation, and the cell pellets stored at −80° C. Lysates were produced by thawing frozen pellets, resuspending in 2 pellet volumes 150 mM MOPS-NaOH pH 7, and homogenizing using 4 passes through an EmulsiFlex C3 homogenizer (Avestin) at 15,000 psi. Lysates were then clarified by centrifugation at 15,000×g for 1 hour at 4° C. Aliquots of lysates were frozen at −80° C. before use.

Thermostable PPK2 activity was then measured in heat-inactivated lysates. Thawed lysates expressing PPK2 enzymes were first diluted 1:100 into lysates prepared from the Control strain, except for the D. geothermalis PPK2 lysate, which was diluted 1:10. Pre-chilled solutions of manganese chloride (MnCl$_2$) and sodium hexametaphosphate (HMP) were added to final concentrations of 10 mM and 1 mM, respectively. Lysates were then heat-inactivated by incubation in a pre-heated 70° C. thermocycler for 15 minutes. Reactions were then initiated by mixing heat-inactivated lysates with an equal volume of 2× Reaction Buffer, consisting of 10 mM MnCl$_2$, 2 mM adenosine diphosphate (ADP) or adenosine monophosphate (AMP), and 9 mM HMP. Reactions were incubated at 70° C., and time points were taken by removing an aliquot of reaction mixture and diluting with 9 parts Quench Solution (200 mM H$_2$SO$_4$) on ice. The initial timepoint (t$_0$) was taken by directly mixing lysate with Quench Solution, storing the quenched lysate on ice for 15 minutes, then adding 2× reaction buffer. At the conclusion of the assay, quenched timepoint solutions were clarified by centrifugation at 3,200×g for 10 minutes. Supernatants from the quenched reactions were then pH neutralized by mixing 3 parts quenched reaction solution with 1 part Neutralization Solution (1M KOH). Quenched and neutralized samples were then diluted 1:10 with water before quantitation using the Adenosine 5'-triphosphate (ATP) Bioluminescent Assay Kit (Sigma-Aldrich cat #: FLAA), following kit instructions. Initial reaction rates were calculated based on the accumulation of ATP in PPK2-containing reactions, subtracting ATP concentrations from the Control lysate.

Figure 22A:
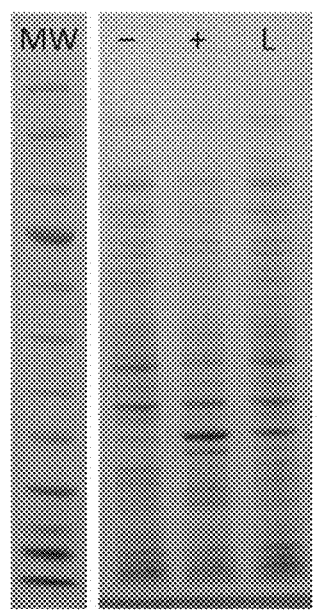
FIG. 22A is an image of an SDS-PAGE gel showing expression and solubility data for *A. thermophila* PPK2 in *E. coli* strain GL16-170. MW: Unstained Protein Standard, Broad Range (New England Biolabs Cat #P7704). –: Pre-induction culture. +: Induced culture at harvest. L: Soluble protein in clarified lysates. *A. thermophila* PPK2: 33 kDa.
Figure 22B:
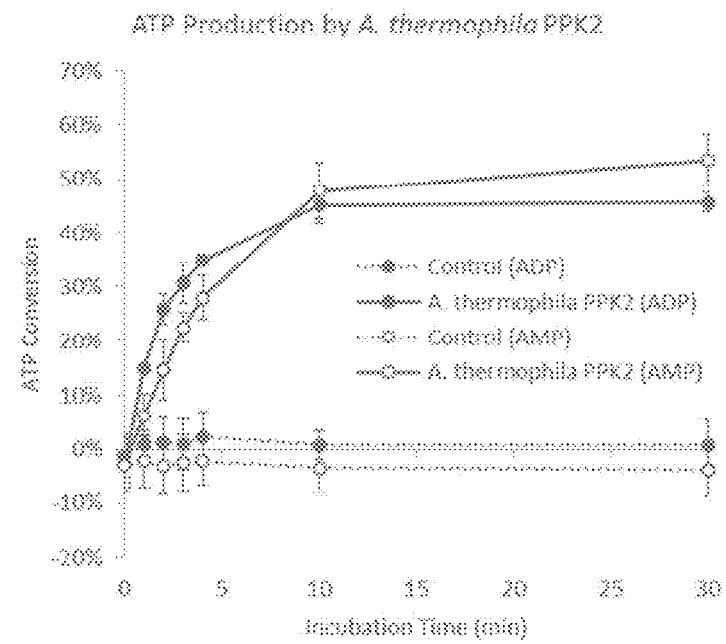
FIG. 22B is a graph showing ATP production of *A. thermophila* PPK2 in heat-inactivated lysates. Closed circles denote ATP production from ADP. Open circles denote ATP production from AMP. For both substrates, *A. thermophila* PPK2 produces ATP at rates exceeding 400 mM/hr.

Five Class III PPK2 enzymes exhibited soluble expression, thermostability, and high reaction rates in lysates at 70° C. Representative expression and activity data is shown in FIGS. 22A-22B.

A summary of expression and kinetic data for each tested enzyme is shown in Table 17. The C. aerophila, Roseiflexus, A. thermophila, and R. castenholzii enzymes rapidly converted AMP and ADP to ATP using HMP as a substrate. The D. geothermalis enzyme exhibited conversion rates roughly 20× lower than other tested PPK2s for both AMP and ADP substrates.

TABLE 17

Summary of expression and rate data for thermostable Class III PPK2 enzymes in lysates.

| Source Organism | Soluble Expression | V$_{max}$ (ADP) (mM ATP/hr) | V$_{max}$ (AMP) (mM ATP/hr) |
|---|---|---|---|
| C. aerophila DSM 14535 | + | 600 | 350 |
| Roseiflexus sp. RS-1 | ++ | 680 | 470 |
| A. thermophila UNI-1 | ++ | 530 | 480 |
| D. geothermalis DSM 11300 | +++ | 21 | 17 |
| R. castenholzii DSM 13941 | + | 530 | 370 |

Example 3

Thermostable C. aerophila PPK2 was then used to supply ATP for cell-free production of dsRNA from NMPs, ADP, and HMP. Cell-free dsRNA synthesis reactions were performed with a mixture of six E. coli lysates individually overexpressing the kinases detailed in Table 18.

TABLE 18

Kinases used to produce dsRNA from NMPs and HMP.

| Substrate(s) | Source Organism | Gene |
|---|---|---|
| AMP | Thermus thermophilus | adk |
| CMP | Thermus thermophilus | cmk |
| GMP | Thermotoga maritima | gmk |
| UMP | Pyrococcus furiosus | pyrH |
| ADP, CDP, GDP, UDP | Aquifex aeolicus | ndk |
| AMP, ADP, HMP | Caldilinea aerophila DSM 14535 | ppk2 |

First, lysates detailed in Table 18 were combined in equal volumes on ice. Pre-chilled solutions of manganese chloride (MnCl$_2$), magnesium sulfate (MgSO$_4$), and sodium hexametaphosphate (HMP) were added to final concentrations of 0-2.5 mM, 30 mM, and 1 mM, respectively. The lysate mixture was then heat-inactivated by incubation in a pre-heated 70° C. thermocycler for 15 minutes. To initiate the reactions, heat-inactivated lysates were combined with the following components: an equimolar mixture of nucleotide monophosphates (adenosine 5'-monophosphate, cytidine 5'-monophosphate, uridine 5'-monophosphate, and guanosine 5'-monophosphate, 2 mM each), 50 mM Tris pH 7.0, 30 mM MgSO$_4$, 0-2.5 mM MnCl$_2$, 1 mM adenosine 5'-diphosphate, 2 mM spermidine, 1.5 µg plasmid DNA template, and 3 µg thermostable T7 RNA polymerase (S430P, F849I, F880Y) in a total volume of 20 µL. As a control, dsRNA was synthesized from an equimolar mixture of 2 mM NTPs (with lysates, ADP, and HMP omitted). As an additional control, dsRNA was synthesized from an equimolar mixture of 2 mM NMPs (with PPK2-expressing lysate, ADP, and HMP omitted, but including 8 mM ATP as an energy source). As negative controls, duplicate reactions were performed omitting polymerase. All reactions were incubated at 50° C. for 2 hours, then terminated by the addition of 9 volumes TE+ buffer (10 mM Tris-HCl pH 8.0, 5 mM EDTA). Samples were mixed with an equal volume of 2×RNA Loading Dye (New England Biolabs) and heated to 70° C. for 10 minutes, followed by agarose/TAE gel electrophoresis.

Figure 23:
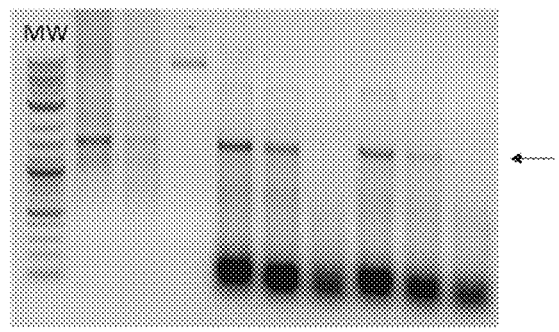
FIG. 23 is an image of an agarose gel demonstrating application of thermostable Class III PPK2 for energy generation in cell-free dsRNA production. Left lanes contain positive controls, demonstrating dsRNA synthesis from NTPs. Middle lanes contain positive controls, demonstrating dsRNA synthesis from NMPs in nucleotide kinase-expressing lysates using exogenous ATP as an energy source. Right lanes contain reactions demonstrating dsRNA synthesis from NMPs and HMP using nucleotide kinase and *C. aerophila* Ppk-expressing lysates. In each case, cell-free RNA synthesis reactions are $Mn^{2+}$ independent. Reactions without polymerase are included as negative controls, illustrating background nucleic acid content of each lysate-containing reaction.

As shown in FIG. 23, the desired dsRNA product was produced in buffer using NTPs (left lanes), in nucleotide kinase-expressing lysates from NMPs and ATP (middle lanes), and in nucleotide kinase and polyphosphate kinase-expressing lysates from NMPs and HMP (right lanes). Manganese chloride was not required in any reaction, demonstrating that the C. aerophila enzyme can utilize Mg$^{2+}$ as a cofactor as well as Mn$^{2+}$. Therefore, Mn$^{2+}$ is not required a priori for cell-free reactions containing C. aerophila PPK2.

Figure 24:
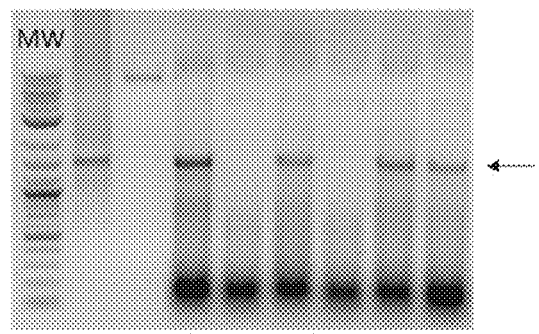
FIG. 24 is an image of an agarose gel demonstrating application of thermostable Class III PPK2 for energy generation in cell-free dsRNA production. Left lanes contain positive controls, demonstrating dsRNA synthesis from NTPs. Middle lanes contain positive controls, demonstrating dsRNA synthesis from NMPs in nucleotide kinase-expressing lysates using exogenous ATP as an energy source. Right lanes contain reactions demonstrating dsRNA synthesis from NMPs and HMP using nucleotide kinase and *C. aerophila* Ppk-expressing lysates. With *C. aerophila* PPK2, dsRNA synthesis proceeds in the absence of AMP kinase and exogenous ADP.

As shown in FIG. 24, the desired dsRNA product was produced in buffer using NTPs (left lanes), in nucleotide kinase-expressing lysates from NMPs and ATP (middle lanes), and in nucleotide kinase and polyphosphate kinase-expressing lysates from NMPs and HMP (right lanes). dsRNA production from NMPs and HMPs did not require exogenous ADP or T. thermophilus AMP kinase. Therefore, C. aerophila PPK2 can be used as part of a 5-kinase system to produce dsRNA from NMPs and HMP in cell-free reactions.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Maekewa K., Tsunasawa S., Dibo G., Sakiyama F. 1991. "Primary structure of nuclease P1 from *Penicillium citrinum*." Eur. J. Biochem. 200:651-661.
2. Volbeda A., Lahm A., Sakiyama F., Suck D. 1991. Crystal structure of *Penicillium citrinum* P1 nuclease at 2.8-A resolution. EMBO J. 10:1607-1618(1991)
3. Romier C., Dominguez R., Lahm A., Dahl O., Suck D. 1998. Recognition of single-stranded DNA by nuclease P1: high resolution crystal structures of complexes with substrate analogs. Proteins 32:414-424
4. Cheng Z. F., Deutscher M. P. 2002. Purification and characterization of the *Escherichia coli* exoribonuclease RNase R. Comparison with RNase II. J. Biol. Chem. 277:21624-21629.
5. Zilhao R., Camelo L., Arraiano C. M. 1993. DNA sequencing and expression of the gene mb encoding *Escherichia coli* ribonuclease II. Mol. Microbiol. 8:43-51
6. March P. E., Ahnn J., Inouye M. 1985. The DNA sequence of the gene (rnc) encoding ribonuclease III of *Escherichia coli*. Nucleic Acids Res. 13:4677-4685
7. Chen S. M., Takiff H. E., Barber A. M., Dubois G. C., Bardwell J. C., Court D. L. 1990. Expression and characterization of RNase III and Era proteins. Products of the rnc operon of *Escherichia coli*. J. Biol. Chem. 265:2888-2895
8. Robertson H. D., Webster R. E., Zinder N. D. 1968. Purification and properties of ribonuclease III from *Escherichia coli*. J. Biol. Chem. 243:82-91.
9. Molina L., Bernal P., Udaondo Z., Segura A., Ramos J. L. 2013. Complete Genome Sequence of a *Pseudomonas putida* Clinical Isolate, Strain H8234. Genome Announc. 1:E00496-13; and Cheng, Z. F. and M. P. Deutscher. 2002. Purification and characterization of the *Escherichia coli* exoribonuclease RNAse R. Comparison with RNAse II. J Biol Chem. 277(24).
10. Even S., Pellegrini O., Zig L., Labas V., Vinh J., Brechemmier-Baey D., Putzer H. 2005. Ribonucleases J1 and J2: two novel endoribonucleases in *B. subtilis* with functional homology to *E. coli* RNase E. Nucleic Acids Res. 33:2141-2152.
11. Li de la Sierra-Gallay I., Zig L., Jamalli A., Putzer H. 2008. Structural insights into the dual activity of RNase J. Nat. Struct. Mol. Biol. 15:206-212.
12. Ball T. K., Saurugger P. N., Benedick M. J. 1987. The extracellular nuclease gene of *Serratia marcescens* and its secretion from *Escherichia coli*. Gene 57:183-192.
13. Biedermann K., Jepsen P. K., Riise E., Svendsen I. 1989. Purification and characterization of a *Serratia marcescens* nuclease produced by *Escherichia coli*. Carlsberg Res. Commun. 54:17-27.
14. Shlyapnikov S. V., Lunin V. V., Perbandt M., Polyakov K. M., Lunin V. Y., Levdikov V. M., Betzel C., Mikhailov A. M. 2000. Atomic structure of the *Serratia marcescens* endonuclease at 1.1 A resolution and the enzyme reaction mechanism. Acta Crystallogr. D 56:567-572.
15. Zuo Y., Deutscher M. P. 2002. Mechanism of action of RNase T. I. Identification of residues required for catalysis, substrate binding, and dimerization. J. Biol. Chem. 277:50155-50159.
16. Zuo Y., Zheng H., Wang Y., Chruszcz M., Cymborowski M., Skarina T., Savchenko A., Malhotra A., Minor W. 2007. Crystal structure of RNase T, an exoribonuclease involved in tRNA maturation and end turnover. Structure 15:417-428.
17. Huang S., Deutscher M. P. 1992. Sequence and transcriptional analysis of the *Escherichia coli* rnt gene encoding RNase T. J. Biol. Chem. 267:25609-25613.
18. Chauhan A. K., Miczak A., Taraseviciene L., Apirion D. 1991. Sequencing and expression of the me gene of *Escherichia coli*. Nucleic Acids Res. 19:125-129.

19. Cormack R. S., Genereaux J. L., Mackie G. A. 1993. RNase E activity is conferred by a single polypeptide: overexpression, purification, and properties of the ams/me/hmp1 gene product. Proc. Natl. Acad. Sci. U.S.A. 90:9006-9010.
20. Meador J. III, Kennell D. 1990. Cloning and sequencing the gene encoding *Escherichia coli* ribonuclease I: exact physical mapping using the genome library. Gene 95:1-7.
21. Awano N., Rajagopal V., Arbing M., Patel S., Hunt J., Inouye M., Phadtare S. 2010. *Escherichia coli* RNase R has dual activities, helicase and RNase. J. Bacteriol. 192:1344-1352.
22. Regnier P., Grunberg-Manago M., Portier C. 1987. Nucleotide sequence of the pnp gene of *Escherichia coli* encoding polynucleotide phosphorylase. Homology of the primary structure of the protein with the RNA-binding domain of ribosomal protein S1. J. Biol. Chem. 262:63-68.
23. Kimhi Y., Littauer U. Z. 1968. Purification and properties of polynucleotide phosphorylase from *Escherichia coli*. J. Biol. Chem. 243:231-240.
24. Shi Z., Yang W. Z., Lin-Chao S., Chak K. F., Yuan H. S. 2008. Crystal structure of *Escherichia coli* PNPase: central channel residues are involved in processive RNA degradation. RNA 14:2361-2371.
25. Thaller M. C., Schippa S., Bonci A., Cresti S., Rossolini G. M. 1997. Identification of the gene (aphA) encoding the class B acid phosphatase/phosphotransferase of *Escherichia coli* MG 1655 and characterization of its product. FEMS Microbiol. Lett. 146:191-198.
26. Forleo C., Benvenuti M., Calderone V., Schippa S., Docquier J. D., Thaller M. C., Rossolini G. M., Mangani S. 2003. Expression, purification, crystallization and preliminary X-ray characterization of the class B acid phosphatase (AphA) from *Escherichia coli*. Acta Crystallogr. D 59:1058-1060.
27. Shuttleworth H., Taylor J., Minton N. 1986. Sequence of the gene for alkaline phosphatase from *Escherichia coli* JM83. Nucleic Acids Res. 14:8689-8689.
28. Bradshaw R. A., Cancedda F., Ericsson L. H., Neumann P. A., Piccoli S. P., Schlesinger M. J., Shriefer K., Walsh K. A. 1981. Amino acid sequence of *Escherichia coli* alkaline phosphatase. Proc. Natl. Acad. Sci. U.S.A. 78:3473-3477.
29. Li C., Ichikawa J. K., Ravetto J. J., Kuo H.-C., Fu J. C., Clarke S. 1994. A new gene involved in stationary-phase survival located at 59 minutes on the *Escherichia coli* chromosome. J. Bacteriol. 176:6015-6022.
30. Kuznetsova E., Proudfoot M., Gonzalez C. F., Brown G., Omelchenko M. V., Borozan I., Carmel L., Wolf Y. I., Mori H., Savchenko A. V., Arrowsmith C. H., Koonin E. V., Edwards A. M., Yakunin A. F. 2006. Genome-wide analysis of substrate specificities of the *Escherichia coli* haloacid dehalogenase-like phosphatase family. J. Biol. Chem. 281:36149-36161.
31. Burns D. M., Beacham I. R. 1986. Nucleotide sequence and transcriptional analysis of the *E. coli* ushA gene, encoding periplasmic UDP-sugar hydrolase (5'-nucleotidase): regulation of the ushA gene, and the signal sequence of its encoded protein product. Nucleic Acids Res. 14:4325-4342.
32. Knoefel T., Straeter N. 1999. X-ray structure of the *Escherichia coli* periplasmic 5'-nucleotidase containing a dimetal catalytic site. Nat. Struct. Biol. 6:448-453.
33. Tremblay L. W., Dunaway-Mariano D., Allen K. N. 2006. Structure and activity analyses of *Escherichia coli* K-12 NagD provide insight into the evolution of biochemical function in the haloalkanoic acid dehalogenase superfamily. Biochemistry 45:1183-1193.
34. Golovan S., Wang G., Zhang J., Forsberg C. W. 2000. Characterization and overproduction of the *Escherichia coli* appA encoded bifunctional enzyme that exhibits both phytase and acid phosphatase activities. Can. J. Microbiol. 46:59-71.
35. Greiner R. Jany K.-D. 1991. Characterization of a phytase from *Escherichia coli*. Biol. Chem. Hoppe-Seyler 372:664-665.
36. El Bakkouri M. Gutsche I, Kanjee U, Zhao B, Yu M, Goret G, Schoehn G, Burmeister W P, Houry W A. 2010. Structure of RavA MoxR AAA+ protein reveals the design principles of a molecular cage modulating the inducible lysine decarboxylase activity. Proc Natl Acad Sci USA 107(52); 22499-504. PMID: 21148420
37. Tchigvintsev A, Tchigvintsev D, Flick R, Popovic A, Dong A, Xu X, Brown G, Lu W, Wu H, Cui H, Dombrowski L, Joo J C, Beloglazova N, Min J, Savchenko A, Caudy A A, Rabinowitz J D, Murzin A G, Yakunin A F. 2013. Biochemical and structural studies of conserved maf proteins revealed nucleotide pyrophosphatases with a preference for modified nucleotides. Chem Biol 20(11): 1386-98. PMID: 24210219
38. Zhang J., Inouye M. 2002. MazG, a nucleoside triphosphate pyrophosphohydrolase, interacts with Era, an essential GTPase in *Escherichia coli*. J. Bacteriol. 184:5323-5329.
39. Smallshaw J. E., Kelln R. A. 1992. Cloning, nucleotide sequence and expression of the *Escherichia coli* K-12 pyrH gene encoding UMP kinase. Life Sci. Adv. (Genet.) 11:59-65.
40. Briozzo P., Evrin C., Meyer P., Assairi L., Joly N., Barzu O., Gilles A.-M. 2005. Structure of *Escherichia coli* UMP kinase differs from that of other nucleoside monophosphate kinases and sheds new light on enzyme regulation. J. Biol. Chem. 280:25533-25540.
41. Masui R., Kurokawa K., Nakagawa N., Tokunaga F., Koyama Y., Shibata T., Oshima T., Yokoyama S., Yasunaga T., Kuramitsu S. Complete genome sequence of *Thermus thermophilus* HB8. Submitted (November-2004) to the EMBL/GenBank/DDBJ databases.
42. Marco-Marin C., Escamilla-Honrubia J. M., Rubio V. 2005. First-time crystallization and preliminary X-ray crystallographic analysis of a bacterial-archaeal type UMP kinase, a key enzyme in microbial pyrimidine biosynthesis. Biochim. Biophys. Acta 1747:271-275.
43. Marco-Marin C., Escamilla-Honrubia J. M., Rubio V. 2005. First-time crystallization and preliminary X-ray crystallographic analysis of a bacterial-archaeal type UMP kinase, a key enzyme in microbial pyrimidine biosynthesis. Biochim. Biophys. Acta 1747:271-275.
44. Fricke J., Neuhard J., Kelln R. A., Pedersen S. 1995. The cmk gene encoding cytidine monophosphate kinase is located in the rpsA operon and is required for normal replication rate in *Escherichia coli*. J. Bacteriol. 177:517-523.
45. Briozzo P., Golinelli-Pimpaneau B., Gilles A. M., Gaucher J. F., Burlacu-Miron S., Sakamoto H., Janin J., Barzu O. 1998. Structures of *Escherichia coli* CMP kinase alone and in complex with CDP: a new fold of the nucleoside monophosphate binding domain and insights into cytosine nucleotide specificity. Structure 6:1517-1527.
46. Maeder D. L., Weiss R. B., Dunn D. M., Cherry J. L., Gonzalez J. M., DiRuggiero J., Robb F. T. 1999. Divergence of the hyperthermophilic archaea *Pyrococcus furio-* sus and *P. horikoshii* inferred from complete genomic sequences. Genetics 152:1299-1305.
47. Gentry D, Bengra C, Ikehara K, Cashel M. 1993. Guanylate kinase of *Escherichia coli* K-12." J Biol Chem 1993;268(19):14316-21. PMID: 8390989.
48. Hible G, Daalova P, Gilles A M, Cherfils J. 2006. Crystal structures of GMP kinase in complex with ganciclovir monophosphate and Ap5G." Biochimie 88(9); 1157-64. PMID: 16690197
49. Nelson K. E., Clayton R. A., Gill S. R., Gwinn M. L., Dodson R. J., Haft D. H., Hickey E. K., Peterson J. D., Nelson W. C., Ketchum K. A., McDonald L. A., Utterback T. R., Malek J. A., Linher K. D., Garrett M. M., Stewart A. M., Cotton M. D., Pratt M. S. Fraser C. M. 1999. Evidence for lateral gene transfer between Archaea and Bacteria from genome sequence of *Thermotoga maritima*. Nature 399:323-329.
50. Brune M., Schumann R., Wittinghofer F. 1985. Cloning and sequencing of the adenylate kinase gene (adk) of *Escherichia coli*. Nucleic Acids Res. 13:7139-7151.
51. Berry M. B., Bae E., Bilderback T. R., Glaser M., Phillips G. N. Jr. 2006. Crystal structure of ADP/AMP complex of *Escherichia coli* adenylate kinase. Proteins 62:555-556.
52. Henne A., Brueggemann H., Raasch C., Wiezer A., Hartsch T., Liesegang H., Johann A., Lienard T., Gohl O., Martinez-Arias R., Jacobi C., Starkuviene V., Schlenczeck S., Dencker S., Huber R., Klenk H.-P., Kramer W., Merkl R., Gottschalk G., Fritz H.-J. 2004. The genome sequence of the extreme thermophile *Thermus thermophilus*. Nat. Biotechnol. 22:547-553.
53. Tan Z W, Liu J, Zhang X F, Meng F G, Zhang Y Z. Nan Fang Yi Ke Da Xue Xue Bao. 2010. Expression, purification and enzymatic characterization of adenylate kinase of *Thermus thermophilus* HB27 in *Escherichia coli*. January; 30(1): 1-6
54. Moffatt B. A., Dunn J. J., Studier F. W. 1984. Nucleotide sequence of the gene for bacteriophage T7 RNA polymerase. J. Mol. Biol. 173:265-269.
55. Sousa R., Chung Y. J., Rose J. P., Wang B.-C. 1993. Crystal structure of bacteriophage T7 RNA polymerase at 3.3-A resolution. Nature 364:593-599.
56. Mindich L., Nemhauser I., Gottlieb P., Romantschuk M., Carton J., Frucht S., Strassman J., Bamford D. H., Kalkkinen N. 1988. Nucleotide sequence of the large doublestranded RNA segment of bacteriophage phi 6: genes specifying the viral replicase and transcriptase. J. Virol. 62:1180-1185.
57. McGraw N. J., Bailey J. N., Cleaves G. R., Dembinski D. R., Gocke C. R., Joliffe L. K., Macwright R. S., McAllister W. T. 1985. Sequence and analysis of the gene for bacteriophage T3 RNA polymerase. Nucleic Acids Res. 13:6753-6766.
58. Kotani H., Ishizaki Y., Hiraoka N., Obayashi A. 1987. Nucleotide sequence and expression of the cloned gene of bacteriophage SP6 RNA polymerase. Nucleic Acids Res. 15:2653-2664.

Sequences

*E. coli* RNase R
MSQDPFQEREAEKYANPIPSREFILEHLTKREKPASRDELAVELHIEGEE
QLEGLRRRLRAMERDGQLVFTRRQCYALPERLDLVKGTVIGHRDGYGFLR
VEGRKDDLYLSSEQMKTCIHGDQVLAQPLGADRKGRREARIVRVLVPKTS
QIVGRYFTEAGVGFVVPDDSRLSFDILIPPDQIMGARMGFVVVVELTQRP
TRRTKAVGKIVEVLGDNMGTGMAVDIALRTHEIPYIWPQAVEQQVAGLKE
EVPEEAKAGRVDLRDLPLVTIDGEDARDFDDAVYCEKKRGGGWRLWVAIA
DVSYYVPRPSTPLDREARNRGTSVYFPSQVIPMLPEVLSNGLCSLNPQVD
RLCMCEMTVSSKGRLTGYKFYEAVMSSHARLTYTKVWHILOGDQDLREQY
APLVKHLEELHNLYKVLDKAREERGGISFESEEAKFIFNAERRIERIEQT
QRNDAHKLIEECMILANISAARFVEKAKEPALFRIHDKPSTEAITSFRSV
LAELGLELPGGNKPEPREYAELLESVADRPDAEMLQTMLLRSMKQAIYDP
ENRGHFGLALQSYAHFISPIRRYPDLTLHRAIKYLLAKEQGHQGNTTETG
GYHYSMEEMLQLGQHCSMAERRADEATRDVADWLKCDFMLDQVGNVFKGV
ISSVTGFGFFVRLDDLFIDGLVHVSSLDNDYYRFDQVGQRLMGESSGQTY
RLGDRVEVRVEAVNMDERKIDFSLISSERAPRNVGKTAREKAKKGDAGKK
GGKRRQVGKKVNFEPDSAFRGEKKTKPKAAKKDARKAKKPSAKTQKIAAA
TKAKRAAKKKVAE (SEQ ID NO: 1)

*T. elongatus* Ppk (PPK1)
MPSAKSPRRKAPEPIDLDNPQYYFNRSLSWLEFNKRVLHEAYDPRTPLLE
RLKFMAIFSSNLDEFFMVRVAGLKQQVESGILQVGADGMPPAEQLQAVRQ
YLLPIVTEQHRYFDQELRALLAKESIFLTRFNELTPEQQAYLNDYFQAQV
FPVLTPLAVDPAHPFPYISSLSLNLAVLIRDPESGQERLARVKVPNQFPR
FVALPQHLHSPQGVHWLGVPLEEIIAHNLSALFPGMEIEAYRAFRITRSA
DLELETDKADDLLIAIEQEIRKRRFGSVVRLEVQRGIPPLLRQTLMEEMD
LEEIDVYELEGLLCLNDLFAFMGLPLPQPKDPEWQPQVPPSFQRVEERES
MFDTSSEITTLGTDYWEAVANELFSLIREGDIIVHHPYHSFAATVQRFIT
LAAHDPQVLAIKITLYRTSGDSPIVSALIKAAENGKQVAVLVELKARFDE
ENNILWARKLEKVGVHVVYGVPGLKTHTKTVLVVRQEAGQIRRYVHIGTG
NYNPKTASLYEDLGLFSCREELGADLSELFNVLTGYARQRDYRKLLVAPV
TMRDRTLQLIYREIEHARNGQPARIIAKMNAITDTQVIRALYEASQAGVD
IDLIIRGMCCLRPGVPGVSDRIRVISIIGRFLEHSRIFYFGNNGDPEYYI
GSADWRSRNLDRRVEAITPIEDPAIQLELKERLEIMLADNRQAWELQPDG
TYRQRQPAPGEAERGTHSVLMARTLKDVQGSH (SEQ ID NO: 2)

*P. furiosus* Umk
MRIVFDIGGSVLVPENPDIDFIKEIAYQLTKVSEDHEVAVVVGGGKLARK
YIEVAEKFNSSETFKDFIGIQITRANAMLLIAALREKAYPVVVEDFWEAW
KAVQLKKIPVMGGTHPGHTTDAVAALLAEFLKADLLVVITNVDGVYTADP
KKDPTAKKIKKMKPEELLEIVGKGIEKAGSSSVIDPLAAKIIARSGIKTI
VIGKEDAKDLFRVIKGDHNGTTIEP (SEQ ID NO: 3)

*T. thermophilus* Cmk
MRGIVTIDGPSASGKSSVARRVAAALGVPYLSSGLLYRAAAFLALRAGVD
PGDEEGLLALLEGLGVRLLAQAEGNRVLADGEDLTSFLHTPEVDRVVSAV
ARLPGVRAWVNRRLKEVPPPFVAEGRDMGTAVFPEAAHKFYLTASPEVRA
WRRARERPQAYEEVLRDLLRRDERDKAQSAPAPDALVLDTGGMTLDEVVA
WVLAHIRR (SEQ ID NO: 4)

*T. maritima* Gmk
MKGQLFVICGPSGAGKTSIIKEVLKRLDNVVFSVSCTTRPKRPHEEDGKD
YFFITEEEFLKRVERGEFLEWARVHGHLYGTLRSFVESHINEGKDVVLDI
DVQGALSVKKKYSNTVFIYVAPPSYADLRERILKRGTEKEADVLVRLENA
KWELMFMDEFDYIVVNENLEDAVEMVVSIVRSERAKVTRNQDKIERFKME
VKGWKKL (SEQ ID NO: 5)

*T. thermophilus* Adk
MDVGQAVIFLGPPGAGKGTQASRLAQELGFKKLSTGDILRDHVARGTPLG
ERVRPIMERGDLVPDDLILELIREELAERVIFDGFPRTLAQAEALDRLLS
ETGTRLLGVVLVEVPEEELVRRIIRRAELEGRSDDNEETVRRLEVYRFK
TEPLVGYYEARGVLKRVDGLGTPDEVYARIRAALGI (SEQ ID NO: 6)

*A. aeolicus* Ndk
MAVERTLIIVKPDAMEKGALGKILDRFIQEGFQIKALKMFRFTPEKAGEF
YYVHRERPFFQELVEFMSSGPVVAAVLEGEDAIKRVREIIGPTDSEEARK
VAPNSIRAQFGTDKGKNAIHASDSPESAQYEICFIFSGLEIV (SEQ ID NO: 7)

*Meiothermus ruber* DM 1279 PPK2
MGFCSIEFLMGAQMKKYRVQPDGRFELKRFDPDDTSAFEGGKQAALEALA
VLNRRLEKLQELLYAEGQHKVLVVLQAMDAGGKDGTIRVVFDGVNPSGVR
VASFGVPTEQELARDYLERVHQQVPRKGELVIFNRSHYEDVLVRVKNLV
PQQVWQKRYRHIREFERMLADEGTTILKFFLHISKDEQRQRLQERLDNPE
KRWKFRMGDLEDRRLWDRYQEAYEAAIRETSTEYAPWYVIPANKNWYRNW
LVSHILVETLEGLAMQYPQPETASEKIVIE (SEQ ID NO: 8)

*Meiothermus silvanus* DSM 9946 PPK2
MAKTIGATLNLQDIDPRSTPGFNGDKEKALALLEKLTARLDELQEQLYAE
HQHRVLVILQGMDTSGKDGTIRHVFKNVDPLGVRVVAFKAPTPPELERDY
LWRVHQHVPANGELVIFNRSHYEDVLVARVHNLVPPAIWSRRYDHINAFE
KMLVDEGTTVLKFFLHISKEEQKKRLLERLVEADKHWKFDPQDLVERGYW EDYMEAYQDVLDKTHTQYAPWHVIPADRKWYRNLQVSRLLVEALEGLRMK
YPRPKLNIPRLKSELEKM (SEQ ID NO: 9)

*Deinococcus geothermalis* DSM 11300 PPK2
MQLDRYRVPPGQRVRLSNWPTDDDGGLSKAEGEALLPDLQQRLANLQERL
YAESQQALLIVLQARDAGGKDGTVKHVIGAFNPSGVQVSNFKVPTEEERA
HDFLWRIHRQTPRLGMIGVFNRSQYEDVLVTRVHHLIDDQTAQRRLKHIC
AFESLLTDSGTRIVKFYLHISPEEQKRLEARLADPSKHWKFNPGDLQER
AHWDAYTAVYEDVLTTSTPAAPWYVVPADRKWFRNLLVSQILVQTLEEMN
PQFPAPAFNAADLRIV (SEQ ID NO: 10)

*Thermosynechococcus elongantus* BP-1 PPK2
MIPQDFLDEINPDRYIVPAGGNFHWKDYDPGDTAGLKSKVEAQELLAAGI
KKLAAYQDVLYAQNIYGLLIIFQAMDAAGKDSTIKHVMSGLNPQACRVYS
FKAPSAEELDHDFLWRANRALPERGCIGIFNRSYYEEVLVVRVHPDLLNR
QQLPPETKTKHIWKERFEDINHYERYLTRNGILILKFFLHISKAEQKKRF
LERISRPEKNWKFSIEDVRDRAHWDDYQQAYADVFRHTSTKWAPWHIIPA
NHKWFARLMVAHFIYQKLASLNLHYPMLSEAHREQLLEAKALLENEPDED
(SEQ ID NO: 11)

*Anaerolinea thermophila* UNI-1 PPPK2
MGEAMERYFIKPGEKVRLKDWSPDPPPKDFEGDKESTRAAVAELNRKLEVL
QERLYAERKHKVLVILQGMDTSGKDGVIRSVFEGVNPQGVKVANFKVPTQ
EELDHDYLWRVHKVVPGKGEIVIFNRSHYEDVLVVRVHNLVPPEVWKKRY
EQINQFERLLHETGTTILKFFLFISREEQKQRLLERLADPAKHWKFNPGD
LKERALWEEYEKAYEDVLSRTSTEYAPWILVPADKKWYRDWVISRVLVET
LEGLEIQLPPPLADAETYRRQLLEEDAPESR (SEQ ID NO: 12)

*Caldilinea aerophila* DSM 14535 PPK2
MDVDRYRVPPGSTIHLSQWPPDDRSLYEGDKKQGKQDLSALNRRLETLQE
LLYAEGKHKVLIILQGMDTSGKDGVIRHVFNGVNPQGVKVASFKVPTAVE
LAHDFLWRIHRQTPGSSGEIVIFNRNRSHYEDVLVVRVHNLVPPEVWKKRY
EQINQFERLLHDEGTTILKFFLFISREEQKQRLLERLADPAKHWKFNPGD
LKERALWEEYEKAYEDVLSRTSTEYAPWILVPADKKWYRDWVISRVLVLE
GLNMRYPQPEDIAFDTIVIE (SEQ ID NO: 13)

*Chlorobaculum tepidum* TLS PPK2
MKLDLDAFRIQPGKKPNLAKRPTRIDPVYRSKGEYHELLANHVAELSKLQ
NVLYADNRYAILLIFQAMDAAGKDSAIKHVMGVNPQGCQVYSFKHPSATE LEHDFLWRTNCVLPERGRIGIFNRSYYEEVLVVRVHPEILEMQNIPHNLA
HNGKVWDHRYRSIVSHEQHLHCNGTRIVKFYLHLSKEEQRKRFLERIDDP
NKNWKFSTADLEERKFWDQYMEAYESCLQETSTKDSPWFAVPADDKKNAR
LIVSRIVLDTLESLNLKYPEPSPERRKELLDIRKRLENPENGK (SEQ
ID NO: 14)

*Oceanithermus profundus* DSM 14977 PPK2
MDVSRYRVPPGSGFDPEAWPTREDDDFAGGKKEAKKELARLAVRLGELQA
RLYAEGRQALLIVLQGMDTAGKDGTIRHVFRAVNPQGVRVTSFKKPTALE
LAHDYLWRVHRHAPARGEIGIFNRSHYEDVLVVRVHELVPPEVWGRRYDH
INAFERLLADTGTTRIVKFFLHISKDEQKRRLEARLENPRKHWKFNPADLS
ERARWGDYAAAYAEALSRTSSDRAPWYAVPADRKWQRNRIVAQVLVDALE
AMDPRFPRVDEPDPASVRVE (SEQ ID NO: 15)

*Roseiflexus castenholzi* DSM 13941 PPK2
MYAQRVVPGMRVRLHDIDPDANGGLNKDEGRARFAELNAELDVMQEELYA
AGIHALLLILQGMDTAGKDGAIRNVMLNPQGCRVESFKVPTEEELAHD
FLWRVHRVVPRKGMVGVFNRSHYEDVLVVRVHSLVPESVWRARYDQINAF
ERLLADTGTTIVKCFLHISKEEQEQRLLARERDVSKAWKLSAGDWRERAF
WDDYMAAYEEALTRCSTDYAPWYIIPANRKWYRDLAISEALVETLRPYRD
DWRRALDAMSRARRAELEAFRAEQHAMEGRPQGAGGVSRR (SEQ ID
NO: 16)

*Roseiflexus* sp. RS-1 PPK2
MHYAHTVIPGTQVRLRDIDPDASGGLTKDEGRERFASFNATLDAMQEELY
AAGVHALLLILQGMDTAGKDGAIRNVMHNLNPQGCRVESFKVPTEEELAH
DFLWRVHKVVPRKGMVGVFNRSHYEDVLVVRVHSLVPEHVWRARYDQINA
FERLLTDTGTIIVKCFLHISKDEQEKRLLAREQDVTKAWKLSAGDWRERE
RWDEYMAAYEEALTRCSTEYAPWYIIPANRKWYRDLAISEVLVETLRPYR
DDWQRALDAMSQARLAELKAFRHQQTAGATRL (SEQ ID NO: 17)

*Truepera radiovictrix* DSM 17093 PPK2
MSQGSAKGLGKLDKKVYARELALLQLELVKLQGWIKAQGLKVVVLFEGRD
AAGKGSTITRITQPLNPRVCRVVALGAPTERERTQWYFQRYVHHLPAAGE
MVLFDRSWYNRAGVERVMGFCTEAEYREFLHACPTFERLLLLDAGIILIKY
WFSVSAAEQERRMRRRNENPAKRWKLSPMDLEARARWVAYSKAKDAMFYH
TDTKASPWYVVNAEDKRRAHLSCIAHLLSLIPYEDLTPPPLEMPPRDLAG
ADEGYERPDKAHQTWVPDYVPPTR (SEQ ID NO: 18)

What is claimed is:

1. A cell-free method of biosynthesizing ribonucleic acid (RNA) of interest, the method comprising:
    (a) incubating a cell lysate mixture that comprises cellular RNA, an enzyme that depolymerizes RNA, a thermostable kinase, and a thermostable RNA polymerase, and producing a cell lysate mixture that comprises nucleoside monophosphates;
    (b) heating the cell lysate mixture produced in step (a) to a temperature that inactivates or partially inactivates the enzymes that depolymerize RNA and enzymes that degrade nucleotides and/or nucleic acids, without completely inactivating the thermostable kinases and thermostable RNA polymerases, and producing a cell lysate mixture that comprises nucleoside monophosphates, a thermostable kinase, and a RNA polymerase; and
    (c) incubating the cell lysate mixture produced in (b) in the presence of an energy source and a deoxyribonucleic acid (DNA) template encoding a RNA of interest, producing nucleoside triphosphates, and producing a cell lysate mixture that comprises the RNA of interest.

2. The method of claim 1, wherein the cell lysate mixture of step (a) comprises one or more cell lysates obtained from cells that comprise cellular RNA and/or express a ribonuclease, a kinase, and/or a RNA polymerase.

3. The method of claim 1, wherein the enzyme that depolymerizes RNA is a ribonuclease.

4. The method of claim 3, wherein the ribonuclease is selected from the group consisting of Nuclease P1, RNase R, PNPase, RNase II, RNase III, S1 nuclease, RNase JI, NucA, RNase T, RNase E, and RNase G.

5. The method of claim 1, wherein the at least one thermostable kinase is selected from the group consisting of thermostable nucleoside monophosphate kinases, thermostable nucleoside diphosphate kinases, and thermostable polyphosphate kinases.

6. The method of claim 5, wherein the thermostable nucleoside monophosphate kinases are selected from the group consisting of thermostable uridylate kinases, thermostable cytidylate kinases, thermostable guanylate kinases, and thermostable adenylate kinases.

7. The method of claim 5, wherein the thermostable nucleoside monophosphate kinases are selected from the group consisting of thermostable *Pyrococcus furiosus* uridylate kinases encoded by a pyrH gene (PfPyrH), thermo stable *Thermus thermophilus* adenylate kinases encoded by a adk gene (TthAdk), thermostable (Previously Pending) *Thermus thermophilus* cytidylate kinases encoded by a conk gene (TthCmk), and thermostable *Thermotoga maritima* guanylate kinases encoded by a gunk gene (TmGmk).

8. The method of claim 5, wherein the thermostable nucleoside diphosphate kinases are selected from the group consisting of thermostable *Aquifex aeolicus* nucleoside diphosphate kinases encoded by a ndk gene (AaNdk).

9. The method of claim 5, wherein the thermostable polyphosphate kinases are selected from the group consisting of thermostable polyphosphate kinase 1 (PPK1) enzymes and thermostable polyphosphate kinase 2 (PPK2) enzymes.

10. The method of claim 9, wherein the thermostable PPK1 enzymes are thermostable *Thermosynechococcus elongatus* PPK1 enzymes.

11. The method of claim 9, wherein the thermostable PPK2 enzymes are selected from the group consisting of thermostable Class I and/or Class III PPK2 enzymes.

12. The method of claim 11, wherein the thermostable Class III PPK2 enzymes are selected from the group consisting of *Meiothermus ruber, Meiothermus silvanus, Deinococcus geothermalis, Thermosynechococcus elongatus, Anaerolinea thermophila, Caldilinea aerophila, Chlorobaculum tepidum, Oceanithermus profundus, Roseiflexus castenholzii, Roseiflexus* sp., and *Truepera radiovictrix* PPK2 enzymes.

13. The method of claim 11, wherein the thermostable Class III PPK2 enzymes comprise an amino acid sequence that is at least 70% identical to the amino acid sequence identified by any one of SEQ ID NO: 8-18.

14. The method of claim 11, wherein the thermostable Class III PPK2 enzymes are *Deinococcus geothermalis* PPK2 enzymes.

15. The method of claim 11, wherein the thermostable Class III PPK2 enzymes comprise an amino acid sequence that is identical to the amino acid sequence identified by any one of SEQ ID NO: 8-18.

16. The method of claim 1, wherein the cell lysate mixture of step (a) comprises at least one ribonuclease, at least one thermostable nucleoside monophosphate kinase, at least one thermostable nucleoside diphosphate kinase, and at least one polyphosphate kinase.

17. The method of claim 1, wherein the at least one thermostable RNA polymerase is a thermostable DNA-dependent RNA polymerase.

18. The method of claim 17, wherein the thermostable DNA-dependent RNA polymerase is selected from the group consisting of thermostable T7 RNA polymerases, thermostable SP6 RNA polymerases, and thermostable T3 RNA polymerases.

19. The method of claim 1, wherein the energy source is adenosine triphosphate (ATP) or polyphosphate.

20. The method of claim 1, wherein the nucleotide triphosphates are produced using polyphosphate, nucleoside monophosphates, and polyphosphate kinase.

21. The method of claim 20, wherein the polyphosphate is hexametaphosphate.

22. The method of claim 20, wherein the nucleotide triphosphates are produced using polyphosphate, nucleoside monophosphates, polyphosphate kinase, nucleoside monophosphate kinases, and nucleoside diphosphate kinases.

23. The method of claim 1, wherein at least one purified enzyme or fusion enzyme is added to the cell lysate mixture of step (a), and wherein the at least one purified enzyme or fusion enzyme is selected from the group consisting of enzymes that depolymerize RNA, thermostable kinases, and thermostable polymerases RNA, under conditions that result in depolymerization of RNA to produce a cell lysate mixture that comprises nucleoside monophosphates.

24. The method of claim 1, wherein at least one purified enzyme or fusion enzyme is added to the cell lysate mixture of step (c), and wherein the at least one purified enzyme or fusion enzyme is selected from the group consisting of enzymes that depolymerize RNA, thermostable kinases, and thermostable polymerases RNA, under conditions that result in production of nucleoside triphosphates and polymerization of the nucleoside triphosphates to produce a cell lysate mixture that comprises the RNA of interest.

25. The method of claim 1, wherein the cell lysate mixture of step (a) comprises the DNA template encoding the RNA of interest used in step (c).

26. The method of claim 1, wherein the DNA template encoding the RNA of interest is added to the cell lysate mixture of step (c).

27. The method of claim 1, wherein the RNA of interest is a single-stranded RNA.

28. The method of claim 1, wherein the RNA of interest is a double-stranded RNA.

29. The method of claim 1, wherein the temperature of step (b) is 50° C.-80° C.

30. A cell lysate produced by the method of claim 1.

31. A method of producing a heat-inactivated cell lysate, the method comprising:
   (a) culturing in cell culture media cells that comprise cellular RNA, at least one exogenous ribonuclease, at least one thermostable kinase, and at least one thermostable RNA polymerase;
   (b) lysing the cells of (a) to produce a cell lysate; and
   (c) heating the cell lysate to a temperature that inactivates or partially inactivates the at least one exogenous ribonuclease, without completely inactivating the thermostable kinases and thermostable RNA polymerases, thereby producing the heat-inactivated cell lysate.

32. The method of claim 31 further comprising incubating the heat-inactivated cell lysate in the presence of an energy source and a deoxyribonucleic acid (DNA) template encoding a RNA of interest, under conditions that result in production of nucleoside triphosphates and polymerization of the nucleoside triphosphates to produce a heat-inactivated cell lysate that comprises the RNA of interest.

* * * * *

UNITED STATES PATENT AND TRADEMARK OFFICE
CERTIFICATE OF CORRECTION

PATENT NO. : 10,954,541 B2
APPLICATION NO. : 15/480617
DATED : March 23, 2021
INVENTOR(S) : William Jeremy Blake et al.

It is certified that error appears in the above-identified patent and that said Letters Patent is hereby corrected as shown below:

In the Claims

In Claim 7, at Column 97, Lines 48-52, the text:
"*Thermus thermophilus* adenylate kinases encoded by a adk gene (TthAdk), thermostable (Previously Pending) *Thermus thermophilus* cytidylate kinases encoded by a conk gene (TthCmk), and thermostable *Thermotoga maritima* guanylate kinases encoded by a gunk gene (TmGmk)."
Should be replaced with:
-- *Thermus thermophilus* adenylate kinases encoded by an *adk* gene (TthAdk), thermostable *Thermus thermophilus* cytidylate kinases encoded by a *cmk* gene (TthCmk), and thermostable *Thermotoga maritima* guanylate kinases encoded by a *gmk* gene (TmGmk). --

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*